US011186621B2

(12) United States Patent
Ko et al.

(10) Patent No.: US 11,186,621 B2
(45) Date of Patent: Nov. 30, 2021

(54) METHODS FOR ENHANCING THE PLURIPOTENCY OF STEM CELLS

(71) Applicants: Elixirgen, LLC, Baltimore, MD (US); The United States of America, as Represented by the Secretary for the Department of Health and Human Service, Bethesda, MD (US)

(72) Inventors: Minoru S. H. Ko, Cockeysville, MD (US); Tomokazu Amano, Parkville, MD (US)

(73) Assignees: Elixirgen, LLC, Baltimore, MD (US); The U.S. of America, as Represented by the Secretary for the Department of Health and Human Service, Bethesda, MD (US)

( * ) Notice: Subject to any disclaimer, the term of this patent is extended or adjusted under 35 U.S.C. 154(b) by 0 days.

(21) Appl. No.: 16/405,863

(22) Filed: May 7, 2019

(65) Prior Publication Data

US 2019/0330288 A1 Oct. 31, 2019

Related U.S. Application Data

(62) Division of application No. 14/006,954, filed as application No. PCT/US2012/030005 on Mar. 21, 2012, now Pat. No. 11,059,869.

(60) Provisional application No. 61/466,667, filed on Mar. 23, 2011.

(51) Int. Cl.

| | |
|---|---|
| ***C07K 14/47*** | (2006.01) |
| ***C12N 5/0735*** | (2010.01) |
| ***C12N 15/79*** | (2006.01) |
| ***C12N 15/62*** | (2006.01) |
| ***C07K 14/705*** | (2006.01) |
| ***C12N 5/074*** | (2010.01) |
| ***C12N 15/85*** | (2006.01) |
| ***C07K 14/72*** | (2006.01) |

(52) U.S. Cl.

CPC ........ *C07K 14/47* (2013.01); *C07K 14/70567* (2013.01); *C07K 14/721* (2013.01); *C12N 5/0606* (2013.01); *C12N 5/0696* (2013.01); *C12N 15/62* (2013.01); *C12N 15/79* (2013.01); *C12N 15/85* (2013.01); *C07K 2319/00* (2013.01)

(58) Field of Classification Search

CPC ...... C12N 5/0696; C12N 15/79; C12N 15/62; C12N 5/0606; C12N 15/85; C07K 14/70567; C07K 14/721; C07K 2319/00

See application file for complete search history.

(56) References Cited

U.S. PATENT DOCUMENTS

2003/0194704 A1 10/2003 Penn et al.
2010/0105043 A1* 4/2010 Ko ........................ C12N 5/0611 435/6.16
2012/0156305 A1* 6/2012 Ko .......................... A61P 37/06 424/499

FOREIGN PATENT DOCUMENTS

JP 2010522565 A 7/2010
WO WO-2004085654 A2 10/2004
WO WO-2008118957 A2 * 10/2008 ........... C12N 15/113
WO WO-2009020632 A1 2/2009
WO WO-2011028880 A2 * 3/2011 ........... C12N 5/0606
WO WO-2012129342 A1 9/2012

OTHER PUBLICATIONS

Romano, Drug News Prospect, 16(5): 267, 267-276 (Year: 2003).*
Dan et al Cell Reports 20, 1936-1949 (Year: 2017).*
Williams et al (Mol. Cell Biol. , 119(12) 8526-8535 (Year: 1999).*
Collins et al (Zinc Finger Proteins: From atomic contact to cellular function lands Bioscience, pp. 156-167 (Year: 2005).*
Andrews et al Biochem Soc Trans. 33(Pt 6):1526-30 (Year: 2005).*
Koestenbauer et al Am J Reprod Immunol. 55(3): 169-80 (Year: 2006).*
Hanna, Cell Stem Cell, 4:513-524 (Year: 2009).*
Chin Cell Stem Cell, 5:111-123 (Year: 2009).*
Storm et al The Journal of Biological Chemistry, 282, 6265-6273 (Year: 2007).*
ABS12112 or EF587699.1 (Year: 2007).*
Thomas et al Nature review 346-358 (Year: 2003).*
Sato et al Nature Medicine 10, 55-63 (Year: 2004).*
Blast sequence homology search SEQ ID No. 20 vs ERT2, pp. 1-2.
Blast sequence homology search SEQ ID No. 20 vs Zscan4, pp. 1-3.
Chambers et al., (2007). "Nanog Safeguards Pluripotency and Mediates Germline," Development Nature, 450:1230-1235.
Collins et al., (2005). "The Superfamily of SCAN Domain Containing Zinc Finger Transcription Factors," Zinc Finger Proteins: From Atomic Contact to Cellular Function, pp. 156-167.

(Continued)

*Primary Examiner* — Anoop K Singh
(74) *Attorney, Agent, or Firm* — Morrison & Foerster LLP

(57) ABSTRACT

Described herein is the finding that increasing the frequency of Zscan4 activation in mouse ES cells not only enhances, but also maintains their developmental potency in long-term cell culture. As the potency increases, even a whole animal can be produced from a single ES cell injected into a 4N blastocyst at an unexpectedly high success rate. The studies disclosed herein indicate that ES cells acquire higher potency by going through the transient Zscan4 activation state more frequently than the regular state. Particularly disclosed herein is the finding that the constitutive presence of Zscan4-ERT2, even in the absence of its usual activator tamoxifen, can increase the frequency of endogenous Zscan4 activation in ES cells, resulting in the increase of developmental potency of the ES cells. Accordingly, provided herein are Zscan4-ERT2 fusion proteins and nucleic acid molecules and vectors encoding Zscan4-ERT2 fusion proteins. Further provided are methods of prolonging and/or enhancing stem cell pluripotency using the disclosed Zscan4-ERT2 nucleic acid molecules and fusion proteins.

4 Claims, 14 Drawing Sheets

Specification includes a Sequence Listing.

(56) References Cited

OTHER PUBLICATIONS

Extended European Search Report (includes Supplementary European Search Report and Search Opinion) received for European Patent Application No. 12760251.4, dated Nov. 18, 2014, 7 pages.

Falco et al., (2007). "Zscan4: A Novel Gene Expressed Exclusively in Late 2-Cell Embryos and Embryonic Stem Cells," Developmental Biology, 307:539-550.

Feil et al., (1996). "Ligand-Activated Site-Specific Recombination in Mice," Proceedings of the National Academy of Sciences, 93:10887-10890.

GenBank accession No. EF587699.1, Available Online at <https://www.ncbi.nlm.nih.gov/nuccore/EF587699.1> Jul. 16, 2007, 2 pages.

Hirata et al., (2012). "Zscan4 Transiently Reactivates Early Embryonic Genes During the Generation of Induced Pluripotent Stem Cells," Science Reports, 2(208): 1-11.

International Preliminary Report on Patentability received for PCT Patent Application No. PCT/US2012/030005, dated Oct. 3, 2013, 8 pages.

International Search Report received for PCT Patent Application No. PCT/US2012/030005, dated Aug. 23, 2012, 6 pages.

International Written Opinion received for PCT Patent Application No. PCT/US2012/030005, dated Aug. 23, 2012, 6 pages.

Storm et al., (2007). "Regulation of Nanog Expression by Phosphoinositide 3-Kinase-dependent Signaling in Murine Embryonic Stem Cells," The Journal of Biological Chemistry, 282(9):6265-6273.

Williams et al., (1999). "The Zinc Finger-Associated SCAN Box Is a Conserved Oligomerization Domain," Molecular And Cellular Biology, 19(12):8526-8535.

Yang et al., (2010). "Stat3 Activation is Limiting for Reprogramming to Ground State Pluripotency Cell," Stem Cell, 7:319-328.

Zalzman et al., (2010). "Zscan4 Regulates Telomere Elongation and Genomic Stability in ES Cells," Nature, 464(7290):858-863.

* cited by examiner

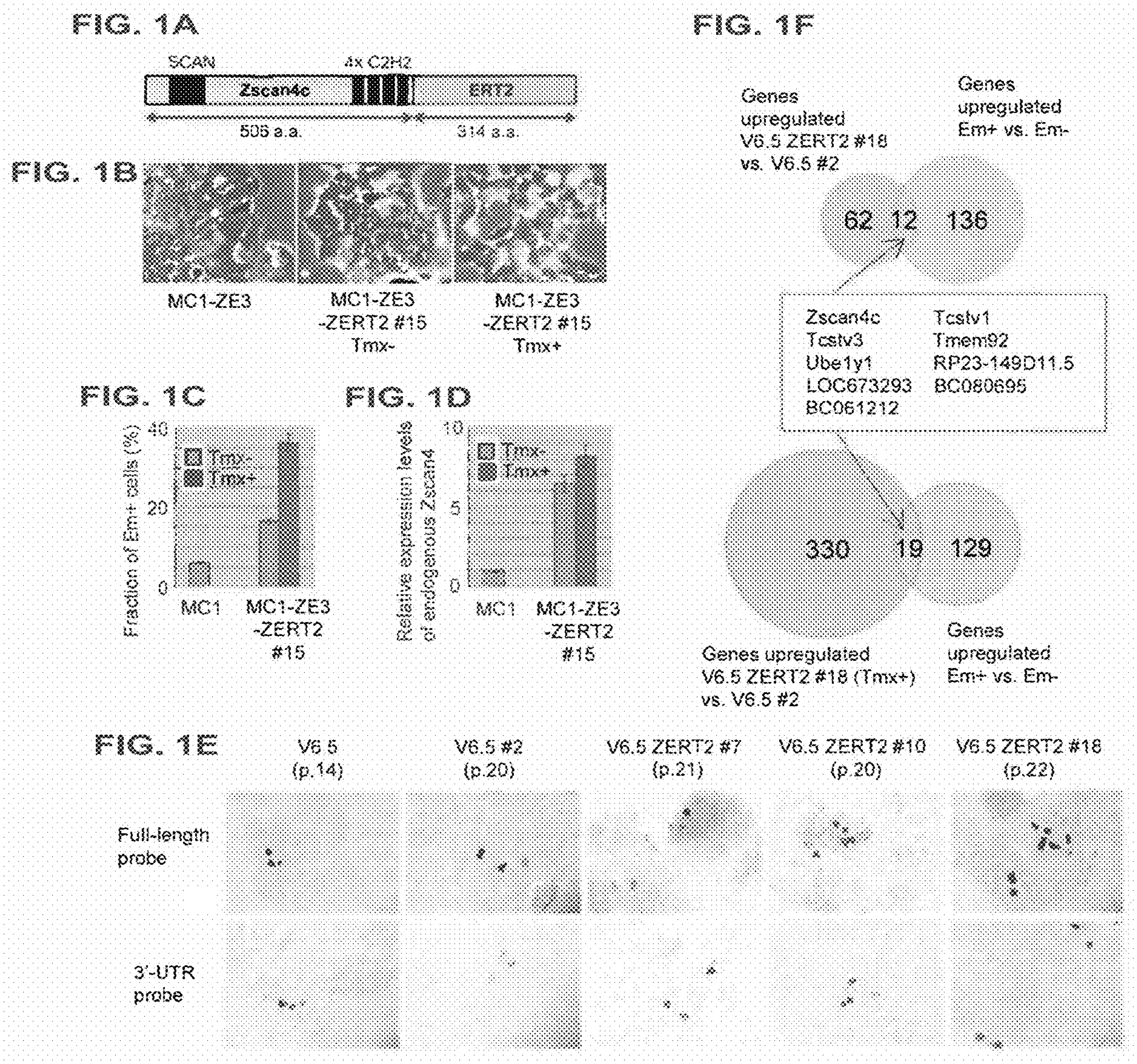
FIG. 1A
SCAN
4x C2H2
Zscan4c
ERT2
506 a.a.
314 a.a.
FIG. 1B
MC1-ZE3
MC1-ZE3 -ZERT2 #15 Tmx-
MC1-ZE3 -ZERT2 #15 Tmx+
FIG. 1C
Fraction of Em+ cells (%)
Tmx-
Tmx+
MC1
MC1-ZE3 -ZERT2 #15
FIG. 1D
Relative expression levels of endogenous Zscan4
Tmx-
Tmx+
MC1
MC1-ZE3 -ZERT2 #15
FIG. 1E
V6.5 (p.14)
V6.5 #2 (p.20)
V6.5 ZERT2 #7 (p.21)
V6.5 ZERT2 #10 (p.20)
V6.5 ZERT2 #18 (p.22)
Full-length probe
3'-UTR probe
FIG. 1F
Genes upregulated V6.5 ZERT2 #18 vs. V6.5 #2
Genes upregulated Em+ vs. Em-
62
12
136
Zscan4c
Tcstv1
Tcstv3
Tmem92
Ube1y1
RP23-149D11.5
LOC673293
BC080695
BC061212
330
19
129
Genes upregulated V6.5 ZERT2 #18 (Tmx+) vs. V6.5 #2
Genes upregulated Em+ vs. Em- ZDC-MC1-ZE16 clones, day3, passage 3 (Zscan4c-ΔC)

ZDN-MC1-ZE16 clones, day3, passage 3 (Zscan4c-ΔN)

FIG. 4A
| Cell line | Passage No. | No. injected ES cells per blastocyst | No. transferred blastocysts | No. embryos (%) E13.5-14.5 | No. embryos (%) E18.5 | No. live embryos (%) |
|---|---|---|---|---|---|---|
| V6.5 | 18 | 10-15 | 41 | 2 (5%) | | 1 (2%) |
| V6.5 ZERT2 #7 | 22 | 10-15 | 40 | 2 (5%) | | 1 (3%) |
| V6.5 ZERT2 #10 | 22 | 10-15 | 41 | 9 (22%) | | 9 (22%) |
| V6.5 ZERT2 #18 | 19 | 10-15 | 40 | 22 (55%) | | 17 (43%) |
| TA1 | 3 | 10-15 | 20 | 13 (65%) | | 12 (60%) |
| MC2 | 17 | 10-15 | 45 | 0 (0%) | | 0 (0%) |
| MC2 ZE #18 | 12-13 | 10-15 | 123 | 0 (0%) | | 0 (0%) |
| MC2 ZERT2 #6 | 18 | 10-15 | 48 | 3 (6%) | | 3 (6%) |
FIG. 4B
| Cell line | Passage No. | No. injected ES cells per blastocyst | No. transferred blastocysts | No. embryos (%) E13.5-14.5 | No. embryos (%) E18.5 | No. live embryos (%) |
|---|---|---|---|---|---|---|
| V6.5 | 18 | 1 | 71 | | 1 (1%) | 1 (1%) |
| V6.5 #2 | 21 | 1 | 77 | | 0 (0%) | 0 (0%) |
| V6.5 ZERT2 #18 | 21 | 1 | 44 | | 3 (7%) | 2 (5%) |
| TA1 | 4 | 1 | 79 | 3 (4%) | | 3 (4%) |
FIG. 4C
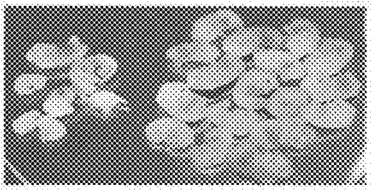
FIG. 4D
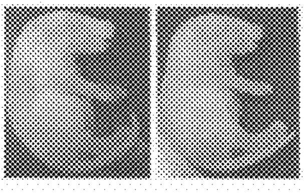
FIG. 4E
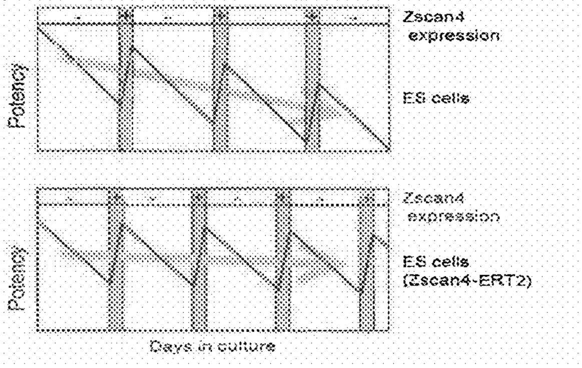

FIG. 5A

| Gene Symbol | Annotation | Fold Change |
|---|---|---|
| Tcstv3 | 2-cell-stage, variable group, member 3 | 107.8 |
| Zscan4c | zinc finger and SCAN domain containing 4C | 68.7 |
| Tmem92 | transmembrane protein 92 | 40.7 |
| A530040E14Rik | RIKEN cDNA A530040E14 gene | 39.7 |
| RP23-149D11.5 | novel protein similar to Prame proteins | 27.6 |
| LOC432715 | similar to GLE1 RNA export mediator-like (yeast | 26.2 |
| Arg2 | arginase type II | 24.9 |
| BC061212 | cDNA sequence BC061212 | 21.9 |
| Tcstv1 | 2-cell-stage, variable group, member 1 | 21.1 |
| AF067063 | cDNA sequence AF067063 | 20.7 |
| OTTMUSG00000001246 | predicted gene, OTTMUSG00000001246 | 19.3 |
| EG226955 | predicted gene, EG226955 | 19.2 |
| Lgals4 | lectin, galactose binding, soluble 4 | 16.2 |
| LOC434660 | | 16.1 |
| Eif1a | eukaryotic translation initiation factor 1A | 16.1 |
| Pif1 | PIF1 5'-to-3' DNA helicase homolog (S. cerevisiae) | 13.9 |
| LOC673293 | similar to Nuclear protein SkiP (Ski-interacting protein) (SNW1 protein) (Nuclear receptor coactivator NCoA-62) | 12.6 |
| LOC433231 | | 12.5 |
| OTTMUSG00000002043 | predicted gene, OTTMUSG00000002043 | 12.1 |
| 2310065F04Rik | RIKEN cDNA 2310065F04 gene | 10.5 |
| RP23-149D11.4 | hypothetical LOC381535 | 9.9 |
| C130092O11Rik | RIKEN cDNA C130092O11 gene | 9.6 |
| LOC671025 | similar to U2-associated SR140 protein | 9.3 |
| LOC385201 | similar to Spetex-2C protein | 9.3 |
| Ly6h | lymphocyte antigen 6 complex, locus H | 9.2 |
| LOC240895 | similar to SKI-interacting protein | 9.2 |
| EG668777 | predicted gene, EG668777 | 9.1 |
| Calcoco2 | calcium binding and coiled-coil domain 2 | 9.0 |
| XM_145358 | sequence XM_145358 | 9.0 |
| Myo3a | myosin IIIA | 8.4 |
| Hist1h4i | histone cluster 1, H4i | 8.1 |
| LOC669397 | similar to THO complex subunit 4 (Tho4) (RNA and export factor binding protein 1) (REF1-I) (Ally of AML-1 and LEF-1) (Aly/REF) | 8.1 |
| Rfxap | regulatory factor X-associated protein | 7.9 |
| LOC627530 | similar to THO complex subunit 4 (Tho4) (RNA and export factor binding protein 1) (REF1-I) (Ally of AML-1 and LEF-1) (Aly/REF) | 7.7 |
| EG666169 | predicted gene, EG666169 | 7.7 |
| Gm257 | gene model 257, (NCBI) | 7.4 |
| 1700066J24Rik | RIKEN cDNA 1700066J24 gene | 7.0 |
| Tbx3 | T-box 3 | 6.6 |
| Mgll | monoglyceride lipase | 6.5 |
| LOC226030 | similar to glyceraldehyde-3-phosphate dehydrogenase | 6.4 |
| Tspan1 | tetraspanin 1 | 6.3 |
| EG627488 | predicted gene, EG627488 | 6.1 |
| LOC625360 | similar to 2-cell-stage, variable group, member 3 | 6.0 |
| Rhox5 | reproductive homeobox 5 | 4.9 |
| EG666099 | predicted gene, EG666099 | 4.7 |
| LOC545920 | PREDICTED: Mus musculus similar to oocyte specific homeobox 3 (LOC545920), mRNA | 4.5 |
| EG666272 | predicted gene, EG666272 | 4.4 |
| Myl4 | myosin, light polypeptide 4 | 4.3 |
| C78283 | expressed sequence C78283 | 4.3 |

FIG. 5B

| | | |
|---|---|---|
| Sycp1 | synaptonemal complex protein 1 | 4.3 |
| D13Ertd608e | DNA segment, Chr 13, ERATO Doi 608, expressed | 4.2 |
| Pdlim3 | PDZ and LIM domain 3 | 4.1 |
| Hspa1a | heat shock protein 1A | 4.1 |
| EG624262 | predicted gene, EG624262 | 4.0 |
| Pdgfrl | platelet-derived growth factor receptor-like | 4.0 |
| Fer1l3 | fer-1-like 3, myoferlin (C. elegans) | 3.9 |
| Hist2h2aa1 | histone cluster 2, H2aa1 | 3.9 |
| Rpl39l | ribosomal protein L39-like | 3.7 |
| BC080695 | cDNA sequence BC080695 | 3.7 |
| Zfp352 | zinc finger protein 352 | 3.7 |
| 4631416L12Rik | RIKEN cDNA 4631416L12 gene | 3.6 |
| EG238217 | predicted gene, EG238217 | 3.4 |
| Hist1h2bc | histone cluster 1, H2bc | 3.4 |
| Gm428 | gene model 428, (NCBI) | 3.4 |
| Lonrf3 | LON peptidase N-terminal domain and ring finger 3 | 3.3 |
| Lmx1a | LIM homeobox transcription factor 1 alpha | 3.3 |
| LOC619649 | similar to transcription elongation factor B polypeptide 3 binding protein 1 isoform 1 | 3.2 |
| 1810062G17Rik | RIKEN cDNA 1810062G17 gene | 3.2 |
| Defcr3 | defensin related cryptdin 3 | 3.2 |
| LOC666185 | similar to CG32602-PA | 3.2 |
| Sord | sorbitol dehydrogenase | 3.1 |
| EG434050 | predicted gene, EG434050 | 3.1 |
| Hist1h1c | histone cluster 1, H1c | 3.1 |
| D1pas1 | | 3.1 |
| Defcr6 | defensin related cryptdin 6 | 3.1 |
| Slc4a5 | solute carrier family 4, sodium bicarbonate cotransporter, member 5 | 3.0 |
| Neto2 | neuropilin (NRP) and tolloid (TLL)-like 2 | 3.0 |
| Mael | maelstrom homolog (Drosophila) | 3.0 |
| Terc | telomerase RNA component | 3.0 |
| Avpi1 | arginine vasopressin-induced 1 | 3.0 |
| Zcchc17 | zinc finger, CCHC domain containing 17 | 3.0 |
| Hspa1b | heat shock protein 1B | 3.0 |
| 1700123J19Rik | RIKEN cDNA 1700123J19 gene | 2.9 |
| LOC380994 | similar to Sycp3 like Y-linked | 2.9 |
| Thnsl2 | threonine synthase-like 2 (bacterial) | 2.8 |
| LOC673656 | hypothetical protein LOC673656 | 2.8 |
| Cidea | cell death-inducing DNA fragmentation factor, alpha subunit-like effector A | 2.8 |
| Vstm2b | V-set and transmembrane domain containing 2B | 2.8 |
| Jam2 | junction adhesion molecule 2 | 2.8 |
| Tuba3a | tubulin, alpha 3A | 2.7 |
| Rhox2a | reproductive homeobox 2A | 2.7 |
| Spic | Spi-C transcription factor (Spi-1/PU.1 related) | 2.7 |
| Xlr4b | X-linked lymphocyte-regulated 4B | 2.7 |
| EG665954 | predicted gene, EG665954 | 2.6 |
| Abcb5 | ATP-binding cassette, sub-family B (MDR/TAP), member 5 | 2.6 |
| Lonp2 | lon peptidase 2, peroxisomal | 2.6 |
| LOC623166 | | 2.5 |
| Kctd8 | potassium channel tetramerisation domain containing 8 | 2.5 |
| Ankrd22 | ankyrin repeat domain 22 | 2.5 |

FIG. 5C

| | | |
|---|---|---|
| Defcr23 | defensin related cryptdin 23 | 2.5 |
| Ccl3 | chemokine (C-C motif) ligand 3 | 2.5 |
| 1700052K11Rik | RIKEN cDNA 1700052K11 gene | 2.5 |
| Mylpf | myosin light chain, phosphorylatable, fast skeletal muscle | 2.5 |
| Ak7 | adenylate kinase 7 | 2.5 |
| Cdc42ep3 | CDC42 effector protein (Rho GTPase binding) 3 | 2.5 |
| Ube1y1 | ubiquitin-activating enzyme E1, Chr Y 1 | 2.5 |
| Cacna1s | calcium channel, voltage-dependent, L type, alpha 1S subunit | 2.5 |
| B020006M18Rik | RIKEN cDNA B020006M18 gene | 2.4 |
| Zfp296 | zinc finger protein 296 | 2.3 |
| LOC244061 | similar to Smad nuclear interacting protein 1 | 2.3 |
| Mlana | melan-A | 2.3 |
| Defa1 | defensin, alpha 1 | 2.3 |
| EG229571 | predicted gene, EG229571 | 2.3 |
| Gm5 | gene model 5, (NCBI) | 2.3 |
| Arl4d | ADP-ribosylation factor-like 4D | 2.3 |
| Myh13 | myosin, heavy polypeptide 13, skeletal muscle | 2.3 |
| Hormad1 | HORMA domain containing 1 | 2.3 |
| Myh4 | myosin, heavy polypeptide 4, skeletal muscle | 2.3 |
| Syce1 | synaptonemal complex central element protein 1 | 2.3 |
| Prkch | protein kinase C, eta | 2.2 |
| Pramel3 | preferentially expressed antigen in melanoma-like 3 | 2.2 |
| Glrx2 | glutaredoxin 2 (thioltransferase) | 2.2 |
| EG620899 | predicted gene, EG620899 | 2.2 |
| LOC675962 | similar to TD and POZ domain containing 5 | 2.2 |
| Tigd2 | tigger transposable element derived 2 | 2.2 |
| Phf11 | PHD finger protein 11 | 2.2 |
| Gabarapl2 | gamma-aminobutyric acid (GABA-A) receptor-associated protein-like 2 | 2.2 |
| Gsta3 | glutathione S-transferase, alpha 3 | 2.2 |
| LOC385262 | | 2.1 |
| BC003993 | cDNA sequence BC003993 | 2.1 |
| Tdpoz4 | TD and POZ domain containing 4 | 2.1 |
| Taf7l | TAF7-like RNA polymerase II, TATA box binding protein (TBP)-associated factor | 2.1 |
| Isoc2b | isochorismatase domain containing 2b | 2.1 |
| Zfp371 | zinc finger protein 371 | 2.1 |
| 8030474K03Rik | RIKEN cDNA 8030474K03 gene | 2.1 |
| Sycp2 | synaptonemal complex protein 2 | 2.1 |
| Gm1568 | gene model 1568, (NCBI) | 2.1 |
| Stox1 | storkhead box 1 | 2.1 |
| Defcr24 | defensin related cryptdin 24 | 2.1 |
| Arih2 | ariadne homolog 2 (Drosophila) | 2.1 |
| Serpinb1b | serine (or cysteine) peptidase inhibitor, clade B, member 1b | 2.0 |
| Sp110 | Sp110 nuclear body protein | 2.0 |
| Mreg | melanoregulin | 2.0 |
| Acp6 | acid phosphatase 6, lysophosphatidic | 2.0 |
| Morc1 | microrchidia 1 | 2.0 |
| EG666692 | predicted gene, EG666692 | 2.0 |
| EG666675 | predicted gene, EG666675 | 2.0 |
| Bdnf | brain derived neurotrophic factor | 2.0 |

Tmx⁻ (day 30) Tmx⁺ (day 30)

[FDR<0.05, Fold-change>2]

FIG. 8

| Gene Symbol | Annotation | Fold Change |
|---|---|---|
| Rian | RNA imprinted and accumulated in nucleus | 191.7 |
| Eif2s3y | eukaryotic translation initiation factor 2, subunit 3, structural gene Y-linked | 113.9 |
| Uty | ubiquitously transcribed tetratricopeptide repeat gene, Y chromosome | 99.9 |
| Mirg | miRNA containing gene | 92.1 |
| B830012L14Rik | RIKEN cDNA B830012L14 gene | 64.1 |
| Meg3 | maternally expressed 3 | 44.5 |
| Ddx3y | DEAD (Asp-Glu-Ala-Asp) box polypeptide 3, Y-linked | 33.5 |
| 6430411K18Rik | RIKEN cDNA 6430411K18 gene | 12.9 |
| Ube1y1 | ubiquitin-activating enzyme E1, Chr Y 1 | 10.3 |
| Cubn | cubilin (intrinsic factor-cobalamin receptor) | 4.6 |
| Peg13 | paternally expressed 13 | 3.7 |
| Tmem92 | transmembrane protein 92 | 3.7 |
| Zscan4c | zinc finger and SCAN domain containing 4C | 3.6 |
| BC080695 | cDNA sequence BC080695 | 3.1 |
| Ntrk2 | neurotrophic tyrosine kinase, receptor, type 2 | 2.9 |
| Spon1 | spondin 1, (f-spondin) extracellular matrix protein | 2.9 |
| AF067061 | cDNA sequence AF067061 | 2.9 |
| B020031M17Rik | RIKEN cDNA B020031M17 gene | 2.8 |
| Tcstv3 | 2-cell-stage, variable group, member 3 | 2.8 |
| Rxrg | retinoid X receptor gamma | 2.8 |
| Aadat | aminoadipate aminotransferase | 2.7 |
| Tnrc4 | trinucleotide repeat containing 4 | 2.7 |
| OTTMUSG00000010537 | predicted gene, OTTMUSG00000010537 | 2.7 |
| Ebf1 | early B-cell factor 1 | 2.6 |
| Defb30 | defensin beta 30 | 2.6 |
| C130034I18Rik | RIKEN cDNA C130034I18 gene | 2.6 |
| Nudt12 | nudix (nucleoside diphosphate linked moiety X)-type motif 12 | 2.5 |
| Dnajb13 | DnaJ (Hsp40) related, subfamily B, member 13 | 2.5 |
| Tnfrsf17 | tumor necrosis factor receptor superfamily, member 17 | 2.5 |
| Gm428 | gene model 428, (NCBI) | 2.5 |
| BC061212 | cDNA sequence BC061212 | 2.5 |
| Zbp1 | Z-DNA binding protein 1 | 2.5 |
| Galnt6 | UDP-N-acetyl-alpha-D-galactosamine:polypeptide N-acetylgalactosaminyltransferase 6 | 2.4 |
| Syt4 | synaptotagmin IV | 2.4 |
| Adm | adrenomedullin | 2.4 |
| Krt12 | keratin 12 | 2.4 |
| Zfp264 | zinc finger protein 264 | 2.4 |
| OTTMUSG00000001246 | predicted gene, OTTMUSG00000001246 | 2.4 |
| 1700066J24Rik | RIKEN cDNA 1700066J24 gene | 2.3 |
| Gfra1 | glial cell line derived neurotrophic factor family receptor alpha 1 | 2.3 |
| Spaca1 | sperm acrosome associated 1 | 2.3 |
| Krt9 | keratin 9 | 2.3 |
| Saa2 | serum amyloid A 2 | 2.3 |
| Tff3 | trefoil factor 3, intestinal | 2.2 |
| 4930599N23Rik | RIKEN cDNA 4930599N23 gene | 2.2 |
| Tcstv1 | 2-cell-stage, variable group, member 1 | 2.2 |
| LOC673293 | similar to Nuclear protein SkiP (Ski-interacting protein) (SNW1 protein) (Nuclear receptor co | 2.2 |
| 2410004A20Rik | RIKEN cDNA 2410004A20 gene | 2.2 |
| Rasd1 | RAS, dexamethasone-induced 1 | 2.2 |
| Ushbp1 | Usher syndrome 1C binding protein 1 | 2.2 |

FIG. 9

| Symbol | Annotation | Fold Change |
|---|---|---|
| Rian | RNA imprinted and accumulated in nucleus | 154.8 |
| Eif2s3y | eukaryotic translation initiation factor 2, subunit 3, structural gene Y-linked | 105.9 |
| Uty | ubiquitously transcribed tetratricopeptide repeat gene, Y chromosome | 96.2 |
| Mirg | miRNA containing gene | 84.2 |
| B830012L14Rik | RIKEN cDNA B830012L14 gene | 54.7 |
| Meg3 | maternally expressed 3 | 40.8 |
| Ddx3y | DEAD (Asp-Glu-Ala-Asp) box polypeptide 3, Y-linked | 32.7 |
| Ube1y1 | ubiquitin-activating enzyme E1, Chr Y 1 | 14.0 |
| 6430411K18Rik | RIKEN cDNA 6430411K18 gene | 10.6 |
| Zbp1 | Z-DNA binding protein 1 | 7.8 |
| Clca3 | chloride channel calcium activated 3 | 6.1 |
| Cldn10 | claudin 10 | 5.9 |
| Heph | hephaestin | 5.7 |
| 1700013H16Rik | RIKEN cDNA 1700013H16 gene | 5.7 |
| Tmem92 | transmembrane protein 92 | 5.6 |
| Pof1b | premature ovarian failure 1B | 5.5 |
| Gpm6a | glycoprotein m6a | 5.2 |
| Zscan4c | zinc finger and SCAN domain containing 4C | 5.1 |
| BC080695 | cDNA sequence BC080695 | 5.0 |
| Fbxw16 | F-box and WD-40 domain protein 16 | 4.9 |
| Pdzrn3 | PDZ domain containing RING finger 3 | 4.8 |
| Indo | indoleamine-pyrrole 2,3 dioxygenase | 4.8 |
| Fgf10 | fibroblast growth factor 10 | 4.8 |
| Ccrl1 | chemokine (C-C motif) receptor-like 1 | 4.8 |
| 4931407G18Rik | RIKEN cDNA 4931407G18 gene | 4.7 |
| Arg2 | arginase type II | 4.7 |
| Cftr | cystic fibrosis transmembrane conductance regulator homolog | 4.6 |
| Atoh1 | atonal homolog 1 (Drosophila) | 4.6 |
| Rgn | regucalcin | 4.6 |
| OTTMUSG00000010537 | predicted gene, OTTMUSG00000010537 | 4.5 |
| Kctd12b | potassium channel tetramerisation domain containing 12b | 4.5 |
| Gfra1 | glial cell line derived neurotrophic factor family receptor alpha 1 | 4.5 |
| Pdzrn4 | PDZ domain containing RING finger 4 | 4.4 |
| Cyp2j9 | cytochrome P450, family 2, subfamily j, polypeptide 9 | 4.4 |
| Calcr | calcitonin receptor | 4.4 |
| Cttnbp2 | cortactin binding protein 2 | 4.4 |
| AF067061 | cDNA sequence AF067061 | 4.3 |
| Pramel6 | preferentially expressed antigen in melanoma like 6 | 4.2 |
| Aadac | arylacetamide deacetylase (esterase) | 4.1 |
| Spic | Spi-C transcription factor (Spi-1/PU.1 related) | 4.1 |
| Lrrk2 | leucine-rich repeat kinase 2 | 4.1 |
| Dll4 | delta-like 4 (Drosophila) | 4.1 |
| Tmem140 | transmembrane protein 140 | 4.1 |
| B020031M17Rik | RIKEN cDNA B020031M17 gene | 4.0 |
| Tcstv3 | 2-cell-stage, variable group, member 3 | 4.0 |
| Snph | syntaphilin | 4.0 |
| Akr1c18 | aldo-keto reductase family 1, member C18 | 4.0 |
| 1110018M03Rik | RIKEN cDNA 1110018M03 gene | 3.9 |
| Lancl3 | LanC lantibiotic synthetase component C-like 3 (bacterial) | 3.9 |
| Trpa1 | transient receptor potential cation channel, subfamily A, member 1 | 3.7 |

FIG. 10A

| ID | Attached (day2-3) | Outgrowth (day5-7) | Status of outgrowth * | 1st picked up (day6-8) | ES-like colonies (day10-14) | ES line (day20) |
|---|---|---|---|---|---|---|
| 1 | o | o | U | o | o | o |
| 2 | o | o | D | x | - | - |
| 3 | o | o | U | o | o | o |
| 4 | o | o | U/D | o | o | o |
| 5 | o | o | D | x | - | - |
| 6 | o | o | D | x | - | - |
| 7 | o | o | U/D | o | o | o |
| 8 | o | o | U/D | o | o | o |
| 9 | o | o | D | x | - | - |
| 10 | o | o | U | o | o | o |
| 11 | o | o | U/D | o | o | o |
| 12 | o | o | U | o | o | o |
| 13 | o | o | D | x | - | - |
| 14 | o | o | U/D | o | o | o |
| 15 | o | o | U | o | o | o |
| 16 | o | o | U | o | o | o |
| 17 | x | x | - | - | - | - |
| 18 | o | o | U/D | o | o | o |
| 19 | o | o | D | x | - | - |
| 20 | o | o | U | o | o | o |

FIG. 10b

| No. Blastocysts used | No. blastocysts attached (%) | No. Outgrowth (%) | No. ES-like colonies (%) | No. ES cell lines established |
|---|---|---|---|---|
| 20 | 19 (95%) | 19 (95%) | 13 (68%) | 13 (68%) |

| Cell line tested | No. 4N blastocysts injected | No. Implantation (%) | No. ES-derived fetus at E13.5 (%) | No. Live embryos (%) | Sex of embryos |
|---|---|---|---|---|---|
| #1 | 36 | 21 (58%) | 11 (31%) | 10 (28%) | M |
| #3 | 24 | 19 (79%) | 11 (46%) | 10 (42%) | M |
| #10 | 20 | 16 (80%) | 13 (65%) | 12 (60%) | M |
| #15 | 27 | 24 (89%) | 4 (15%) | 4 (15%) | F |
| #16 | 20 | 18 (90%) | 11 (55%) | 10 (50%) | M |
| #20 | 20 | 17 (85%) | 11 (55%) | 10 (50%) | M |

SEQUENCE LISTING

<160> NUMBER OF SEQ ID NOS: 25

<210> SEQ ID NO 1
<211> LENGTH: 2230
<212> TYPE: DNA
<213> ORGANISM: Homo sapiens

<400> SEQUENCE: 1
ccttgtaatt cataaatctc tgaaaactta aaagtttgag caaaagtttg tcatgtttct 60
atgagtaatt tataataaaa cttgatcaga atttgtgaga ctagcgtttg tctttatatt 120
ttcctttttt tttttttttt tttgagacac agtctcgctc tgtcgtccag gctggagtgc 180
cgtggcgtaa tctcggctca ctgcaacctc tgcctcctgg attcaaacaa ttcttctgcc 240
tcagcctcct gagtagctgg gattacagga ccagtgatgg tatagaacac tgtattagag 300
acatggagct ggggctggat gaagattcca tcagtaattc aatcaacaga caagtgttat 360
ccaatcacgt ctttaaatca atcactgaca tggagctggg gctggatgaa gattccatca 420
gtaattcaat caacagacaa gtgttatcca atcacgtctt taaatcaatc actgatccca 480
gcccctataa aagggagcag ccttaggagg cacatcagat aaacccagtg tggaaagcta 540
gtcacacatc agctcagtgt tcggcccggg attacccagt caaccaagga gcttgcagtt 600
ttaaagaatc caccaactgt tgaaacaaat ccctagagac acaaggcaag agactgaatc 660
atcaaagtaa agtctctctg agaattattg ctaagaatgg ctttagatct aagaaccata 720
tttcagtgtg aaccatccga gaataatctt ggatcagaaa attcagcgtt tcaacaaagc 780
caaggacctg ctgttcagag agaagaaggg atttctgagt tctcaagaat ggtgctcaat 840
tcatttcaag acagcaataa ttcatatgca aggcaggaat tgcaaagact ttataggatc 900
tttcactcat ggctgcaacc agaaaagcac agcaaggatg aaattatttc tctattagtc 960
ctggagcagt ttatgattgg tggccactgc aatgacaaag ccagtgtgaa agagaaatgg 1020
aaatcaagtg gcaaaaactt ggagagattc atagaagacc tgactgatga cagcataaat 1080
ccacctgcct tagtccacgt ccacatgcag ggacaggaag ctctcttttc tgaggatatg 1140
cccttaagag atgtcattgt tcatctcaca aaacaagtga atgcccaaac cacaagagaa 1200
gcaaacatgg ggacaccctc ccagacttcc caagatactt ccttagaaac aggacaagga 1260
tatgaagatg aacaagatgg ctggaacagt tcttcgaaaa ctactcgagt aaatgaaaat 1320
attactaatc aaggcaatca aatagtttcc ctaatcatca tccaggaaga gaacggtcct 1380
aggcctgaag agggaggtgt ttcttctgac aacccataca actcaaaaag agcagagcta 1440
gtcactgcta gatctcagga agggtccata aatggaatca ctttccaagg tgtccctatg 1500
gtgatgggag cagggtgtat ctctcaacca gagcagtcct cccctgagtc tgcccttacc 1560
caccagagca atgagggaaa ttccacatgt gaggtacatc agaaaggatc ccatggagtc 1620
caaaaatcat acaaatgtga agaatgcccc aaggtcttta agtatctctg tcacttatta 1680
gctcaccaga gaagacacag gaatgagagg ccatttgttt gtcccgagtg tcaaaaaggc 1740
ttcttccaga tatcagacct acgggtgcat cagataattc acacaggaaa gaagcctttc 1800
acatgcagca tgtgtaaaaa gtccttcagc cacaaaacca acctgcggtc tcatgagaga 1860
atccacacag gagaaaagcc ttatacatgt cccttttgta agacaagcta ccgccagtca 1920
tccacatacc accgccatat gaggactcat gagaaaatta ccctgccaag tgttccctcc 1980
acaccagaag cttcctaagc tgctggtctg ataatgtgta taaatatgta tgcaagtatg 2040
tatattccta tagtatttat ctacttagga tataagatat aatctcctga ttatgctttc 2100

```
aatttattgt cttgcttcat taaaatgtaa ggctaaggag agcatggaat ttgtcagttt   2160

tgttcactaa agtattccaa gtggttggga aagtggaaca tttccaagaa ccaataaatt   2220

tctgttgaat                                                          2230


<210> SEQ ID NO 2
<211> LENGTH: 433
<212> TYPE: PRT
<213> ORGANISM: Homo sapiens
<220> FEATURE:
<221> NAME/KEY: DOMAIN
<222> LOCATION: (44)..(126)
<223> OTHER INFORMATION: SCAN box
<220> FEATURE:
<221> NAME/KEY: DOMAIN
<222> LOCATION: (312)..(334)
<223> OTHER INFORMATION: C2H2-type 1
<220> FEATURE:
<221> NAME/KEY: DOMAIN
<222> LOCATION: (340)..(362)
<223> OTHER INFORMATION: C2H2-type 2
<220> FEATURE:
<221> NAME/KEY: DOMAIN
<222> LOCATION: (368)..(390)
<223> OTHER INFORMATION: C2H2-type 3
<220> FEATURE:
<221> NAME/KEY: DOMAIN
<222> LOCATION: (396)..(418)
<223> OTHER INFORMATION: C2H2-type 4

<400> SEQUENCE: 2

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Ser Val Lys Glu Lys Trp Lys Ser Ser Gly
            100                 105                 110

Lys Asn Leu Glu Arg Phe Ile Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Ser Lys Thr Thr Arg Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Pro Glu Glu Gly Gly Val Ser Ser Asp Asn Pro
225                 230                 235                 240
```

-continued

```
Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

Ser His Gly Val Gln Lys Ser Tyr Lys Cys Glu Glu Cys Pro Lys Val
305                 310                 315                 320

Phe Lys Tyr Leu Cys His Leu Leu Ala His Gln Arg Arg His Arg Asn
                325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
        355                 360                 365

Thr Cys Ser Met Cys Lys Lys Ser Phe Ser His Lys Thr Asn Leu Arg
    370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
            420                 425                 430

Ser


<210> SEQ ID NO 3
<211> LENGTH: 2275
<212> TYPE: DNA
<213> ORGANISM: Mus musculus

<400> SEQUENCE: 3

cacagtgcct ccctgggctt cttggcatca cccttgaagt tcactggaga aagagttgag      60

gtggaggaat aggtaaactt cccttcctag tggtcttgaa tgtcttttac agtacatcca     120

tcaactgtta gcattttcgt aaagtcacaa aacagatatt aaactactat agttgaatct     180

ttcacaccat tgtcaccaca atggcttcac agcaggcacc agcaaaagac cttcagacca     240

acaatttaga gtttactcca actgatagtt ctggtgtgca gtgggcagaa gacatctcta     300

actcaccaag tgctcagcta aacttttccc caagtaacaa tggctgctgg gcaactcagg     360

agctgcaaag tctctggaag atgttcaact cctggttgca gccagaaaag cagactaagg     420

agcagatgat ttctcaactg gtcttggagc agtttctcct cactgggcac tgcaaggaca     480

agtatgcttt gacagagaag tggaaagcca gtggtagcga tatgaggaga ttcatggaga     540

gtctgactga tgagtgcttg aagcctcctg tcatggtcca tgtctcaatg caaggacaag     600

aagccctctt ttctgaaaac atgccattaa aagaagtcat caagcttttg aaacaacagc     660

aatctgcaac aaggccaaca ccagataatg cacagatgcc agtagacacc acacaagata     720

gattattggc cacaggacaa gaaaacagtg aaaatgaatg caacacctct tgtaatgcta     780

ctgaaggaaa tgttggtgag agctgtagtg gaaatgaaat ggactcctct cttattatcc     840

agaaagaaca gtaccctgag catgaagagg ggaatgttgt ttgtcaattc cctcttgatg     900

ccagaagagc aagtcaaggc acctccagtc atcatgtaga cttcctgagt gctctgacta     960
```

-continued

```
ctgccgatgt ccccatggag gaacaaccaa aggatttatc cagagaaaac atctctgagg   1020
acaagaacaa ttgctataac acttccagga atgcagctac taaagtatat agtggtgata   1080
atattcccag gaaaaagaca gactcccttt ccattaacaa gaggatatat catcctgagc   1140
ctgaggtggg agatattcct tatggagttc ctcaggattc tacaagagca agtcaaggaa   1200
catctacatg cctgcaagag tcacttgggg gatgtttttc cgaaaaagac cctagggagg   1260
taccagggtt gcagtctagg taagagcagc ctatctctga tcctgtcctt cttggtaaga   1320
atcatgaggc aaacttacca tgtgaaagtc atcaaaagag attctgtaga gatgccaaac   1380
tatacaagtg tgaagaatgt tctaggatgt tcaaacatgc caggagcctt tcatcccacc   1440
agagaactca cctgaataag aagagtgaat tgctttgtgt cacctgtcag aaaattttca   1500
aacgagtctc tgaccgccga acccatgaga tcatacacat gccagaaaag cctttcaagt   1560
gcagcacatg tgaaaagtcc ttcagccaca agaccaacct gaagtctcat gagatgattc   1620
acacaggaga aatgccttat gtctgttccc tatgtagccg tcgctttcgc caatcatcca   1680
cttaccatcg tcacctgagg aattatcaca gatctgactg aagtatctaa catcctcagc   1740
agagactggt agggcttcag cctcagtatg tcatcttcaa agagagaaga atgttgcaag   1800
taaattgtac tgtcccaata atgatataac atgcttgtgg attgccactt ttatgttttg   1860
ttttgttttg tttttatttt tgtgtgtgtg tatgtaattt tttgtctgta tttccatagt   1920
tccacagcat aagttattag aatactttgc tgttaattct tgagttgctt cttgctttta   1980
gacagtgtct ttctggttgg cagctttata cacctgtctt tctggcacta gagtttccaa   2040
acattttctg atctccactt ttattttcta cagtggtcct gacagaggcc tgccattccc   2100
tctgacattt ttctacatgt tggggtttca tcccaagtct tagggttgca agttaaatgc   2160
attgcctctt cagacatctc atgtcatgtc tactgcttac agttcaagaa tatttctcta   2220
cattactaga acgacgttca aagtggaata ataaataaat aaataatcaa caatt        2275
```

```
<210> SEQ ID NO 4
<211> LENGTH: 360
<212> TYPE: PRT
<213> ORGANISM: Mus musculus

<400> SEQUENCE: 4

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140
```

-continued

```
Glu Val Ile Lys Leu Leu Lys Gln Gln Gln Ser Ala Thr Arg Pro Thr
145                 150                 155                 160

Pro Asp Asn Ala Gln Met Pro Val Asp Thr Thr Gln Asp Arg Leu Leu
                165                 170                 175

Ala Thr Gly Gln Glu Asn Ser Glu Asn Glu Cys Asn Thr Ser Cys Asn
            180                 185                 190

Ala Thr Glu Gly Asn Val Gly Glu Ser Cys Ser Gly Asn Glu Met Asp
        195                 200                 205

Ser Ser Leu Ile Ile Gln Lys Glu Gln Tyr Pro Glu His Glu Glu Gly
    210                 215                 220

Asn Val Val Cys Gln Phe Pro Leu Asp Ala Arg Arg Ala Ser Gln Gly
225                 230                 235                 240

Thr Ser Ser His His Val Asp Phe Leu Ser Ala Leu Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Lys
        275                 280                 285

Val Tyr Ser Gly Asp Asn Ile Pro Arg Lys Lys Thr Asp Ser Leu Ser
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Gly Cys Phe Ser Glu Lys Asp Pro Arg
            340                 345                 350

Glu Val Pro Gly Leu Gln Ser Arg
        355                 360
```

<210> SEQ ID NO 5
<211> LENGTH: 1774
<212> TYPE: DNA
<213> ORGANISM: Mus musculus

<400> SEQUENCE: 5

```
cacagtgcct ccctgggctt cttggcatca cccttgaagt tcactggaga aagaggtgat      60

gtggagaagt aggtaaactt ccctttcttg tggtcttgaa tgtcttttac agtacatccg     120

tcaactgtta gcattttcct aaagtcacaa aacagatact aaactgctat agttgaatct     180

ttcagaccat tgtcaccaca atggcttcac agcaggcacc agcaaaagac cttcagacca     240

acaatttaga gtttactcca actgatagtt ctggtgtgca gtgggcagaa gacatctcta     300

actcaccaag tgctcagcta aacttttccc caagtaacaa tggctgctgg gcaactcagg     360

agctgcaaag tctctggaag atgttcaact cctggttgca gccagaaaag cagactaagg     420

agcagatgat ttctcaattg gtcttggagc agtttctcct cactgggcac tgcaaggaca     480

agtatgcttt gacagagaag tggaaagcca gtggtagcga tatgaggaga ttcatggaga     540

gtctgactga tgagtgcttg aagcctcctg tcatggtcca tgtttcaatg caaggacaag     600

aagccctctt ttctgaaaac atgccattaa aagaagtcat caagcttttg aaacaacagc     660

aatctgcaac aaggccaata ccagataatg cacagatgcc agtagacacc acacaagata     720

gattattggc cacaggcaag aaaacagtga aaatgaatgc aacacctctt gcaatgctac     780

tgaagtaaat gttggtgaaa gctgtagtgg aaatgaaaag gactcccttc ttattaccca     840

gaaagaacaa aaccatgagc atgaagaggg gaatgttgtt tgtcaattcc ctcgtggtgc     900
```

-continued

```
cagaagagca agtcaagaca cctccagtca tcatgtagac ttcccgagtg ctctgactcc    960

tgcagatgtc cccatggagg aacaaccaat ggatttatcc agagaaaaca tctctgagga   1020

caagaacaat tgctataaca cttccaggaa tgcagctact caagtatata gtggtgataa   1080

tattcccagg aacaagacag actccctttt cattaacaag agaatatatc atcctgagcc   1140

tgaggtggga gatattcctt atggagttcc tcaggattct acaagagcaa gtcaaggaac   1200

atctacatgc ctgcaagagt cacttgggga atgtttttct gaaaaagacc caagggaggt   1260

accagggttg cagtctaggc aagagcagcc tatctctgat cctgtccttg gtaagaatca   1320

tgaggcaaac ttaccatgtg aaagtcatca aaagagattc catagagatg ccaaactata   1380

caagtgtgaa gaatgttcta ggatgttcaa acatgccagg agcctttcat cccaccagag   1440

aactcacctg aataagaaga gtgaattgct ttgcatcacc tgtcagaaaa tattcaaacg   1500

agtttctgac cttcgaaccc atgagatcat acacatgtca gaaaagcctt tcaagtgcag   1560

cacatgtgaa aagtccttca gccacaagac caacctgaag tatcatgaga tgattcacac   1620

aggagaaatg ccttatgtct gttccctatg tagccgtcgc tttcgccaat catccactta   1680

ccatcgtcac ctgaggaatt accacagatc tgactgaagt atctaacatc ctcagcagag   1740

actggtaggg cttcagcctc agtatgtcat cttc                               1774
```

```
<210> SEQ ID NO 6
<211> LENGTH: 195
<212> TYPE: PRT
<213> ORGANISM: Mus musculus

<400> SEQUENCE: 6

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Ala Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 7
<211> LENGTH: 2275
<212> TYPE: DNA
<213> ORGANISM: Mus musculus

<400> SEQUENCE: 7

```
cacagtgcct ccctgggctt cttggcatca cccttgaagt tcaccggaga aagcagtgag     60

gtggaggaat aggtaaactt tccttcctag tggtcttgaa tgtcttttac agtacatcca    120

tcaactgtta gcattttcgt aaagtcacaa aacagatatt aaactactat agttgaatct    180

ttcacaccat tgtcaccaca atggcttcac agcaggcacc agcaaaagac cttcagacca    240

acaatttaga gtttactcca actgatagtt ctggtgtgca gtgggcagaa gacatctcta    300

actcaccaag tgctcagcta aacttttccc caagtaacaa tggctgctgg gcaactcagg    360

agctgcaaag tctctggaag atgttcaact cctggttgca gccagaaaag cagactaagg    420

agcagatgat ttctcaactg gtcttggagc agtttctcct cactgggcac tgcaaggaca    480

agtatgcttt gacagagaag tggaaagcca gtggtagcga tatgaggaga ttcatggaga    540

gtctgactga tgagtgcttg aagcctcctg tcatggtcca tgtttcaatg caaggacaag    600

aagccctctt ttctgaaaac atgccattaa aagaagtcat caagcttttg aaacaacagc    660

aatctgcaac aaggccaaca ccagataatg agcagatgcc agtagacacc acacaagata    720

gattattggc cacaggacaa gaaaacagtg aaaatgaatg caacaactct tgtaatgcta    780

ctgaagcaaa tgttggtgaa agctgtagtg gaaatgaaat ggactccctt cttattatcc    840

agaaagaaca gcaccctgag catgaagagg ggaatgttgt ttgtcaattc cctcatggtg    900

ccagaagagc aagtcaaggc acccccagtc atcatgtaga cttcccgagt gctccgacta    960

ctgccgatgt ccccatggag gaacaaccaa aggatttatc cagagaaaac atctctgagg   1020

acaagaacaa ttgctataac acttccagaa atgcagctac tcaagtatat agtggtgata   1080

atattcccag gaacaagtca gactcccttt tcattaacaa gagaatatat catcctgagc   1140

ctgaggtggg agatattcct tatggagttc ctcaggattc tacaagagca agtcaaggaa   1200

catctacatg cctgcaagag tcacttgggg aatgtttttc tgaaaacgac ccaagggagg   1260

taccagggtt gcagtctagg caagagcagc ctatctctga tcctgtcctt cttggtaaga   1320

atcatgaggc aaacttacca tgtgaaagtc atcaaaagag attctgtaga gatgccaaac   1380

tatacaagtg tgaagaatgt tctaggatgt tcaaacatgc caggagcctt tcatcccacc   1440

agagaactca cctgaataag aagagtgaat tgctttgtgt cacctgtcag aaaatgttca   1500

aacgagtctc tgaccgccga acccatgaga tcatacacat gccagaaaag cctttcaagt   1560

gcagcacatg tgaaaagtcc ttcagccaca agaccaacct gaagtctcat gagatgattc   1620

acacaggaga aatgccttat gtctgttccc tatgtagccg tcgctttcgc caatcatcca   1680

cttaccatcg tcacctgagg aattaccaca gatctgactg aactatctaa catcctcagc   1740

agagactggt agggcttcag cctcagtatg tcatcttcaa agagagaaga atgttgcaag   1800

taaattgtac tgtcccaata atgatataac atgcttgtgg attgccactt ttatgttttg   1860

ttttgttttg ttwtttatkt tgtgtgtgtg tatgtaattt tttgtctgta tttccatatt   1920

tccacagcat aagttattag aatactttgc tgttaattct tgagttgctt cttgctttta   1980

gacagtgtct ttctggttgg cagctttata cacctgtctt tctggcacta gagtttccaa   2040

acattttctg atctccactt ttattttcta cagtgttctt gacagaagcc tggcattccc   2100

tctgacattt tctacatgtt ggggttttca tcccaagtct tagggttgca agttaaatgc   2160
```

attgcctctt cagacatctc atgccatgtc tactgcttac agttcaagaa tatttctcta 2220
cattactaga acgacgttca aagtggaata ataaataaat aaataatcaa caatt 2275

<210> SEQ ID NO 8
<211> LENGTH: 506
<212> TYPE: PRT
<213> ORGANISM: Mus musculus
<220> FEATURE:
<221> NAME/KEY: DOMAIN
<222> LOCATION: (37)..(119)
<223> OTHER INFORMATION: SCAN box
<220> FEATURE:
<221> NAME/KEY: DOMAIN
<222> LOCATION: (395)..(417)
<223> OTHER INFORMATION: C2H2-type 1
<220> FEATURE:
<221> NAME/KEY: DOMAIN
<222> LOCATION: (424)..(449)
<223> OTHER INFORMATION: C2H2-type 2
<220> FEATURE:
<221> NAME/KEY: DOMAIN
<222> LOCATION: (452)..(474)
<223> OTHER INFORMATION: C2H2-type 3
<220> FEATURE:
<221> NAME/KEY: DOMAIN
<222> LOCATION: (480)..(503)
<223> OTHER INFORMATION: C2H2-type 4

<400> SEQUENCE: 8

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255
```

```
Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505
```

```
<210> SEQ ID NO 9
<211> LENGTH: 2268
<212> TYPE: DNA
<213> ORGANISM: Mus musculus

<400> SEQUENCE: 9

cacagtgcct ccctgggctt cttggcatca cccttgaagt tcactggaca aagaggtgag      60

gtggaggagt aggtaaactt cccttcctag tggtcgtgaa tgtcttttac agtacatcca     120

tcaactgtta gcattttcat aaagtcacaa aacagatact aaactgctat agttgaatct     180

ttcacaccat tgtcaccaca atggcttcac agcaggcacc agcaaaagac cttcagacca     240

acaatttaga gtttactcca tctcatagtt ctggtgtgca gtgggtagaa gacatctcta     300

actcaccaag tgctcagcta aacttttctc caagtaacaa tggctgctgg gcaactcagg     360

agctgcaaag tctctggaag atgttcaact cctggttgca gccagaaaag cagactaagg     420

agcagatgat ttctcaactg gtcttggagc agtttctcct cattgggcac tgcaaggaca     480

agtatgcttt gacagagaag tggaaagcca gtggtagcga tatgaggaga ttcatggaga     540

gtctgactga tgagtgcttg aagcctcctg tcatggtcca tgtttcaatg caaggacaag     600

aagctctctt ttctgaaaac atgccattaa aagaagtcat caagcttttg aaacaacagc     660
```

-continued

```
aatctgcaac aaggccaaca ccagataatg agcagatgcc agtagacacc acacaagata    720

gattattggc cacaggacaa gaaaacagtg aaaatgaatg caacaactct tgtaatgcta    780

ctgaagcaaa tgttggtgaa agctgtagtg gaaatgaaat ggactccctt cttattatcc    840

agaaagaaca gcaccctgag catgaagagg ggaatgttgt ttttcaattc cctcttgatg    900

ccagaagagc aagtcaaggc aactccagtc atcatgtaga cttccggagt gctccgactc    960

ctgcggatgt ccccatggag gaacaaccaa aggatttatc cagagaaaac atctctgagg   1020

acaagaacaa ttgctataac acttccagga atgcagctac tcaagtatat agaagtgata   1080

atattcccag gaaaaagaca gactcccttt ccattaacaa gagaatatat cattctgagc   1140

ctgaggaggg agatattcct tatggagttc ctcaggattc tacaagagca agtcaaggaa   1200

catctacatg cttgcaagag tcacttgggg aatgtttttc tgaaaaagac cctagggagc   1260

taccagggtt ggagtctagg caagaggagc ctatctctga tcctgtcttt cttggtaagg   1320

atcatgaggc aaacttacca tgtgaaagtc atcaaaagag attccgtaga gatgccaaac   1380

tattcaagtg tgaagaatgt tctaggatgt tcaaacatgc caggagcctt tcgtcccacc   1440

agagaactca cctgaataag aagagtgaat tgctttgtgt cacctgtcag aaaatgttca   1500

aacgagtctc tgaccgccga acccatgaga tcatacacat gccagaaaag cctttcaagt   1560

gcagcacatg tgaaaagtcc ttcagccaca agaccaacct gaagtctcat gagatgattc   1620

acacaggaga aatgccttat gtctgttccc tatgtagccg tcgctttcgc caatcatcca   1680

cttaccatcg tcacctgagg aattaccaca gatctgactg aagtatctaa catcctcagc   1740

agagactggt agggcttcag cctcagtatg tcatcttcaa agagagaaga atgttgcaag   1800

taaattgtac tgtcccaata atgatataac atgcttgtgg attgccactt ttatgttttg   1860

tttttattg tgtgtgtgtg tgtatgtaat tttttgtctg taatttccat agttccacag   1920

cataagttat tagaatactt tgctgttaat tcttgagttg cttcttgctt ttagacagtg   1980

tctttctggt tggcagcttt atacacctgt ctttctggca ctagagtttc caaacatttt   2040

ctgatctcca cttttattct ctacagtggt cctgacagag gcctgccatt ccctctgaca   2100

ttttttaaca tgttggggtt tcatcccaag tcttagggtt gcaagttaaa tgcattgcct   2160

cttcagacat ctcatgtcat gtctactgct tacagttcaa gaatatttct ctacattact   2220

agaatgacgt tcaaagtgga ataataaata aaaaaataat caacaatt                2268

<210> SEQ ID NO 10
<211> LENGTH: 506
<212> TYPE: PRT
<213> ORGANISM: Mus musculus

<400> SEQUENCE: 10

Met Ala Ser Gln Gln Ala Pro Ala Lys Asp Leu Gln Thr Asn Asn Leu
1               5                   10                  15

Glu Phe Thr Pro Ser His Ser Ser Gly Val Gln Trp Val Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Ile Gly His Cys Lys Asp Lys Tyr Ala
                85                  90                  95
```

-continued

```
Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Phe Gln Phe Pro Leu Asp Ala Arg Arg Ala Ser Gln Gly
225                 230                 235                 240

Asn Ser Ser His His Val Asp Phe Arg Ser Ala Pro Thr Pro Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Arg Ser Asp Asn Ile Pro Arg Lys Lys Thr Asp Ser Leu Ser
    290                 295                 300

Ile Asn Lys Arg Ile Tyr His Ser Glu Pro Glu Glu Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Leu Pro Gly Leu Glu Ser Arg Gln Glu Glu Pro Ile Ser Asp Pro
        355                 360                 365

Val Phe Leu Gly Lys Asp His Glu Ala Asn Leu Pro Cys Glu Ser His
    370                 375                 380

Gln Lys Arg Phe Arg Arg Asp Ala Lys Leu Phe Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505
```

-continued

<210> SEQ ID NO 11
<211> LENGTH: 1774
<212> TYPE: DNA
<213> ORGANISM: Mus musculus

<400> SEQUENCE: 11
cacagtgcct ccctgggctt cttggcatca ccattgaagt tcactggaga aagaggtgag 60
gtggagaagt aggtaaactt ccctttcttg tggtcttgaa tgtcttttac agtacatccg 120
tcaactgtta gcattttcct aaagtcacaa aacagatact aaactgctat agttgaatct 180
ttcagaccat tgtcaccaca atggcttcac agcaggcacc agcaaaagac cttcagacca 240
acaatttaga gtttactcca actgatagtt ctggtgtgca gtgggcagaa gacatctcta 300
actcaccaag tgctcagcta aacttttccc caagtaacaa tggctgctgg gcaactcagg 360
agctgcaaag tctctggaag atgttcaact cctggttgca gccagaaaag cagactaagg 420
agcagatgat ttctcaactg gtcttggagc agtttctcct cactgggcac tgcaaggaca 480
agtatgcttt gacagagaag tggaaagcca gtggtagcga tatgaggaga ttcatggaga 540
gtctgactga tgagtgcttg aagcctcctg tcatggtcca tgtttcaatg caaggacaag 600
aagccctctt ttctgaaaac atgccattaa aagaagtcat caagcttttg aaacaacagc 660
aatctgcaac aaggccaata ccagataatg agcagatgcc agtagacacc acacaagata 720
gattattggc cacaggcaag aaaacagtga aaatgaatgc aacacctctt gcaatgctac 780
tgaagtaaat gttggtgaaa gctgtagtgg aaatgaaaag gactcccttc ttattaccca 840
gaaagaacaa aaccatgagc atgaagaggg gaatgttgtt tgtcaattcc ctcgtggtgc 900
cagaagagca agtcaagaca cctccagtca tcatgtagac ttcccgagtg ctctgactcc 960
tgcagatgtc cccatggagg aacaaccaat ggatttatcc agagaaaaca tctctgagga 1020
caagaacaat tgctataaca cttccaggaa tgcagctact caagtatata atggtgataa 1080
tattcccagg aacaagacag actccctttt cattaacaag agaatatatc atcctgagcc 1140
tgaggtggga gatattcctt atggagttcc tcaggattct acaagagcaa gtcaaggaac 1200
atctacatgc ctgcaagagt cacttgggga atgtttttct gaaaaagacc caagggaggt 1260
accagggttg cagtctaggc aagagcagcc tatctctgat cctgtccttg gtaagaatca 1320
tgaggcaaac ttaccatgtg aaagtcatca aaagagattc catagagatg ccaaactata 1380
caagtgtgaa gaatgttcta ggatgttcaa acatgccagg agcctttcat cccaccagag 1440
aactcacctg aataagaaga gtgaattgct ttgcatcacc tgtcagaaaa tattcaaacg 1500
agtttctgac cttcgaaccc atgagatcat acacatgtca gaaaagcctt tcaagtgcag 1560
cacatgtgaa aagtccttca gccacaagac caacctgaag tatcatgaga tgattcacac 1620
aggagaaatg ccttatgtct gttccctatg tagccgtcgc tttcgccaat catccactta 1680
ccatcgtcac ctgaggaatt accacagatc tgactgaagt atctaacatc ctcagcagag 1740
actggtaggg cttcagcctc agtatgtcat cttc 1774

<210> SEQ ID NO 12
<211> LENGTH: 195
<212> TYPE: PRT
<213> ORGANISM: Mus musculus

<400> SEQUENCE: 12

Met Ala Ser Gln Gln Ala Pro Ala Lys Asp Leu Gln Thr Asn Asn Leu
1 5 10 15

-continued

```
Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Ile
145                 150                 155                 160

Pro Asp Asn Glu Gln Met Pro Val Asp Thr Thr Gln Asp Arg Leu Leu
                165                 170                 175

Ala Thr Gly Lys Lys Thr Val Lys Met Asn Ala Thr Pro Leu Ala Met
            180                 185                 190

Leu Leu Lys
        195
```

<210> SEQ ID NO 13
<211> LENGTH: 2273
<212> TYPE: DNA
<213> ORGANISM: Mus musculus

<400> SEQUENCE: 13

```
cacagtgcct ccctgggctt cttggcatca cccttgaagt tcactggaga aagaggtgag     60

gtggaggaat aggtaaactt tccttcctag tggtcttgaa tgtcttttac agtacatcca    120

tcaactgtta gcattttcgt aaagtcacaa aacagatatt aaactactat agttgaatct    180

ttcacaccat tgtcaccaca atggcttcac agcaggcacc agcaaaagac cttcagacca    240

acaatttaga gtttactcca actgatagtt ctggtgtgca gtgggcagaa gacatctcta    300

actcaccaag tgctcagcta aacttttccc caagtaacaa tggctgctgg gcaactcagg    360

agctgcaaag tctctggaag atgttcaact cctggttgca gccagaaaag cagactaagg    420

agcagatgat ttctcaactg gtcttggagc agtttctcct cactgggcac tgcaaggaca    480

agtatgcttt gactgagaag tggaaagcca gtggtagcga tatgaggaga ttcatggaga    540

gtctgactga tgagtgcttg aagcctcctg tcatggtcca tgtttcaatg caaggacaag    600

aagccctctt ttctgaaaac atgccattaa aagaagtcat caagcttttg aaacaacagc    660

aatctgcaac aaggccaaca ccagataatg agcagatgcc agtagacacc acacaagata    720

gattattggc cacaggacaa gaaaacagtg aaaatgaatg caacaactct tgtaatgcta    780

ctgaagcaaa tgttggtgaa agctgtagtg gaaatgaaat ggactccctt cttattatgc    840

agaaagaaca gcaccctgag catgaagagg ggaatgttgt ttgtcaattc cctcatggtg    900

ccagaagagc aagtcaaggc acccccagtc atcatgtaga cttcccgagt gctccgacta    960

ctgccgatgt ccccatggag gaacaaccaa aggatttatc cagagaaaac atctctgagg   1020

acaagaacaa ttgctataac acttccagaa atgcagctac tcaagtatat agtggtgata   1080
```

```
atattcccag gaacaagtca gactcccttt tcattaacaa gagaatatat catcctgagc   1140

ctgaggtggg agatattcct tatggagttc ctcaggattc tacaagagca agtcaaggaa   1200

catctacatg cctgcaagag tcacttgggg aatgtttttc tgaaaaagac cctagggagg   1260

taccagggtt gcagtctagg caagagcagc ttatctctga tcctgtcctt cttggtaaga   1320

atcatgaggc aaacttacca tgtgaaagtc atcaaaagag attctgtaga gatgccaaac   1380

tatacaagtg tgaagaatgt tctaggatgt tcaaacatgc caggagcctt tcatcccacc   1440

agagaactca cctgaataag aagagtgaat tgctttgtgt cacctgtcag aaaatgttca   1500

aacgagtctc tgaccgccga acccatgaga tcatacacat gccagaaaag cctttcaagt   1560

gcagcacatg tgaaaagtcc ttcagccaca agaccaacct gaagtctcat gagatgattc   1620

acacaggaga aatgccttat gtctgttccc tatgtagccg tcgctttcgc caatcatcca   1680

cttaccatcg tcacctgagg aattaccaca gatctgactg aactatctaa catcctcagc   1740

agagactggt agggcttcag cctcagtatg tcatcttcaa agagagaaga atgttgcaag   1800

taaattgtac tgtcccaata atgatataac atgcttgtgg attgccactt ttatgttttg   1860

ttttgttttt tattttgtgt gtgtgtgtat gtaatttttt gtctgtattt ccatagttcc   1920

acagcataag ttattagaat actttgctgt taattcttga gttgcttctt gcttttagac   1980

agtgtctttc tggttgacag ctttataaac ctgtctttct ggcactagag tttccaaaca   2040

ttttctgatc tccactttta ttctctacag tgttcttgac agaagcctgg cattccctct   2100

gacatttttc tacatgttgg ggttttcatc ccaagtctta gggttgcaag ttaaatgcat   2160

tgcctcttca gacatctcat gccctgtcta ctgcttacag ttcaagaata tttctctaca   2220

ttactagaac gacattcaaa gtggaataat aaataaataa ataatcaaca att          2273
```

<210> SEQ ID NO 14
<211> LENGTH: 506
<212> TYPE: PRT
<213> ORGANISM: Mus musculus

<400> SEQUENCE: 14

```
Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160
```

```
Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Met Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Lys Asp Pro Arg
            340                 345                 350

Glu Val Pro Gly Leu Gln Ser Arg Gln Glu Gln Leu Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp
            500                 505
```

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
agtctgactg atgagtgctt gaagcc 26

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
ggccttgttg cagattgctg ttg 23

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 17
ttgcagcttg ctatacgtgg agatg 25

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
tgttgtcctt tcttcccgat cagc 24

<210> SEQ ID NO 19
<211> LENGTH: 8904
<212> TYPE: DNA
<213> ORGANISM: Artificial Sequence
<220> FEATURE:
<223> OTHER INFORMATION: Recombinant plasmid (pPyCAG-mZscan4c-ERT2)
<220> FEATURE:
<221> NAME/KEY: misc_feature
<222> LOCATION: (1110)..(2351)
<223> OTHER INFORMATION: CAG promoter
<220> FEATURE:
<221> NAME/KEY: misc_feature
<222> LOCATION: (2465)..(3982)
<223> OTHER INFORMATION: Mouse Zscan4c coding sequence
<220> FEATURE:
<221> NAME/KEY: misc_feature
<222> LOCATION: (2465)..(4936)
<223> OTHER INFORMATION: Zscan4c-ERT2 fusion protein coding sequence
<220> FEATURE:
<221> NAME/KEY: misc_feature
<222> LOCATION: (3983)..(3988)
<223> OTHER INFORMATION: Linker
<220> FEATURE:
<221> NAME/KEY: misc_feature
<222> LOCATION: (3989)..(4936)
<223> OTHER INFORMATION: ERT2 coding sequence

<400> SEQUENCE: 19
gaccgctttg gaaaaacaaa gactgtattt cctggaaatt aatgtttatt caataaactg 60
tgtattcagc tatattcaca tagtggtgag gctgaaatga ggcgggaaga ggcggttggg 120
gcttaattat atcaatttgg gtggccccac agcgcctcca aggcgccagt cctgttttga 180
caagttgcct ctggaagcct ctcttctttt tctccagagt aagcggaggc caggggcccc 240
cggcctctgc ttaatactaa aaaaaacagc tgttgtcata gtaatgattg ggtggaaaca 300
ttccaggcct gggtggagag gctttttgct tcctcttgca aaccacact gacattccag 360 gcctgggtgg agaggctttt tgcttcctct tgcaaaacca cactgccctc tggagggcag 420

-continued

```
ttgcctagca actaattaaa agaggatgtc gcacggccag ctgcggtcag ttagtcactt    480
cctgcttaac tgacttgaca ttttctattt taagagtcgg gaggaaaatt actgtgttgg    540
aggccctccg ccatcttctg aagctgaatc gaattaactt gtttattgca gcttataatg    600
gttacaaata aagcaatagc atcacaaatt tcacaaataa agcatttttt tcactgcatt    660
ctagttgtgg tttgtccaaa ctcatcaatg tatcttatca tgtctggatc tgatatcatc    720
gtcgacattg attattgact agttattaat agtaatcaat tacggggtca ttagttcata    780
gcccatatat ggagttccgc gttacataac ttacggtaaa tggcccgcct ggctgaccgc    840
ccaacgaccc ccgcccattg acgtcaataa tgacgtatgt tcccatagta acgccaatag    900
ggactttcca ttgacgtcaa tgggtggagt atttacggta aactgcccac ttggcagtac    960
atcaagtgta tcatatgcca agtacgcccc ctattgacgt caatgacggt aaatggcccg   1020
cctggcatta tgcccagtac atgaccttat gggactttcc tacttggcag tacatctacg   1080
tattagtcat cgctattacc atggtcgagg tgagccccac gttctgcttc actctcccca   1140
tctccccccc ctccccaccc ccaattttgt atttatttat tttttaatta ttttgtgcag   1200
cgatgggggc gggggggggg ggggggcgcg cgccaggcgg ggcggggcgg ggcgaggggc   1260
ggggcggggc gaggcggaga ggtgcggcgg cagccaatca gagcggcgcg ctccgaaagt   1320
ttccttttat ggcgaggcgg cggcggcggc ggccctataa aaagcgaagc gcgcggcggg   1380
cgggagtcgc tgcgcgctgc cttcgccccg tgccccgctc cgccgccgcc tcgcgccgcc   1440
cgccccggct ctgactgacc gcgttactcc cacaggtgag cgggcgggac ggcccttctc   1500
ctccgggctg taattagcgc ttggtttaat gacggcttgt ttcttttctg tggctgcgtg   1560
aaagccttga ggggctccgg gagggccctt tgtgcggggg gagcggctcg gggggtgcgt   1620
gcgtgtgtgt gtgcgtgggg agcgccgcgt gcggctccgc gctgcccggc ggctgtgagc   1680
gctgcgggcg cggcgcgggg ctttgtgcgc tccgcagtgt gcgcgagggg agcgcggccg   1740
ggggcggtgc cccgcggtgc ggggggggct gcgaggggaa caaaggctgc gtgcggggtg   1800
tgtgcgtggg ggggtgagca gggggtgtgg gcgcgtcggt cgggctgcaa ccccccctgc   1860
acccccctcc ccgagttgct gagcacggcc cggcttcggg tgcggggctc cgtacggggc   1920
gtggcgcggg gctcgccgtg ccgggcgggg ggtggcggca ggtgggggtg ccgggcgggg   1980
cggggccgcc tcgggccggg gagggctcgg gggaggggcg cggcggcccc cggagcgccg   2040
gcggctgtcg aggcgcggcg agccgcagcc attgcctttt atggtaatcg tgcgagaggg   2100
cgcagggact tcctttgtcc caaatctgtg cggagccgaa atctgggagg cgccgccgca   2160
ccccctctag cgggcgcggg gcgaagcggt gcggcgccgg caggaaggaa atgggcgggg   2220
agggccttcg tgcgtcgccg cgccgccgtc cccttctccc tctccagcct cggggctgtc   2280
cgcgggggga cggctgcctt cgggggggac ggggcagggc ggggttcggc ttctggcgtg   2340
tgaccggcgg ctctagagcc tctgctaacc atgttcatgc cttcttcttt ttcctacagc   2400
tcctgggcaa cgtgctggtt attgtgctgt ctcatcattt tggcaaagaa ttcctcgagc   2460
caccatggct tcacagcagg caccagcaaa agaccttcag accaacaatt tagagtttac   2520
tccaactgat agttctggtg tgcagtgggc agaagacatc tctaactcac caagtgctca   2580
gctaaacttt tccccaagta acaatggctg ctgggcaact caggagctgc aaagtctctg   2640
gaagatgttc aactcctggt tgcagccaga aaagcagact aaggagcaga tgatttctca   2700
actggtcttg gagcagtttc tcctcactgg gcactgcaag gacaagtatg ctttgacaga   2760
gaagtggaaa gccagtggta gcgatatgag gagattcatg gagagtctga ctgatgagtg   2820
```

-continued

```
cttgaagcct cctgtcatgg tccatgtttc aatgcaagga caagaagccc tcttttctga   2880
aaacatgcca ttaaaagaag tcatcaagct tttgaaacaa cagcaatctg caacaaggcc   2940
aacaccagat aatgagcaga tgccagtaga caccacacaa gatagattat tggccacagg   3000
acaagaaaac agtgaaaatg aatgcaacaa ctcttgtaat gctactgaag caaatgttgg   3060
tgaaagctgt agtggaaatg aaatggactc ccttcttatt atccagaaag aacagcaccc   3120
tgagcatgaa gaggggaatg ttgtttgtca attccctcat ggtgccagaa gagcaagtca   3180
aggcaccccc agtcatcatg tagacttccc gagtgctccg actactgccg atgtccccat   3240
ggaggaacaa ccaaaggatt tatccagaga aaacatctct gaggacaaga acaattgcta   3300
taacacttcc agaaatgcag ctactcaagt atatagtggt gataatattc ccaggaacaa   3360
gtcagactcc cttttcatta acaagagaat atatcatcct gagcctgagg tgggagatat   3420
tccttatgga gttcctcagg attctacaag agcaagtcaa ggaacatcta catgcctgca   3480
agagtcactt ggggaatgtt tttctgaaaa cgacccaagg gaggtaccag ggttgcagtc   3540
taggcaagag cagcctatct ctgatcctgt ccttcttggt aagaatcatg aggcaaactt   3600
accatgtgaa agtcatcaaa agagattctg tagagatgcc aaactataca agtgtgaaga   3660
atgttctagg atgttcaaac atgccaggag cctttcatcc caccagagaa ctcacctgaa   3720
taagaagagt gaattgcttt gtgtcacctg tcagaaaatg ttcaaacgag tctctgaccg   3780
ccgcacccat gagatcatac acatgccaga aaagcctttc aagtgcagca catgtgaaaa   3840
gtccttcagc cacaagacca acctgaagtc tcatgagatg attcacacag gagaaatgcc   3900
ttatgtctgt tccctatgta gccgtcgctt tcgccaatca tccacttacc atcgtcacct   3960
gaggaattac cacagatctg acgctagccc atctgctgga gacatgagag ctgccaacct   4020
ttggccaagc ccgctcatga tcaaacgctc taagaagaac agcctggcct tgtccctgac   4080
ggccgaccag atggtcagtg ccttgttgga tgctgagccc cccatactct attccgagta   4140
tgatcctacc agacccttca gtgaagcttc gatgatgggc ttactgacca acctggcaga   4200
cagggagctg gttcacatga tcaactgggc gaagagggtg ccaggctttg tggatttgac   4260
cctccatgat caggtccacc ttctagaatg tgcctggcta gagatcctga tgattggtct   4320
cgtctggcgc tccatggagc acccagtgaa gctactgttt gctcctaact tgctcttgga   4380
caggaaccag ggaaaatgtg tagagggcat ggtggagatc ttcgacatgc tgctggctac   4440
atcatctcgg ttccgcatga tgaatctgca gggagaggag tttgtgtgcc tcaaatctat   4500
tattttgctt aattctggag tgtacacatt tctgtccagc accctgaagt ctctggaaga   4560
gaaggaccat atccaccgag tcctggacaa gatcacagac actttgatcc acctgatggc   4620
caaggcaggc ctgaccctgc agcagcagca ccagcggctg gcccagctcc tcctcatcct   4680
ctcccacatc aggcacatga gtaacaaagg catggagcat ctgtacagca tgaagtgcaa   4740
gaacgtggtg cccctctatg acctgctgct ggaggcggcg gacgcccacc gcctacatgc   4800
gcccactagc cgtggagggg catccgtgga ggagacggac caaagccact tggccactgc   4860
gggctctact tcatcgcatt ccttgcaaaa gtattacatc acgggggagg cagagggttt   4920
ccctgccaca gcttgagcgg ccgctcgata agcttgatat cgaattccgc cccccccccc   4980
tctccctccc ccccccctaa cgttactggc cgaagccgct tggaataagg ccggtgtgcg   5040
tttgtctata tgttattttc caccatattg ccgtcttttg gcaatgtgag ggcccggaaa   5100
cctggccctg tcttcttgac gagcattcct aggggtcttt cccctctcgc caaaggaatg   5160
```

-continued

```
caaggtctgt tgaatgtcgt gaaggaagca gttcctctgg aagcttcttg aagacaaaca   5220
acgtctgtag cgaccctttg caggcagcgg aaccccccac ctggcgacag gtgcctctgc   5280
ggccaaaagc cacgtgtata agatacacct gcaaaggcgg cacaacccca gtgccacgtt   5340
gtgagttgga tagttgtgga aagagtcaaa tggctctcct caagcgtatt caacaagggg   5400
ctgaaggatg cccagaaggt accccattgt atgggatctg atctggggcc tcggtgcaca   5460
tgctttacat gtgtttagtc gaggttaaaa aaacgtctag gccccccgaa ccacggggac   5520
gtggttttcc tttgaaaaac acgatgataa tatggccaca accatgaccg agtacaagcc   5580
cacggtgcgc ctcgccaccc gcgacgacgt ccccagggcc gtacgcaccc tcgccgccgc   5640
gttcgccgac taccccgcca cgcgccacac cgtcgatccg gaccgccaca tcgagcgggt   5700
caccgagctg caagaactct tcctcacgcg cgtcgggctc gacatcggca aggtgtgggt   5760
cgcggacgac ggcgccgcgg tggcggtctg gaccacgccg gagagcgtcg aagcgggggc   5820
ggtgttcgcc gagatcggcc cgcgcatggc cgagttgagc ggttcccggc tggccgcgca   5880
gcaacagatg gaaggcctcc tggcgccgca ccggcccaag gagcccgcgt ggttcctggc   5940
caccgtcggc gtctcgcccg accaccaggg caagggtctg ggcagcgccg tcgtgctccc   6000
cggagtggag gcggccgagc gcgccggggt gcccgccttc ctggagacct ccgcgccccg   6060
caacctcccc ttctacgagc ggctcggctt caccgtcacc gccgacgtcg aggtgcccga   6120
aggaccgcgc acctggtgca tgacccgcaa gcccggtgcc tgacgcccgc cccacgaccc   6180
gcagcgcccg accgaaagga gcgcacgacc ccatgcatcg atgatctaga gctcgctgat   6240
cagcctcgac tgtgccttct agttgccagc catctgttgt ttgcccctcc cccgtgcctt   6300
ccttgaccct ggaaggtgcc actcccactg tcctttccta ataaaatgag gaaattgcat   6360
cgcattgtct gagtaggtgt cattctattc tggggggtgg ggtggggcag gacagcaagg   6420
gggaggattg ggaagacaat agcaggcatg ctggggatgc ggtgggctct atggcttctg   6480
aggcggaaag aacctgcagc ccaagcttgg cgtaatcatg gtcatagctg tttcctgtgt   6540
gaaattgtta tccgctcaca attccacaca acatacgagc cggaagcata aagtgtaaag   6600
cctggggtgc ctaatgagtg agctaactca cattaattgc gttgcgctca ctgcccgctt   6660
tccagtcggg aaacctgtcg tgccagcgga tccgcatctc aattagtcag caaccatagt   6720
cccgccccta actccgccca tcccgcccct aactccgccc agttccgccc attctccgcc   6780
ccatggctga ctaatttttt ttatttatgc agaggccgag gccgcctcgg cctctgagct   6840
attccagaag tagtgaggag gcttttttgg aggcctaggc ttttgcaaaa agctaacttg   6900
tttattgcag cttataatgg ttacaaataa agcaatagca tcacaaattt cacaaataaa   6960
gcattttttt cactgcattc tagttgtggt ttgtccaaac tcatcaatgt atcttatcat   7020
gtctggatcc gctgcattaa tgaatcggcc aacgcgcggg gagaggcggt ttgcgtattg   7080
ggcgctcttc cgcttcctcg ctcactgact cgctgcgctc ggtcgttcgg ctgcggcgag   7140
cggtatcagc tcactcaaag gcggtaatac ggttatccac agaatcaggg gataacgcag   7200
gaaagaacat gtgagcaaaa ggccagcaaa aggccaggaa ccgtaaaaag gccgcgttgc   7260
tggcgttttt ccataggctc cgcccccctg acgagcatca caaaaatcga cgctcaagtc   7320
agaggtggcg aaacccgaca ggactataaa gataccaggc gtttccccct ggaagctccc   7380
tcgtgcgctc tcctgttccg accctgccgc ttaccggata cctgtccgcc tttctccctt   7440
cgggaagcgt ggcgctttct catagctcac gctgtaggta tctcagttcg gtgtaggtcg   7500
ttcgctccaa gctgggctgt gtgcacgaac cccccgttca gcccgaccgc tgcgccttat   7560
```

-continued ccggtaacta tcgtcttgag tccaacccgg taagacacga cttatcgcca ctggcagcag 7620
ccactggtaa caggattagc agagcgaggt atgtaggcgg tgctacagag ttcttgaagt 7680
ggtggcctaa ctacggctac actagaagaa cagtatttgg tatctgcgct ctgctgaagc 7740
cagttacctt cggaaaaaga gttggtagct cttgatccgg caaacaaacc accgctggta 7800
gcggtggttt ttttgtttgc aagcagcaga ttacgcgcag aaaaaaagga tctcaagaag 7860
atcctttgat cttttctacg gggtctgacg ctcagtggaa cgaaaactca cgttaaggga 7920
ttttggtcat gagattatca aaaaggatct tcacctagat ccttttaaat taaaaatgaa 7980
gttttaaatc aatctaaagt atatatgagt aaacttggtc tgacagttac caatgcttaa 8040
tcagtgaggc acctatctca gcgatctgtc tatttcgttc atccatagtt gcctgactcc 8100
ccgtcgtgta gataactacg atacgggagg gcttaccatc tggccccagt gctgcaatga 8160
taccgcgaga cccacgctca ccggctccag atttatcagc aataaaccag ccagccggaa 8220
gggccgagcg cagaagtggt cctgcaactt tatccgcctc catccagtct attaattgtt 8280
gccgggaagc tagagtaagt agttcgccag ttaatagttt gcgcaacgtt gttgccattg 8340
ctacaggcat cgtggtgtca cgctcgtcgt ttggtatggc ttcattcagc tccggttccc 8400
aacgatcaag gcgagttaca tgatccccca tgttgtgcaa aaaagcggtt agctccttcg 8460
gtcctccgat cgttgtcaga agtaagttgg ccgcagtgtt atcactcatg gttatggcag 8520
cactgcataa ttctcttact gtcatgccat ccgtaagatg cttttctgtg actggtgagt 8580
actcaaccaa gtcattctga gaatagtgta tgcggcgacc gagttgctct tgcccggcgt 8640
caatacggga taataccgcg ccacatagca gaactttaaa agtgctcatc attggaaaac 8700
gttcttcggg gcgaaaactc tcaaggatct taccgctgtt gagatccagt tcgatgtaac 8760
ccactcgtgc acccaactga tcttcagcat cttttacttt caccagcgtt tctgggtgag 8820
caaaaacagg aaggcaaaat gccgcaaaaa agggaataag ggcgacacgg aaatgttgaa 8880
tactcatact cttccttttt caat 8904

<210> SEQ ID NO 20
<211> LENGTH: 8699
<212> TYPE: DNA
<213> ORGANISM: Artificial Sequence
<220> FEATURE:
<223> OTHER INFORMATION: Recombinant plasmid (pPyCAG-hZscan4-ERT2)
<220> FEATURE:
<221> NAME/KEY: misc_feature
<222> LOCATION: (1110)..(2351)
<223> OTHER INFORMATION: CAG promoter
<220> FEATURE:
<221> NAME/KEY: misc_feature
<222> LOCATION: (2479)..(3777)
<223> OTHER INFORMATION: Human Zscan4 coding sequence
<220> FEATURE:
<221> NAME/KEY: misc_feature
<222> LOCATION: (2479)..(4731)
<223> OTHER INFORMATION: Zscan4-ERT2 fusion protein coding sequence
<220> FEATURE:
<221> NAME/KEY: misc_feature
<222> LOCATION: (3778)..(3783)
<223> OTHER INFORMATION: Linker
<220> FEATURE:
<221> NAME/KEY: misc_feature
<222> LOCATION: (3784)..(4731)
<223> OTHER INFORMATION: ERT2 coding sequence

<400> SEQUENCE: 20
gaccgctttg gaaaaacaaa gactgtattt cctggaaatt aatgtttatt caataaactg 60

-continued

```
tgtattcagc tatattcaca tagtggtgag gctgaaatga ggcgggaaga ggcggttggg    120
gcttaattat atcaatttgg gtggccccac agcgcctcca aggcgccagt cctgttttga    180
caagttgcct ctggaagcct ctcttctttt tctccagagt aagcggaggc caggggcccc    240
cggcctctgc ttaatactaa aaaaaacagc tgttgtcata gtaatgattg ggtggaaaca    300
ttccaggcct gggtggagag gctttttgct tcctcttgca aaaccacact gacattccag    360
gcctgggtgg agaggctttt tgcttcctct tgcaaaacca cactgccctc tggagggcag    420
ttgcctagca actaattaaa agaggatgtc gcacggccag ctgcggtcag ttagtcactt    480
cctgcttaac tgacttgaca ttttctattt taagagtcgg gaggaaaatt actgtgttgg    540
aggccctccg ccatcttctg aagctgaatc gaattaactt gtttattgca gcttataatg    600
gttacaaata aagcaatagc atcacaaatt tcacaaataa agcatttttt tcactgcatt    660
ctagttgtgg tttgtccaaa ctcatcaatg tatcttatca tgtctggatc tgatatcatc    720
gtcgacattg attattgact agttattaat agtaatcaat tacggggtca ttagttcata    780
gcccatatat ggagttccgc gttacataac ttacggtaaa tggcccgcct ggctgaccgc    840
ccaacgaccc ccgcccattg acgtcaataa tgacgtatgt tcccatagta acgccaatag    900
ggactttcca ttgacgtcaa tgggtggagt atttacggta aactgcccac ttggcagtac    960
atcaagtgta tcatatgcca agtacgcccc ctattgacgt caatgacggt aaatggcccg   1020
cctggcatta tgcccagtac atgaccttat gggactttcc tacttggcag tacatctacg   1080
tattagtcat cgctattacc atggtcgagg tgagccccac gttctgcttc actctcccca   1140
tctccccccc ctccccaccc ccaattttgt atttatttat tttttaatta ttttgtgcag   1200
cgatgggggc gggggggggg ggggggcgcg cgccaggcgg ggcggggcgg ggcgaggggc   1260
ggggcggggc gaggcggaga ggtgcggcgg cagccaatca gagcggcgcg ctccgaaagt   1320
ttccttttat ggcgaggcgg cggcggcggc ggccctataa aaagcgaagc gcgcggcggg   1380
cgggagtcgc tgcgcgctgc cttcgccccg tgccccgctc cgccgccgcc tcgcgccgcc   1440
cgccccggct ctgactgacc gcgttactcc cacaggtgag cgggcgggac ggcccttctc   1500
ctccgggctg taattagcgc ttggtttaat gacggcttgt ttcttttctg tggctgcgtg   1560
aaagccttga ggggctccgg gagggccctt tgtgcggggg gagcggctcg gggggtgcgt   1620
gcgtgtgtgt gtgcgtgggg agcgccgcgt gcggctccgc gctgcccggc ggctgtgagc   1680
gctgcgggcg cggcgcgggg ctttgtgcgc tccgcagtgt gcgcgagggg agcgcggccg   1740
ggggcggtgc cccgcggtgc ggggggggct gcgaggggaa caaaggctgc gtgcggggtg   1800
tgtgcgtggg ggggtgagca gggggtgtgg gcgcgtcggt cgggctgcaa ccccccctgc   1860
acccccctcc ccgagttgct gagcacggcc cggcttcggg tgcggggctc cgtacggggc   1920
gtggcgcggg gctcgccgtg ccgggcgggg ggtggcggca ggtgggggtg ccgggcgggg   1980
cggggccgcc tcgggccggg gagggctcgg gggaggggcg cggcggcccc cggagcgccg   2040
gcggctgtcg aggcgcggcg agccgcagcc attgcctttt atggtaatcg tgcgagaggg   2100
cgcagggact tcctttgtcc caaatctgtg cggagccgaa atctgggagg cgccgccgca   2160
ccccctctag cgggcgcggg gcgaagcggt gcggcgccgg caggaaggaa atgggcgggg   2220
agggccttcg tgcgtcgccg cgccgccgtc cccttctccc tctccagcct cggggctgtc   2280
cgcgggggga cggctgcctt cgggggggac ggggcagggc ggggttcggc ttctggcgtg   2340
tgaccggcgg ctctagagcc tctgctaacc atgttcatgc cttcttcttt ttcctacagc   2400
tcctgggcaa cgtgctggtt attgtgctgt ctcatcattt ggcaaagaa ttcctcgaga   2460
```

-continued

```
tccattgtgc tggccaccat ggctttagat ctaagaacca tatttcagtg tgaaccatcc   2520
gagaataatc ttggatcaga aaattcagcg tttcaacaaa gccaaggacc tgctgttcag   2580
agagaagaag ggatttctga gttctcaaga atggtgctca attcatttca agacagcaat   2640
aattcatatg caaggcagga attgcaaaga ctttatagga tctttcactc atggctgcaa   2700
ccagaaaagc acagcaagga tgaaattatt tctctattag tcctggagca gtttatgatt   2760
ggtggccact gcaatgacaa agccagtgtg aaagagaaat ggaaatcaag tggcaaaaac   2820
ttggagagat tcatagaaga cctgactgat gacagcataa atccacctgc cttagtccac   2880
gtccacatgc agggacagga agctctcttt tctgaggata tgcccttaag agatgtcatt   2940
gttcatctca caaaacaagt gaatgcccaa accacaagag aagcaaacat ggggacaccc   3000
tcccagactt cccaagatac ttccttagaa acaggacaag gatatgaaga tgaacaagat   3060
ggctggaaca gttcttcgaa aactactcga gtaaatgaaa atattactaa tcaaggcaat   3120
caaatagttt ccctaatcat catccaggaa gagaacggtc ctaggcctga agagggaggt   3180
gtttcttctg acaacccata caactcaaaa agagcagagc tagtcactgc tagatctcag   3240
gaagggtcca taaatggaat cactttccaa ggtgtcccta tggtgatggg agcagggtgt   3300
atctctcaac cagagcagtc ctcccctgag tctgccctta cccaccagag caatgaggga   3360
aattccacat gtgaggtaca tcagaaagga tcccatggag tccaaaaatc atacaaatgt   3420
gaagaatgcc ccaaggtctt taagtatctc tgtcacttat tagctcacca gagaagacac   3480
aggaatgaga ggccatttgt ttgtcccgag tgtcaaaaag gcttcttcca gatatcagac   3540
ctacgggtgc atcagataat tcacacagga aagaagcctt tcacatgcag catgtgtaaa   3600
aagtccttca gccacaaaac caacctgcgg tctcatgaga gaatccacac aggagaaaag   3660
ccttatacat gtcccttttg taagacaagc taccgccagt catccacata ccaccgccat   3720
atgaggactc atgagaaaat taccctgcca agtgttccct ccacaccaga agcttccgct   3780
agcccatctg ctggagacat gagagctgcc aacctttggc caagcccgct catgatcaaa   3840
cgctctaaga agaacagcct ggccttgtcc ctgacggccg accagatggt cagtgccttg   3900
ttggatgctg agcccccat actctattcc gagtatgatc ctaccagacc cttcagtgaa   3960
gcttcgatga tgggcttact gaccaacctg gcagacaggg agctggttca catgatcaac   4020
tgggcgaaga gggtgccagg ctttgtggat ttgaccctcc atgatcaggt ccaccttcta   4080
gaatgtgcct ggctagagat cctgatgatt ggtctcgtct ggcgctccat ggagcaccca   4140
gtgaagctac tgtttgctcc taacttgctc ttggacagga accagggaaa atgtgtagag   4200
ggcatggtgg agatcttcga catgctgctg gctacatcat ctcggttccg catgatgaat   4260
ctgcagggag aggagtttgt gtgcctcaaa tctattattt tgcttaattc tggagtgtac   4320
acatttctgt ccagcaccct gaagtctctg gaagagaagg accatatcca ccgagtcctg   4380
gacaagatca cagacacttt gatccacctg atggccaagg caggcctgac cctgcagcag   4440
cagcaccagc ggctggccca gctcctcctc atcctctccc acatcaggca catgagtaac   4500
aaaggcatgg agcatctgta cagcatgaag tgcaagaacg tggtgcccct ctatgacctg   4560
ctgctggagg cggcggacgc ccaccgccta catgcgccca ctagccgtgg aggggcatcc   4620
gtggaggaga cggaccaaag ccacttggcc actgcgggct ctacttcatc gcattccttg   4680
caaaagtatt acatcacggg ggaggcagag ggtttccctg ccacagcttg agcggccgct   4740
cgataagctt gatatcgaat tccgcccccc cccctctcc ctcccccccc cctaacgtta   4800
```

```
ctggccgaag ccgcttggaa taaggccggt gtgcgtttgt ctatatgtta ttttccacca   4860
tattgccgtc ttttggcaat gtgagggccc ggaaacctgg ccctgtcttc ttgacgagca   4920
ttcctagggg tctttcccct ctcgccaaag gaatgcaagg tctgttgaat gtcgtgaagg   4980
aagcagttcc tctggaagct tcttgaagac aaacaacgtc tgtagcgacc ctttgcaggc   5040
agcggaaccc cccacctggc gacaggtgcc tctgcggcca aaagccacgt gtataagata   5100
cacctgcaaa ggcggcacaa ccccagtgcc acgttgtgag ttggatagtt gtggaaagag   5160
tcaaatggct ctcctcaagc gtattcaaca aggggctgaa ggatgcccag aaggtacccc   5220
attgtatggg atctgatctg gggcctcggt gcacatgctt tacatgtgtt tagtcgaggt   5280
taaaaaaacg tctaggcccc ccgaaccacg gggacgtggt tttcctttga aaaacacgat   5340
gataatatgg ccacaaccat gaccgagtac aagcccacgg tgcgcctcgc cacccgcgac   5400
gacgtcccca gggccgtacg caccctcgcc gccgcgttcg ccgactaccc cgccacgcgc   5460
cacaccgtcg atccggaccg ccacatcgag cgggtcaccg agctgcaaga actcttcctc   5520
acgcgcgtcg ggctcgacat cggcaaggtg tgggtcgcgg acgacggcgc cgcggtggcg   5580
gtctggacca cgccggagag cgtcgaagcg ggggcggtgt tcgccgagat cggcccgcgc   5640
atggccgagt tgagcggttc ccggctggcc gcgcagcaac agatggaagg cctcctggcg   5700
ccgcaccggc ccaaggagcc cgcgtggttc ctggccaccg tcggcgtctc gcccgaccac   5760
cagggcaagg gtctgggcag cgccgtcgtg ctccccggag tggaggcggc cgagcgcgcc   5820
ggggtgcccg ccttcctgga gacctccgcg ccccgcaacc tccccttcta cgagcggctc   5880
ggcttcaccg tcaccgccga cgtcgaggtg cccgaaggac cgcgcacctg gtgcatgacc   5940
cgcaagcccg gtgcctgacg cccgccccac gacccgcagc gcccgaccga aaggagcgca   6000
cgaccccatg catcgatgat ctagagctcg ctgatcagcc tcgactgtgc cttctagttg   6060
ccagccatct gttgtttgcc cctcccccgt gccttccttg accctggaag gtgccactcc   6120
cactgtcctt tcctaataaa atgaggaaat tgcatcgcat tgtctgagta ggtgtcattc   6180
tattctgggg ggtggggtgg ggcaggacag caagggggag gattgggaag acaatagcag   6240
gcatgctggg gatgcggtgg gctctatggc ttctgaggcg gaaagaacct gcagcccaag   6300
cttggcgtaa tcatggtcat agctgtttcc tgtgtgaaat tgttatccgc tcacaattcc   6360
acacaacata cgagccggaa gcataaagtg taaagcctgg ggtgcctaat gagtgagcta   6420
actcacatta attgcgttgc gctcactgcc cgctttccag tcgggaaacc tgtcgtgcca   6480
gcggatccgc atctcaatta gtcagcaacc atagtcccgc ccctaactcc gcccatcccg   6540
cccctaactc cgcccagttc cgcccattct ccgccccatg gctgactaat tttttttatt   6600
tatgcagagg ccgaggccgc ctcggcctct gagctattcc agaagtagtg aggaggcttt   6660
tttggaggcc taggcttttg caaaaagcta acttgtttat tgcagcttat aatggttaca   6720
aataaagcaa tagcatcaca aatttcacaa ataaagcatt tttttcactg cattctagtt   6780
gtggtttgtc caaactcatc aatgtatctt atcatgtctg gatccgctgc attaatgaat   6840
cggccaacgc gcggggagag gcggtttgcg tattgggcgc tcttccgctt cctcgctcac   6900
tgactcgctg cgctcggtcg ttcggctgcg gcgagcggta tcagctcact caaaggcggt   6960
aatacggtta tccacagaat caggggataa cgcaggaaag aacatgtgag caaaaggcca   7020
gcaaaaggcc aggaaccgta aaaaggccgc gttgctggcg tttttccata ggctccgccc   7080
ccctgacgag catcacaaaa atcgacgctc aagtcagagg tggcgaaacc cgacaggact   7140
ataaagatac caggcgtttc cccctggaag ctccctcgtg cgctctcctg ttccgaccct   7200
```

```
gccgcttacc ggatacctgt ccgcctttct cccttcggga agcgtggcgc tttctcatag   7260

ctcacgctgt aggtatctca gttcggtgta ggtcgttcgc tccaagctgg gctgtgtgca   7320

cgaacccccc gttcagcccg accgctgcgc cttatccggt aactatcgtc ttgagtccaa   7380

cccggtaaga cacgacttat cgccactggc agcagccact ggtaacagga ttagcagagc   7440

gaggtatgta ggcggtgcta cagagttctt gaagtggtgg cctaactacg gctacactag   7500

aagaacagta tttggtatct gcgctctgct gaagccagtt accttcggaa aaagagttgg   7560

tagctcttga tccggcaaac aaaccaccgc tggtagcggt ggtttttttg tttgcaagca   7620

gcagattacg cgcagaaaaa aaggatctca agaagatcct ttgatctttt ctacggggtc   7680

tgacgctcag tggaacgaaa actcacgtta agggattttg gtcatgagat tatcaaaaag   7740

gatcttcacc tagatccttt taaattaaaa atgaagtttt aaatcaatct aaagtatata   7800

tgagtaaact tggtctgaca gttaccaatg cttaatcagt gaggcaccta tctcagcgat   7860

ctgtctattt cgttcatcca tagttgcctg actccccgtc gtgtagataa ctacgatacg   7920

ggagggctta ccatctggcc ccagtgctgc aatgataccg cgagacccac gctcaccggc   7980

tccagattta tcagcaataa accagccagc cggaagggcc gagcgcagaa gtggtcctgc   8040

aactttatcc gcctccatcc agtctattaa ttgttgccgg gaagctagag taagtagttc   8100

gccagttaat agtttgcgca acgttgttgc cattgctaca ggcatcgtgg tgtcacgctc   8160

gtcgtttggt atggcttcat tcagctccgg ttcccaacga tcaaggcgag ttacatgatc   8220

ccccatgttg tgcaaaaaag cggttagctc cttcggtcct ccgatcgttg tcagaagtaa   8280

gttggccgca gtgttatcac tcatggttat ggcagcactg cataattctc ttactgtcat   8340

gccatccgta agatgctttt ctgtgactgg tgagtactca accaagtcat tctgagaata   8400

gtgtatgcgg cgaccgagtt gctcttgccc ggcgtcaata cgggataata ccgcgccaca   8460

tagcagaact ttaaaagtgc tcatcattgg aaaacgttct tcggggcgaa aactctcaag   8520

gatcttaccg ctgttgagat ccagttcgat gtaacccact cgtgcaccca actgatcttc   8580

agcatctttt actttcacca gcgtttctgg gtgagcaaaa acaggaaggc aaaatgccgc   8640

aaaaaaggga ataagggcga cacggaaatg ttgaatactc atactcttcc tttttcaat    8699
```

<210> SEQ ID NO 21
<211> LENGTH: 315
<212> TYPE: PRT
<213> ORGANISM: Artificial Sequence
<220> FEATURE:
<223> OTHER INFORMATION: Recombinant polypeptide (ERT2)

<400> SEQUENCE: 21

```
Pro Ser Ala Gly Asp Met Arg Ala Ala Asn Leu Trp Pro Ser Pro Leu
1               5                   10                  15

Met Ile Lys Arg Ser Lys Lys Asn Ser Leu Ala Leu Ser Leu Thr Ala
            20                  25                  30

Asp Gln Met Val Ser Ala Leu Leu Asp Ala Glu Pro Pro Ile Leu Tyr
        35                  40                  45

Ser Glu Tyr Asp Pro Thr Arg Pro Phe Ser Glu Ala Ser Met Met Gly
    50                  55                  60

Leu Leu Thr Asn Leu Ala Asp Arg Glu Leu Val His Met Ile Asn Trp
65                  70                  75                  80

Ala Lys Arg Val Pro Gly Phe Val Asp Leu Thr Leu His Asp Gln Val
                85                  90                  95
```

-continued

```
His Leu Leu Glu Cys Ala Trp Leu Glu Ile Leu Met Ile Gly Leu Val
            100                 105                 110

Trp Arg Ser Met Glu His Pro Val Lys Leu Leu Phe Ala Pro Asn Leu
        115                 120                 125

Leu Leu Asp Arg Asn Gln Gly Lys Cys Val Glu Gly Met Val Glu Ile
    130                 135                 140

Phe Asp Met Leu Leu Ala Thr Ser Ser Arg Phe Arg Met Met Asn Leu
145                 150                 155                 160

Gln Gly Glu Glu Phe Val Cys Leu Lys Ser Ile Ile Leu Leu Asn Ser
                165                 170                 175

Gly Val Tyr Thr Phe Leu Ser Ser Thr Leu Lys Ser Leu Glu Glu Lys
            180                 185                 190

Asp His Ile His Arg Val Leu Asp Lys Ile Thr Asp Thr Leu Ile His
        195                 200                 205

Leu Met Ala Lys Ala Gly Leu Thr Leu Gln Gln Gln His Gln Arg Leu
    210                 215                 220

Ala Gln Leu Leu Leu Ile Leu Ser His Ile Arg His Met Ser Asn Lys
225                 230                 235                 240

Gly Met Glu His Leu Tyr Ser Met Lys Cys Lys Asn Val Val Pro Leu
                245                 250                 255

Tyr Asp Leu Leu Leu Glu Ala Ala Asp Ala His Arg Leu His Ala Pro
            260                 265                 270

Thr Ser Arg Gly Gly Ala Ser Val Glu Glu Thr Asp Gln Ser His Leu
        275                 280                 285

Ala Thr Ala Gly Ser Thr Ser Ser His Ser Leu Gln Lys Tyr Tyr Ile
    290                 295                 300

Thr Gly Glu Ala Glu Gly Phe Pro Ala Thr Ala
305                 310                 315


<210> SEQ ID NO 22
<211> LENGTH: 823
<212> TYPE: PRT
<213> ORGANISM: Artificial Sequence
<220> FEATURE:
<223> OTHER INFORMATION: Recombinant protein (Zscan4c-ERT2)

<400> SEQUENCE: 22

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80

Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140
```

-continued

```
Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu Tyr Lys Cys Glu Glu Cys
385                 390                 395                 400

Ser Arg Met Phe Lys His Ala Arg Ser Leu Ser Ser His Gln Arg Thr
                405                 410                 415

His Leu Asn Lys Lys Ser Glu Leu Leu Cys Val Thr Cys Gln Lys Met
            420                 425                 430

Phe Lys Arg Val Ser Asp Arg Arg Thr His Glu Ile Ile His Met Pro
        435                 440                 445

Glu Lys Pro Phe Lys Cys Ser Thr Cys Glu Lys Ser Phe Ser His Lys
    450                 455                 460

Thr Asn Leu Lys Ser His Glu Met Ile His Thr Gly Glu Met Pro Tyr
465                 470                 475                 480

Val Cys Ser Leu Cys Ser Arg Arg Phe Arg Gln Ser Ser Thr Tyr His
                485                 490                 495

Arg His Leu Arg Asn Tyr His Arg Ser Asp Ala Ser Pro Ser Ala Gly
            500                 505                 510

Asp Met Arg Ala Ala Asn Leu Trp Pro Ser Pro Leu Met Ile Lys Arg
        515                 520                 525

Ser Lys Lys Asn Ser Leu Ala Leu Ser Leu Thr Ala Asp Gln Met Val
    530                 535                 540

Ser Ala Leu Leu Asp Ala Glu Pro Pro Ile Leu Tyr Ser Glu Tyr Asp
545                 550                 555                 560

Pro Thr Arg Pro Phe Ser Glu Ala Ser Met Met Gly Leu Leu Thr Asn
```

```
                565                 570                 575

Leu Ala Asp Arg Glu Leu Val His Met Ile Asn Trp Ala Lys Arg Val
            580                 585                 590

Pro Gly Phe Val Asp Leu Thr Leu His Asp Gln Val His Leu Leu Glu
        595                 600                 605

Cys Ala Trp Leu Glu Ile Leu Met Ile Gly Leu Val Trp Arg Ser Met
    610                 615                 620

Glu His Pro Val Lys Leu Leu Phe Ala Pro Asn Leu Leu Leu Asp Arg
625                 630                 635                 640

Asn Gln Gly Lys Cys Val Glu Gly Met Val Glu Ile Phe Asp Met Leu
                645                 650                 655

Leu Ala Thr Ser Ser Arg Phe Arg Met Met Asn Leu Gln Gly Glu Glu
            660                 665                 670

Phe Val Cys Leu Lys Ser Ile Ile Leu Leu Asn Ser Gly Val Tyr Thr
        675                 680                 685

Phe Leu Ser Ser Thr Leu Lys Ser Leu Glu Glu Lys Asp His Ile His
    690                 695                 700

Arg Val Leu Asp Lys Ile Thr Asp Thr Leu Ile His Leu Met Ala Lys
705                 710                 715                 720

Ala Gly Leu Thr Leu Gln Gln Gln His Gln Arg Leu Ala Gln Leu Leu
                725                 730                 735

Leu Ile Leu Ser His Ile Arg His Met Ser Asn Lys Gly Met Glu His
            740                 745                 750

Leu Tyr Ser Met Lys Cys Lys Asn Val Val Pro Leu Tyr Asp Leu Leu
        755                 760                 765

Leu Glu Ala Ala Asp Ala His Arg Leu His Ala Pro Thr Ser Arg Gly
    770                 775                 780

Gly Ala Ser Val Glu Glu Thr Asp Gln Ser His Leu Ala Thr Ala Gly
785                 790                 795                 800

Ser Thr Ser Ser His Ser Leu Gln Lys Tyr Tyr Ile Thr Gly Glu Ala
                805                 810                 815

Glu Gly Phe Pro Ala Thr Ala
            820


<210> SEQ ID NO 23
<211> LENGTH: 750
<212> TYPE: PRT
<213> ORGANISM: Artificial Sequence
<220> FEATURE:
<223> OTHER INFORMATION: Recombinant protein (ZSCAN4-ERT2)

<400> SEQUENCE: 23

Met Ala Leu Asp Leu Arg Thr Ile Phe Gln Cys Glu Pro Ser Glu Asn
1               5                   10                  15

Asn Leu Gly Ser Glu Asn Ser Ala Phe Gln Gln Ser Gln Gly Pro Ala
            20                  25                  30

Val Gln Arg Glu Glu Gly Ile Ser Glu Phe Ser Arg Met Val Leu Asn
        35                  40                  45

Ser Phe Gln Asp Ser Asn Asn Ser Tyr Ala Arg Gln Glu Leu Gln Arg
    50                  55                  60

Leu Tyr Arg Ile Phe His Ser Trp Leu Gln Pro Glu Lys His Ser Lys
65                  70                  75                  80

Asp Glu Ile Ile Ser Leu Leu Val Leu Glu Gln Phe Met Ile Gly Gly
                85                  90                  95

His Cys Asn Asp Lys Ala Ser Val Lys Glu Lys Trp Lys Ser Ser Gly
```

-continued

```
            100                 105                 110

Lys Asn Leu Glu Arg Phe Ile Glu Asp Leu Thr Asp Asp Ser Ile Asn
        115                 120                 125

Pro Pro Ala Leu Val His Val His Met Gln Gly Gln Glu Ala Leu Phe
    130                 135                 140

Ser Glu Asp Met Pro Leu Arg Asp Val Ile Val His Leu Thr Lys Gln
145                 150                 155                 160

Val Asn Ala Gln Thr Thr Arg Glu Ala Asn Met Gly Thr Pro Ser Gln
                165                 170                 175

Thr Ser Gln Asp Thr Ser Leu Glu Thr Gly Gln Gly Tyr Glu Asp Glu
            180                 185                 190

Gln Asp Gly Trp Asn Ser Ser Ser Lys Thr Thr Arg Val Asn Glu Asn
        195                 200                 205

Ile Thr Asn Gln Gly Asn Gln Ile Val Ser Leu Ile Ile Ile Gln Glu
    210                 215                 220

Glu Asn Gly Pro Arg Pro Glu Glu Gly Gly Val Ser Ser Asp Asn Pro
225                 230                 235                 240

Tyr Asn Ser Lys Arg Ala Glu Leu Val Thr Ala Arg Ser Gln Glu Gly
                245                 250                 255

Ser Ile Asn Gly Ile Thr Phe Gln Gly Val Pro Met Val Met Gly Ala
            260                 265                 270

Gly Cys Ile Ser Gln Pro Glu Gln Ser Ser Pro Glu Ser Ala Leu Thr
        275                 280                 285

His Gln Ser Asn Glu Gly Asn Ser Thr Cys Glu Val His Gln Lys Gly
    290                 295                 300

Ser His Gly Val Gln Lys Ser Tyr Lys Cys Glu Glu Cys Pro Lys Val
305                 310                 315                 320

Phe Lys Tyr Leu Cys His Leu Leu Ala His Gln Arg Arg His Arg Asn
                325                 330                 335

Glu Arg Pro Phe Val Cys Pro Glu Cys Gln Lys Gly Phe Phe Gln Ile
            340                 345                 350

Ser Asp Leu Arg Val His Gln Ile Ile His Thr Gly Lys Lys Pro Phe
        355                 360                 365

Thr Cys Ser Met Cys Lys Lys Ser Phe Ser His Lys Thr Asn Leu Arg
    370                 375                 380

Ser His Glu Arg Ile His Thr Gly Glu Lys Pro Tyr Thr Cys Pro Phe
385                 390                 395                 400

Cys Lys Thr Ser Tyr Arg Gln Ser Ser Thr Tyr His Arg His Met Arg
                405                 410                 415

Thr His Glu Lys Ile Thr Leu Pro Ser Val Pro Ser Thr Pro Glu Ala
            420                 425                 430

Ser Ala Ser Pro Ser Ala Gly Asp Met Arg Ala Ala Asn Leu Trp Pro
        435                 440                 445

Ser Pro Leu Met Ile Lys Arg Ser Lys Lys Asn Ser Leu Ala Leu Ser
    450                 455                 460

Leu Thr Ala Asp Gln Met Val Ser Ala Leu Leu Asp Ala Glu Pro Pro
465                 470                 475                 480

Ile Leu Tyr Ser Glu Tyr Asp Pro Thr Arg Pro Phe Ser Glu Ala Ser
                485                 490                 495

Met Met Gly Leu Leu Thr Asn Leu Ala Asp Arg Glu Leu Val His Met
            500                 505                 510

Ile Asn Trp Ala Lys Arg Val Pro Gly Phe Val Asp Leu Thr Leu His
        515                 520                 525
```

```
Asp Gln Val His Leu Leu Glu Cys Ala Trp Leu Glu Ile Leu Met Ile
    530                 535                 540

Gly Leu Val Trp Arg Ser Met Glu His Pro Val Lys Leu Leu Phe Ala
545                 550                 555                 560

Pro Asn Leu Leu Leu Asp Arg Asn Gln Gly Lys Cys Val Glu Gly Met
                565                 570                 575

Val Glu Ile Phe Asp Met Leu Leu Ala Thr Ser Ser Arg Phe Arg Met
            580                 585                 590

Met Asn Leu Gln Gly Glu Glu Phe Val Cys Leu Lys Ser Ile Ile Leu
        595                 600                 605

Leu Asn Ser Gly Val Tyr Thr Phe Leu Ser Ser Thr Leu Lys Ser Leu
    610                 615                 620

Glu Glu Lys Asp His Ile His Arg Val Leu Asp Lys Ile Thr Asp Thr
625                 630                 635                 640

Leu Ile His Leu Met Ala Lys Ala Gly Leu Thr Leu Gln Gln Gln His
                645                 650                 655

Gln Arg Leu Ala Gln Leu Leu Leu Ile Leu Ser His Ile Arg His Met
            660                 665                 670

Ser Asn Lys Gly Met Glu His Leu Tyr Ser Met Lys Cys Lys Asn Val
        675                 680                 685

Val Pro Leu Tyr Asp Leu Leu Leu Glu Ala Ala Asp Ala His Arg Leu
    690                 695                 700

His Ala Pro Thr Ser Arg Gly Gly Ala Ser Val Glu Glu Thr Asp Gln
705                 710                 715                 720

Ser His Leu Ala Thr Ala Gly Ser Thr Ser Ser His Ser Leu Gln Lys
                725                 730                 735

Tyr Tyr Ile Thr Gly Glu Ala Glu Gly Phe Pro Ala Thr Ala
            740                 745                 750
```

<210> SEQ ID NO 24
<211> LENGTH: 7617
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (2465)..(3649)
<223> OTHER INFORMATION: Zscan4c-deltaC

<400> SEQUENCE: 24

```
gaccgctttg gaaaaacaaa gactgtattt cctggaaatt aatgtttatt caataaactg     60

tgtattcagc tatattcaca tagtggtgag gctgaaatga ggcgggaaga ggcggttggg    120

gcttaattat atcaatttgg gtggccccac agcgcctcca aggcgccagt cctgttttga    180

caagttgcct ctggaagcct ctcttctttt tctccagagt aagcggaggc caggggcccc    240

cggcctctgc ttaatactaa aaaaaacagc tgttgtcata gtaatgattg ggtggaaaca    300

ttccaggcct gggtggagag gctttttgct tcctcttgca aaaccacact gacattccag    360

gcctgggtgg agaggctttt tgcttcctct tgcaaaacca cactgccctc tggagggcag    420

ttgcctagca actaattaaa agaggatgtc gcacggccag ctgcggtcag ttagtcactt    480

cctgcttaac tgacttgaca ttttctattt taagagtcgg gaggaaaatt actgtgttgg    540

aggccctccg ccatcttctg aagctgaatc gaattaactt gtttattgca gcttataatg    600

gttacaaata aagcaatagc atcacaaatt tcacaaataa agcatttttt tcactgcatt    660
```

-continued

```
ctagttgtgg tttgtccaaa ctcatcaatg tatcttatca tgtctggatc tgatatcatc    720

gtcgacattg attattgact agttattaat agtaatcaat tacggggtca ttagttcata    780

gcccatatat ggagttccgc gttacataac ttacggtaaa tggcccgcct ggctgaccgc    840

ccaacgaccc ccgcccattg acgtcaataa tgacgtatgt tcccatagta acgccaatag    900

ggactttcca ttgacgtcaa tgggtggagt atttacggta aactgcccac ttggcagtac    960

atcaagtgta tcatatgcca agtacgcccc ctattgacgt caatgacggt aaatggcccg   1020

cctggcatta tgcccagtac atgaccttat gggactttcc tacttggcag tacatctacg   1080

tattagtcat cgctattacc atggtcgagg tgagccccac gttctgcttc actctcccca   1140

tctccccccc ctccccaccc ccaattttgt atttatttat tttttaatta ttttgtgcag   1200

cgatgggggc gggggggggg gggggcgcg cgccaggcgg ggcggggcgg ggcgaggggc   1260

ggggcggggc gaggcggaga ggtgcggcgg cagccaatca gagcggcgcg ctccgaaagt   1320

ttccttttat ggcgaggcgg cggcggcggc ggccctataa aaagcgaagc gcgcggcggg   1380

cgggagtcgc tgcgcgctgc cttcgccccg tgccccgctc cgccgccgcc tcgcgccgcc   1440

cgccccggct ctgactgacc gcgttactcc cacaggtgag cgggcgggac ggcccttctc   1500

ctccgggctg taattagcgc ttggtttaat gacggcttgt ttcttttctg tggctgcgtg   1560

aaagccttga ggggctccgg gagggccctt tgtgcggggg gagcggctcg gggggtgcgt   1620

gcgtgtgtgt gtgcgtgggg agcgccgcgt gcggctccgc gctgcccggc ggctgtgagc   1680

gctgcgggcg cggcgcgggg ctttgtgcgc tccgcagtgt gcgcgagggg agcgcggccg   1740

ggggcggtgc cccgcggtgc ggggggggct gcgaggggaa caaaggctgc gtgcggggtg   1800

tgtgcgtggg ggggtgagca gggggtgtgg gcgcgtcggt cgggctgcaa ccccccctgc   1860

acccccctcc ccgagttgct gagcacggcc cggcttcggg tgcggggctc cgtacggggc   1920

gtggcgcggg gctcgccgtg ccgggcgggg ggtggcggca ggtgggggtg ccgggcgggg   1980

cggggccgcc tcgggccggg gagggctcgg gggagggcg cggcggcccc cggagcgccg   2040

gcggctgtcg aggcgcggcg agccgcagcc attgcctttt atggtaatcg tgcgagaggg   2100

cgcagggact tcctttgtcc caaatctgtg cggagccgaa atctgggagg cgccgccgca   2160

ccccctctag cgggcgcggg gcgaagcggt gcggcgccgg caggaaggaa atgggcgggg   2220

agggccttcg tgcgtcgccg cgccgccgtc cccttctccc tctccagcct cggggctgtc   2280

cgcgggggga cggctgcctt cgggggggac ggggcagggc ggggttcggc ttctggcgtg   2340

tgaccggcgg ctctagagcc tctgctaacc atgttcatgc cttcttcttt ttcctacagc   2400

tcctgggcaa cgtgctggtt attgtgctgt ctcatcattt tggcaaagaa ttcctcgagc   2460

cacc atg gct tca cag cag gca cca gca aaa gac ctt cag acc aac aat     2509
     Met Ala Ser Gln Gln Ala Pro Ala Lys Asp Leu Gln Thr Asn Asn
     1               5                   10                  15

tta gag ttt act cca act gat agt tct ggt gtg cag tgg gca gaa gac      2557
Leu Glu Phe Thr Pro Thr Asp Ser Ser Gly Val Gln Trp Ala Glu Asp
                20                  25                  30

atc tct aac tca cca agt gct cag cta aac ttt tcc cca agt aac aat      2605
Ile Ser Asn Ser Pro Ser Ala Gln Leu Asn Phe Ser Pro Ser Asn Asn
            35                  40                  45

ggc tgc tgg gca act cag gag ctg caa agt ctc tgg aag atg ttc aac      2653
Gly Cys Trp Ala Thr Gln Glu Leu Gln Ser Leu Trp Lys Met Phe Asn
        50                  55                  60

tcc tgg ttg cag cca gaa aag cag act aag gag cag atg att tct caa      2701
Ser Trp Leu Gln Pro Glu Lys Gln Thr Lys Glu Gln Met Ile Ser Gln
    65                  70                  75
```

-continued

```
ctg gtc ttg gag cag ttt ctc ctc act ggg cac tgc aag gac aag tat      2749
Leu Val Leu Glu Gln Phe Leu Leu Thr Gly His Cys Lys Asp Lys Tyr
80                  85                  90                  95

gct ttg aca gag aag tgg aaa gcc agt ggt agc gat atg agg aga ttc      2797
Ala Leu Thr Glu Lys Trp Lys Ala Ser Gly Ser Asp Met Arg Arg Phe
                100                 105                 110

atg gag agt ctg act gat gag tgc ttg aag cct cct gtc atg gtc cat      2845
Met Glu Ser Leu Thr Asp Glu Cys Leu Lys Pro Pro Val Met Val His
            115                 120                 125

gtt tca atg caa gga caa gaa gcc ctc ttt tct gaa aac atg cca tta      2893
Val Ser Met Gln Gly Gln Glu Ala Leu Phe Ser Glu Asn Met Pro Leu
        130                 135                 140

aaa gaa gtc atc aag ctt ttg aaa caa cag caa tct gca aca agg cca      2941
Lys Glu Val Ile Lys Leu Leu Lys Gln Gln Gln Ser Ala Thr Arg Pro
    145                 150                 155

aca cca gat aat gag cag atg cca gta gac acc aca caa gat aga tta      2989
Thr Pro Asp Asn Glu Gln Met Pro Val Asp Thr Thr Gln Asp Arg Leu
160                 165                 170                 175

ttg gcc aca gga caa gaa aac agt gaa aat gaa tgc aac aac tct tgt      3037
Leu Ala Thr Gly Gln Glu Asn Ser Glu Asn Glu Cys Asn Asn Ser Cys
                180                 185                 190

aat gct act gaa gca aat gtt ggt gaa agc tgt agt gga aat gaa atg      3085
Asn Ala Thr Glu Ala Asn Val Gly Glu Ser Cys Ser Gly Asn Glu Met
            195                 200                 205

gac tcc ctt ctt att atc cag aaa gaa cag cac cct gag cat gaa gag      3133
Asp Ser Leu Leu Ile Ile Gln Lys Glu Gln His Pro Glu His Glu Glu
        210                 215                 220

ggg aat gtt gtt tgt caa ttc cct cat ggt gcc aga aga gca agt caa      3181
Gly Asn Val Val Cys Gln Phe Pro His Gly Ala Arg Arg Ala Ser Gln
    225                 230                 235

ggc acc ccc agt cat cat gta gac ttc ccg agt gct ccg act act gcc      3229
Gly Thr Pro Ser His His Val Asp Phe Pro Ser Ala Pro Thr Thr Ala
240                 245                 250                 255

gat gtc ccc atg gag gaa caa cca aag gat tta tcc aga gaa aac atc      3277
Asp Val Pro Met Glu Glu Gln Pro Lys Asp Leu Ser Arg Glu Asn Ile
                260                 265                 270

tct gag gac aag aac aat tgc tat aac act tcc aga aat gca gct act      3325
Ser Glu Asp Lys Asn Asn Cys Tyr Asn Thr Ser Arg Asn Ala Ala Thr
            275                 280                 285

caa gta tat agt ggt gat aat att ccc agg aac aag tca gac tcc ctt      3373
Gln Val Tyr Ser Gly Asp Asn Ile Pro Arg Asn Lys Ser Asp Ser Leu
        290                 295                 300

ttc att aac aag aga ata tat cat cct gag cct gag gtg gga gat att      3421
Phe Ile Asn Lys Arg Ile Tyr His Pro Glu Pro Glu Val Gly Asp Ile
    305                 310                 315

cct tat gga gtt cct cag gat tct aca aga gca agt caa gga aca tct      3469
Pro Tyr Gly Val Pro Gln Asp Ser Thr Arg Ala Ser Gln Gly Thr Ser
320                 325                 330                 335

aca tgc ctg caa gag tca ctt ggg gaa tgt ttt tct gaa aac gac cca      3517
Thr Cys Leu Gln Glu Ser Leu Gly Glu Cys Phe Ser Glu Asn Asp Pro
                340                 345                 350

agg gag gta cca ggg ttg cag tct agg caa gag cag cct atc tct gat      3565
Arg Glu Val Pro Gly Leu Gln Ser Arg Gln Glu Gln Pro Ile Ser Asp
            355                 360                 365

cct gtc ctt ctt ggt aag aat cat gag gca aac tta cca tgt gaa agt      3613
Pro Val Leu Leu Gly Lys Asn His Glu Ala Asn Leu Pro Cys Glu Ser
        370                 375                 380

cat caa aag aga ttc tgt aga gat gcc aaa cta tga gcggccgctc           3659
His Gln Lys Arg Phe Cys Arg Asp Ala Lys Leu
```

385 390 gataagcttg atatcgaatt ccgccccccc cccctctccc tccccccccc ctaacgttac 3719 tggccgaagc cgcttggaat aaggccggtg tgcgtttgtc tatatgttat tttccaccat 3779 attgccgtct tttggcaatg tgagggcccg gaaacctggc cctgtcttct tgacgagcat 3839 tcctaggggt ctttcccctc tcgccaaagg aatgcaaggt ctgttgaatg tcgtgaagga 3899 agcagttcct ctggaagctt cttgaagaca aacaacgtct gtagcgaccc tttgcaggca 3959 gcggaacccc ccacctggcg acaggtgcct ctgcggccaa aagccacgtg tataagatac 4019 acctgcaaag gcggcacaac cccagtgcca cgttgtgagt tggatagttg tggaaagagt 4079 caaatggctc tcctcaagcg tattcaacaa ggggctgaag gatgcccaga aggtacccca 4139 ttgtatggga tctgatctgg ggcctcggtg cacatgcttt acatgtgttt agtcgaggtt 4199 aaaaaaacgt ctaggccccc cgaaccacgg ggacgtggtt ttcctttgaa aaacacgatg 4259 ataatatggc cacaaccatg accgagtaca agcccacggt gcgcctcgcc acccgcgacg 4319 acgtccccag ggccgtacgc accctcgccg ccgcgttcgc cgactacccc gccacgcgcc 4379 acaccgtcga tccggaccgc cacatcgagc gggtcaccga gctgcaagaa ctcttcctca 4439 cgcgcgtcgg gctcgacatc ggcaaggtgt gggtcgcgga cgacggcgcc gcggtggcgg 4499 tctggaccac gccggagagc gtcgaagcgg gggcggtgtt cgccgagatc ggcccgcgca 4559 tggccgagtt gagcggttcc cggctggccg cgcagcaaca gatggaaggc ctcctggcgc 4619 cgcaccggcc caaggagccc gcgtggttcc tggccaccgt cggcgtctcg cccgaccacc 4679 agggcaaggg tctgggcagc gccgtcgtgc tccccggagt ggaggcggcc gagcgcgccg 4739 gggtgcccgc cttcctggag acctccgcgc cccgcaacct ccccttctac gagcggctcg 4799 gcttcaccgt caccgccgac gtcgaggtgc ccgaaggacc gcgcacctgg tgcatgaccc 4859 gcaagcccgg tgcctgacgc ccgccccacg acccgcagcg cccgaccgaa aggagcgcac 4919 gaccccatgc atcgatgatc tagagctcgc tgatcagcct cgactgtgcc ttctagttgc 4979 cagccatctg ttgtttgccc ctcccccgtg ccttccttga ccctggaagg tgccactccc 5039 actgtccttt cctaataaaa tgaggaaatt gcatcgcatt gtctgagtag gtgtcattct 5099 attctggggg gtggggtggg gcaggacagc aagggggagg attgggaaga caatagcagg 5159 catgctgggg atgcggtggg ctctatggct tctgaggcgg aaagaacctg cagcccaagc 5219 ttggcgtaat catggtcata gctgtttcct gtgtgaaatt gttatccgct cacaattcca 5279 cacaacatac gagccggaag cataaagtgt aaagcctggg gtgcctaatg agtgagctaa 5339 ctcacattaa ttgcgttgcg ctcactgccc gctttccagt cgggaaacct gtcgtgccag 5399 cggatccgca tctcaattag tcagcaacca tagtcccgcc cctaactccg cccatcccgc 5459 ccctaactcc gcccagttcc gcccattctc cgccccatgg ctgactaatt ttttttattt 5519 atgcagaggc cgaggccgcc tcggcctctg agctattcca gaagtagtga ggaggctttt 5579 ttggaggcct aggcttttgc aaaaagctaa cttgtttatt gcagcttata atggttacaa 5639 ataaagcaat agcatcacaa atttcacaaa taaagcattt ttttcactgc attctagttg 5699 tggtttgtcc aaactcatca atgtatctta tcatgtctgg atccgctgca ttaatgaatc 5759 ggccaacgcg cggggagagg cggtttgcgt attgggcgct cttccgcttc ctcgctcact 5819 gactcgctgc gctcggtcgt tcggctgcgg cgagcggtat cagctcactc aaaggcggta 5879 atacggttat ccacagaatc aggggataac gcaggaaaga acatgtgagc aaaaggccag 5939 caaaaggcca ggaaccgtaa aaaggccgcg ttgctggcgt ttttccatag gctccgcccc 5999

-continued

```
cctgacgagc atcacaaaaa tcgacgctca agtcagaggt ggcgaaaccc gacaggacta   6059

taaagatacc aggcgtttcc ccctggaagc tccctcgtgc gctctcctgt tccgaccctg   6119

ccgcttaccg gatacctgtc cgcctttctc ccttcgggaa gcgtggcgct ttctcatagc   6179

tcacgctgta ggtatctcag ttcggtgtag gtcgttcgct ccaagctggg ctgtgtgcac   6239

gaaccccccg ttcagcccga ccgctgcgcc ttatccggta actatcgtct tgagtccaac   6299

ccggtaagac acgacttatc gccactggca gcagccactg gtaacaggat tagcagagcg   6359

aggtatgtag gcggtgctac agagttcttg aagtggtggc ctaactacgg ctacactaga   6419

agaacagtat ttggtatctg cgctctgctg aagccagtta ccttcggaaa aagagttggt   6479

agctcttgat ccggcaaaca aaccaccgct ggtagcggtg gtttttttgt ttgcaagcag   6539

cagattacgc gcagaaaaaa aggatctcaa gaagatcctt tgatcttttc tacggggtct   6599

gacgctcagt ggaacgaaaa ctcacgttaa gggattttgg tcatgagatt atcaaaaagg   6659

atcttcacct agatcctttt aaattaaaaa tgaagtttta aatcaatcta aagtatatat   6719

gagtaaactt ggtctgacag ttaccaatgc ttaatcagtg aggcacctat ctcagcgatc   6779

tgtctatttc gttcatccat agttgcctga ctccccgtcg tgtagataac tacgatacgg   6839

gagggcttac catctggccc cagtgctgca atgataccgc gagacccacg ctcaccggct   6899

ccagatttat cagcaataaa ccagccagcc ggaagggccg agcgcagaag tggtcctgca   6959

actttatccg cctccatcca gtctattaat tgttgccggg aagctagagt aagtagttcg   7019

ccagttaata gtttgcgcaa cgttgttgcc attgctacag gcatcgtggt gtcacgctcg   7079

tcgtttggta tggcttcatt cagctccggt tcccaacgat caaggcgagt tacatgatcc   7139

cccatgttgt gcaaaaaagc ggttagctcc ttcggtcctc cgatcgttgt cagaagtaag   7199

ttggccgcag tgttatcact catggttatg gcagcactgc ataattctct tactgtcatg   7259

ccatccgtaa gatgcttttc tgtgactggt gagtactcaa ccaagtcatt ctgagaatag   7319

tgtatgcggc gaccgagttg ctcttgcccg gcgtcaatac gggataatac cgcgccacat   7379

agcagaactt taaaagtgct catcattgga aaacgttctt cggggcgaaa actctcaagg   7439

atcttaccgc tgttgagatc cagttcgatg taacccactc gtgcacccaa ctgatcttca   7499

gcatctttta ctttcaccag cgtttctggg tgagcaaaaa caggaaggca aaatgccgca   7559

aaaaagggaa taagggcgac acggaaatgt tgaatactca tactcttcct ttttcaat     7617
```

```
<210> SEQ ID NO 25
<211> LENGTH: 394
<212> TYPE: PRT
<213> ORGANISM: Artificial Sequence
<220> FEATURE:
<223> OTHER INFORMATION: Synthetic Construct

<400> SEQUENCE: 25

Met Ala Ser Gln Gln Ala Pro Ala Lys Asp Leu Gln Thr Asn Asn Leu
1               5                   10                  15

Glu Phe Thr Pro Thr Asp Ser Ser Gly Val Gln Trp Ala Glu Asp Ile
            20                  25                  30

Ser Asn Ser Pro Ser Ala Gln Leu Asn Phe Ser Pro Ser Asn Asn Gly
        35                  40                  45

Cys Trp Ala Thr Gln Glu Leu Gln Ser Leu Trp Lys Met Phe Asn Ser
    50                  55                  60

Trp Leu Gln Pro Glu Lys Gln Thr Lys Glu Gln Met Ile Ser Gln Leu
65                  70                  75                  80
```

-continued

```
Val Leu Glu Gln Phe Leu Leu Thr Gly His Cys Lys Asp Lys Tyr Ala
                85                  90                  95

Leu Thr Glu Lys Trp Lys Ala Ser Gly Ser Asp Met Arg Arg Phe Met
            100                 105                 110

Glu Ser Leu Thr Asp Glu Cys Leu Lys Pro Pro Val Met Val His Val
        115                 120                 125

Ser Met Gln Gly Gln Glu Ala Leu Phe Ser Glu Asn Met Pro Leu Lys
    130                 135                 140

Glu Val Ile Lys Leu Leu Lys Gln Gln Gln Ser Ala Thr Arg Pro Thr
145                 150                 155                 160

Pro Asp Asn Glu Gln Met Pro Val Asp Thr Thr Gln Asp Arg Leu Leu
                165                 170                 175

Ala Thr Gly Gln Glu Asn Ser Glu Asn Glu Cys Asn Asn Ser Cys Asn
            180                 185                 190

Ala Thr Glu Ala Asn Val Gly Glu Ser Cys Ser Gly Asn Glu Met Asp
        195                 200                 205

Ser Leu Leu Ile Ile Gln Lys Glu Gln His Pro Glu His Glu Glu Gly
    210                 215                 220

Asn Val Val Cys Gln Phe Pro His Gly Ala Arg Arg Ala Ser Gln Gly
225                 230                 235                 240

Thr Pro Ser His His Val Asp Phe Pro Ser Ala Pro Thr Thr Ala Asp
                245                 250                 255

Val Pro Met Glu Glu Gln Pro Lys Asp Leu Ser Arg Glu Asn Ile Ser
            260                 265                 270

Glu Asp Lys Asn Asn Cys Tyr Asn Thr Ser Arg Asn Ala Ala Thr Gln
        275                 280                 285

Val Tyr Ser Gly Asp Asn Ile Pro Arg Asn Lys Ser Asp Ser Leu Phe
    290                 295                 300

Ile Asn Lys Arg Ile Tyr His Pro Glu Pro Glu Val Gly Asp Ile Pro
305                 310                 315                 320

Tyr Gly Val Pro Gln Asp Ser Thr Arg Ala Ser Gln Gly Thr Ser Thr
                325                 330                 335

Cys Leu Gln Glu Ser Leu Gly Glu Cys Phe Ser Glu Asn Asp Pro Arg
            340                 345                 350

Glu Val Pro Gly Leu Gln Ser Arg Gln Glu Gln Pro Ile Ser Asp Pro
        355                 360                 365

Val Leu Leu Gly Lys Asn His Glu Ala Asn Leu Pro Cys Glu Ser His
    370                 375                 380

Gln Lys Arg Phe Cys Arg Asp Ala Lys Leu
385                 390
```

METHODS FOR ENHANCING THE PLURIPOTENCY OF STEM CELLS

CROSS-REFERENCES TO RELATED APPLICATIONS

This application is a divisional application of U.S. Ser. No. 14/006,954, filed Mar. 21, 2012, which is the U.S. National Phase application of PCT/US2012/030005, filed Mar. 21, 2012, which claims priority to US Provisional Application Ser. No. 61/466,667 filed Mar. 23, 2011, the contents of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699442000410SeqList.txt, date recorded: May 7, 2019, size: 100 KB).

FIELD

This disclosure concerns compositions and methods for enhancing or prolonging the pluripotency of a stem cell, and the use of such pluripotent stem cells.

BACKGROUND

Mouse embryonic stem (ES) cells are prototypical pluripotent cells, which are derived from the inner cell mass of blastocysts (Martin, *Proc Natl Acad Sci USA* 78:7634-7638, 1981: Evans and Kaufman, *Nature* 292:154-156, 1981). ES cells have an unusual capacity of proliferating for a long time without losing their genome integrity and karyotype (Suda et al., *J Cell Physiol* 133:197-201, 1987), and are capable of contributing to all the cell types in animals upon injection into mouse blastocysts (Niwa, *Development* 134:635-646, 2007). The most striking evidence of their potency has been demonstrated by injecting ES cells into tetraploid (4N) blastocysts, which produces healthy pups entirely from ES cells (Nagy et al., *Proc Natl Acad Sci USA* 90:8424-8428, 1993). The ultimate test was to see if a single ES cell can form an entire healthy pup, though the success rate was extremely low (0.5%) (Wang and Jaenisch, *Dev Biol* 275:192-201, 2004).

It has recently been shown that Zscan4 (Zinc finger and scan domain-containing protein 4), which is expressed specifically in 2-cell stage embryos and ES cells (Falco et al., *Dev Biol* 307:539-550, 2007), is required for the maintenance of genome stability and normal karyotype in ES cells (Zalzman et al., *Nature* 464:858-863, 2010). Although only a small fraction (~5%) of undifferentiated ES cells express Zscan4 at a given time (Falco et al., *Dev Biol* 307:539-550, 2007), essentially all of the ES cells in culture undergo the transient $Zscan4^+$ state within 9 passages (Zalzman et al., *Nature* 464:858-863, 2010). Upon short hairpin RNA (shRNA)-mediated repression of Zscan4, after about 8 passages ES cells undergo massive karyotype deterioration. Prior studies have also shown that the $Zscan4^+$ state of ES cells is associated with telomere extension (Zalzman et al., *Nature* 464:858-863, 2010). Although ES cells have the best capacity to maintain their genome integrity in culture, it is also widely recognized that even ES cells, in long-term culture, gradually lose their developmental potency (i.e., ability to contribute to tissues in chimeric mice).

SUMMARY

Disclosed herein is the finding that increasing the frequency of Zscan4 activation in mouse ES cells not only enhances, but maintains their developmental potency in long-term cell culture. In particular, disclosed herein is the finding that particular Zscan4 protein truncations and fusion proteins increase the number of $Zscan4^+$ cells and/or promote recurrent activation of Zscan4 in stem cells.

Provided herein are nucleic acid molecules, including vectors, encoding a Zscan4-ERT2 fusion protein. Recombinant Zscan4-ERT2 fusion proteins are also provided. Compositions and cells (such as ES cell or iPS cells) comprising the Zscan4-ERT2 nucleic acid molecules and fusion proteins are also provided herein.

Further provided are nucleic acid molecules, including vectors, encoding a Zscan4 protein with a C-terminal truncation of at least one zinc finger domain, referred herein to as Zscan4-ΔC. Recombinant Zscan4-ΔC proteins are also provided. Compositions and cells (such as ES cell or iPS cells) comprising the Zscan4-ΔC nucleic acid molecules and proteins are also provided herein.

Further provided are methods of enhancing or prolonging the pluripotency of a stem cell or a stem cell population; methods of increasing the frequency of Zscan4 positive cells in a stem cell population; and methods of promoting genome stability or increasing telomere length, or both, in a stem cell or a stem cell population, by increasing the frequency of Zscan4 activation in the stem cell or stem cell population. In some embodiments, the methods include contacting the stem cell or stem cell population with a Zscan4-ERT2 nucleic acid molecule, fusion protein or composition as disclosed herein. In other embodiments, the methods include contacting the stem cell or stem cell population with a Zscan4-ΔC nucleic acid molecule, protein or composition as disclosed herein.

The foregoing and other objects and features of the disclosure will become more apparent from the following detailed description, which proceeds with reference to the accompanying figures.

BRIEF DESCRIPTION OF THE DRAWINGS

FIGS. 1A-1F: Constitutive expression of a Zscan4c-ERT2 fusion protein increases the number of $Zscan4^+$ ES cells. FIG. 1A is a schematic of the structure of a Zscan4c-ERT2 fusion protein. Zscan4c contains one SCAN domain and four C2H2 zinc finger domains. FIG. 1B are fluorescence microscopy images of MC1-ZE3 cells, in which a Zscan4 promoter drives the expression of Emerald marker (left), MC1-ZE3ZERT2 clone #15 cells, in which the Zscan4c-ERT2 fusion protein is constitutively expressed, cultured in the absence of Tmx (middle), and MC1-ZE3-ZERT2 clone #15 cells cultured in the presence of Tmx for 3 days (right). FIG. 1C is a graph showing flow-cytometry analysis of MC1-ZE3 ES cells (left, control) and MC1-ZE3-ZERT2 #15 ES cells (right) in the absence or presence of 1 μM Tmx. Em fluorescence levels (average±S.E.M.; n=6) are shown. Note 3-fold increase of $Em^+$ cells by the constitute expression of a Zscan4c-ERT2 fusion protein even without Tmx. FIG. 1D is a graph showing the results of quantitative RT-PCR analysis of endogenous Zscan4 expression measured by using PCR primer pairs specific for 3'-UTR of Zscan4 in MC1-ZE3 ES cells (left, control) and MC1-ZE3-ZERT2 #15

ES cells (right) in the absence or presence of 1 μM Tmx. The fold-induction of endogenous Zscan4 expression levels (average±S.E.M.; n=6) compared to that of control MC1-ZE3 is shown. Note the 6 fold increase of endogenous Zscan4 at the RNA level by the constitute expression of a Zscan4c-ERT2 fusion protein even without Tmx. FIG. 1E is a series of images of V6.5 parental ES cells (passage number 14). V6.5 ZERT2 #2 (p.20), V6.5 ZERT2 #7 (p.21), V6.5 ZERT2 #10 (p.20), V6.5 ZERT2 #18 (p.22) ES cell colonies after whole-mount RNA in situ hybridization of a Zscan4 full-length probe, which detects both endogenous and exogenous Zscan4 RNAs (upper panel) or a Zscan4 3'-UTR probe, which detects only endogenous Zscan4 RNAs (lower panel). FIG. 1F is a schematic showing comparisons of global expression profiles between V6.5 ZERT2 #18 ES cells and $Em^+$ ES cells (upper panel), and between $Tmx^-$ and $Tmx^+$ conditions of V6.5 ZERT2 #18 ES cells (lower panel). Note that Zscan4-related genes (Zscan4c. BC061212, Tmeme92, and Tcstv1/3) are already upregulated in the V6.5 ZERT2 #18 ES cells even without Tmx.

FIG. 2A is a schematic showing the structure of Zscan4c, Zscan4cERT2, Zscan4c-ΔC and Zscan4c-ΔN proteins. Zscan4c-ΔC was made by deleting four Zinc finger domains at the C-terminus of Zscan4c protein. Zscan4c-ΔN was made by deleting the SCAN domain at the N-terminus. These mutated genes were placed under the strong and constitutive CAG promoter. Each vector was transfected into MC1ZE16 ES cells (sister clones of MC1-ZE3). Multiple independent clones were isolated: ZDC-MC1-ZE16 #3, #4, #20 for Zscan4c-ΔC; ZDN-MC1-ZE16 #5, #8, #15 for Zscan4c-ΔN. FIGS. 2B-2G are fluorescence microscopic images of ZDC-MC1-ZE16 #3 (FIG. 2B), #4 (FIG. 2C), #20 for Zscan4c-ΔC (FIG. 2D) and ZDN-MC1-ZE16 #5 (FIG. 2E), #8 (FIG. 2F), #15 for Zscan4c-ΔN (FIG. 2G). The results demonstrate that the expression of Zscan4c-ΔC increases the number of $Zscan4^+$ cells, whereas the expression of Zscan4c-ΔN does not change the number of $Zscan4^+$ cells.

FIG. 3A shows representative coat colors of chimeric mice generated by injecting various ES cells into blastocysts. The higher chimerism represents the higher contribution of injected ES cells to mice, indicating the higher developmental potency of ES cells. FIG. 3B is a graph showing the percent distribution of chimerism levels among "n" number of mice born from various ES cell lines.

FIGS. 4A-4E: Tetraploid (4N) complementation assays confirm the higher potency of ES cells expressing a Zscan4c-ERT2 fusion protein. FIG. 4A is a table showing development of 4N blastocysts injected with multiple ES cells (10-15 ES cells): V6.5 parental ES cells (passage 18), V6.5 ZERT2 #7 (passage 22), V6.5 ZERT2 #10 (passage 22), V6.5 ZERT2 #18 (passage 19), and freshly isolated TA1 ES cells (passage 3). FIG. 4B is a table showing development of 4N blastocysts injected with single ES cells: V6.5 parental ES cells (passage 18), V6.5 ZERT2 #2 (passage 21), V6.5 ZERT2 #18, and freshly isolated TA1 ES cells (passage 4). FIG. 4C is an image of the embryos examined: only properly developed embryos were counted (the group on the right). FIG. 4D is a pair of images of two live embryos derived from single V6.5 ZERT2 #18 ES cells shown in FIG. 4A. FIG. 4E shows a proposed model of ES cell potency.

FIGS. 5A-5C are a table providing a list of genes upregulated in MC1-ZE7 $Em^+$ cells compared to $Em^-$ cells. FIG. 5A has the first third of the genes. FIG. 5C has the second third of the genes. FIG. 5C has the last third of the genes.

FIG. 6A is a graph showing results of qRT-PCR analysis of Zscan4 expression levels by a primer pair detecting RNA from both endogenous Zscan4 and exogenous Zscan4 (transcripts from a pCGA-Zscan4-ERT2). The primer sequences are 5'-AGTCTGACTGATGAGTGCTTGAAGCC-3' (SEQ ID NO: 15) and 5'-GGCCTTGTTTGCAGATTGCTGTTG-3' (SEQ ID NO: 16). Data were normalized by the expression of H2A, using primers 5'-TrGCAGCTTGCTATACGTGGAGATG-3' (SEQ ID NO: 17) and 5'-TGTTGTCCTTTCTTCCCGATCAGC-3' (SEQ ID NO: 18). The expression levels are shown as a fold change relative to the Zscan4 expression levels of a parental V6.5 ES cells. FIG. 6B is a graph of growth curves of V6.5 ZERT2 #18 ES cells in the presence (Tmx+) or absence of Tamoxifen (Tmx−). The presence of Tmx dramatically reduced the proliferation of ES cells, which was restored by removing the Tmx from the media even after long-term culture with Tmx (Tmx+>−). FIG. 6C is a series of images showing morphologies of cells in each culture condition.

FIG. 8 is a table listing the top 50 genes upregulated in V6.5 ZERT2 #18 ES cells compared to V6.5 #2 ES cells.

FIG. 9 is a table listing the top 50 genes upregulated in V6.5 ZERT2 #18 ES cells cultured in the presence of Tmx for 2 days compared to V6.5 #2 ES cells.

FIGS. 10A-10B: Derivation of new F1 (C57BL/6J×129S6/SvEvTac) hybrid ES cell lines. FIG. 10A is a table showing blastocysts obtained by mating C57BL/6J females with 129S6/SvEvTac males. Blastocysts were cultured in vitro on the mouse embryo fibroblasts (MEFs) feeders in 15% KSR medium (Invitrogen) supplemented with 50 nM PD98059 (MEK1 inhibitor). *Outgrowths showed undifferentiated (U), differentiated (D), and mixed (U/D) cellular phenotypes. FIG. 10B is table providing a summary of ES derivation results.

FIG. 11A is a table of six ES cell lines that showed undifferentiated cellular phenotypes when injected into tetraploid (4N) mouse blastocysts. Success rates of obtaining live embryos at E13.5 varied among ES cell lines, ranging from 15% to 60%. Clone #10 was selected for its highest success rate (named TA1 ES cell line) and was used for subsequent studies. FIG. 11B is a series of representative images of 4N placentas and E13.5 embryos derived from the TA1 ES cell line. Normal appearance of female and male gonads dissected from these embryos indicates their germline competence.

FIG. 12 includes a graph showing that the transient overexpression of Zscan4 was able to increase the developmental potency of ES cells.

SEQUENCE LISTING

Figure 2A:
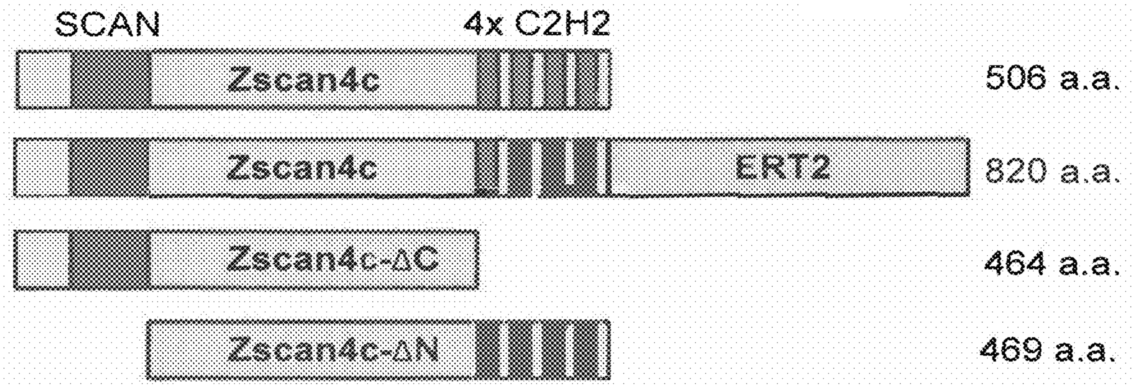
FIGS. 2A-2G: Zscan4 lacking the C-terminus increases the number of $Zscan4^+$ cells.
Figure 2B:
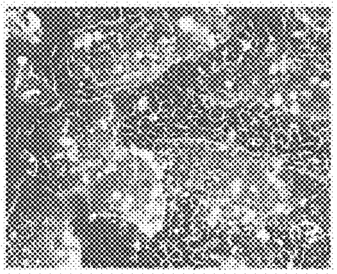
Figure 2C:
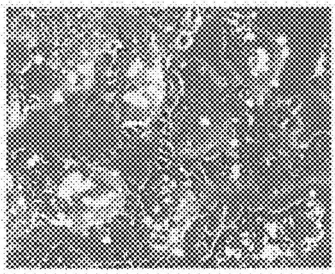
Figure 2D:
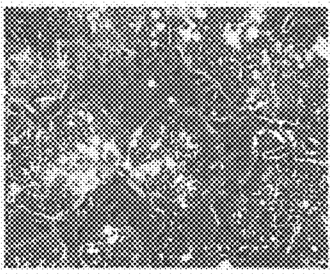
Figure 2E:
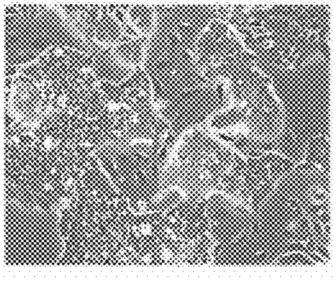
Figure 2F:
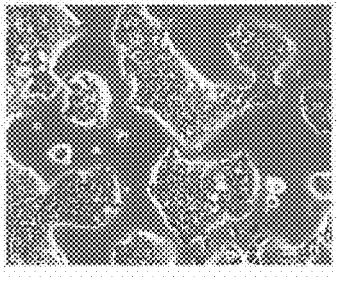
Figure 2G:
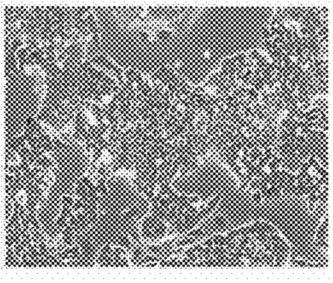

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing: SEQ ID NOs: 1 and 2 are nucleotide and amino acid sequences of human ZSCAN4.

SEQ ID NOs: 3 and 4 are nucleotide and amino acid sequences of mouse Zscan4a.

SEQ ID NOs: 5 and 6 are nucleotide and amino acid sequences of mouse Zscan4b.

SEQ ID NOs: 7 and 8 are nucleotide and amino acid sequences of mouse Zscan4c.

SEQ ID NOs: 9 and 10 are nucleotide and amino acid sequences of mouse Zscan4d.

SEQ ID NOs: 11 and 12 are nucleotide and amino acid sequences of mouse Zscan4e.

SEQ ID NOs: 13 and 14 are nucleotide and amino acid sequences of mouse Zscan4f.

SEQ ID NOs: 15-18 are nucleotide sequences of primers used for qRT-PCR analysis of Zscan4 and H2A.

SEQ ID NO: 19 is the nucleotide acid sequence of plasmid pPyCAGmZscan4c-ERT2.

SEQ ID NO: 20 is the nucleotide sequence of plasmid pPyCAG-hZscan4ERT2.

SEQ ID NO: 21 is the amino acid sequence of human ERT2.

SEQ ID NO: 22 is the amino acid sequence of a mouse Zscan4c-ERT2 fusion protein.

SEQ ID NO: 23 is the amino acid sequence of a human ZSCAN4-ERT2 fusion protein.

SEQ ID NO: 24 is the nucleotide sequence of plasmid pCAG-Zscan4-ΔC.

SEQ ID NO: 25 is the amino acid sequence of mouse Zscan4c-ΔC (lacking all four zinc finger domains).

DETAILED DESCRIPTION

I. Abbreviations a.a. amino acid
cDNA complementary deoxyribonucleic acid
Em Emerald
ES embryonic stem
hCG human chorionic gonadotropin
ICM inner cell mass
LIF leukemia inhibitory factor
MEF murine embryonic fibroblast
ORF open reading frame
PFA paraformaldehyde
qPCR quantitative polymerase chain reaction
qRT-PCR quantitative reverse transcriptase polymerase chain reaction
shRNA short hairpin ribonucleic acid
Tmx tamoxifen

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.). *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of the disclosure, the following explanations of specific terms are provided:

Administration: To provide or give a subject an agent, such as an ES cell or population of ES cells, by any effective route. An exemplary route of administration includes, but is not limited to, injection (such as subcutaneous, intramuscular, intradermal, intraperitoneal, intravenous or intra-arterial).

Agent: Any protein, nucleic acid molecule, compound, cell, small molecule, organic compound, inorganic compound, or other molecule of interest. Contacting: Placement in direct physical association; includes both in solid and liquid form. As used herein, “contacting” is used interchangeably with “exposed.” In some cases. “contacting” includes transfecting, such as transfecting a nucleic acid molecule into a cell.

Degenerate variant: A polynucleotide encoding a polypeptide, such as a Zscan4 polypeptide, that includes a sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged.

Differentiation: Refers to the process by which a cell develops into a specific type of cell (for example, muscle cell, skin cell etc.). Differentiation of embryonic stem cells refers to the development of the cells toward a specific cell lineage. As a cell becomes more differentiated, the cell loses potency, or the ability to become multiple different cell types.

Embryonic stem (ES) cells: Pluripotent cells isolated from the inner cell mass of a developing blastocyst. ES cells can be derived from any organism, such as a mammal. In one embodiment, ES cells are produced from mice, rats, rabbits, guinea pigs, goats, pigs, cows, non-human primates or humans. Human and murine derived ES cells are exemplary. ES cells are pluripotent cells, meaning that they can generate all of the cells present in the body (bone, muscle, brain cells, etc.). Methods for producing murine ES cells can be found, for example, in U.S. Pat. No. 5,670,372. Methods for producing human ES cells can be found, for example, in U.S. Pat. No. 6,090,622, PCT Publication No. WO 00/70021 and PCT Publication No. WO 00/27995. A number of human ES cell lines are known in the art and are publically available. For example, the National Institutes of Health (NIH) Human Embryonic Stem Cell Registry provides a list of a number of human ES cell lines that have been developed (a list can be found online at the NIH Office of Extramural Research website (http://grants.nih.gov/stem_cells/registry/current.htm).

Encapsulated: As used herein, a molecule “encapsulated” in a nanoparticle refers to a molecule (such as Zscan4-ERT2 fusion protein) that is either contained within the nanoparticle or attached to the surface of the nanoparticle, or a combination thereof.

ERT2: A protein comprising a mutated ligand binding domain of the human estrogen receptor that does not bind its natural ligand (17β-estradiol) at physiological concentrations, but is highly sensitive to nanomolar concentrations of tamoxifen or its metabolite 4-hydroxytamoxifen (4OHT) (Feil et al., *Biochem Biophys Res Commun* 237(3):752-757, 1997). An exemplary amino acid sequence for ERT2 is set forth herein as SEQ ID NO: 21, and the corresponding coding sequence is set forth herein as nucleotides 3989-4936 of SEQ ID NO: 19.

ES cell therapy: A treatment that includes administration of ES cells to a subject. In particular examples, the ES cells are Zscan4$^+$ ES cells.

Functional fragment or variant (of Zscan4): The disclosed Zscan4 polynucleotides and polypeptides (such as those set forth as SEQ ID NOs: 1-14) include functional fragments and variants of Zscan4 that retain Zscan4 biological activity. Functional fragments and/or variants of Zscan4 generally comprise at least about 80%, at least about 85%, at least about 90%, at least about 95% or at least about 99% sequence identity with one of the Zscan4 sequences set forth as SEQ ID NOs 1-14. When less than the entire sequence is being compared for sequence identity, fragments will typically possess at least 80% sequence identity over the length of the fragment, and can possess, for example, sequence identities of at least 85%, 90%, 95% or 99%.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons. In some embodiments herein, the fusion protein is a Zscan4-ERT2 fusion protein. In some examples, the fusion protein comprises a linker between the two different proteins.

Genome stability: The ability of a cell to faithfully replicate DNA and maintain integrity of the DNA replication machinery. An ES cell with a stable genome generally defies cellular senescence, can proliferate more than 250 doublings without undergoing crisis or transformation, has a low mutation frequency and a low frequency of chromosomal abnormalities (e.g., relative to embryonal carcinoma cells), and maintains genomic integrity. Long telomeres are thought to provide a buffer against cellular senescence and be generally indicative of genome stability and overall cell health. Chromosome stability (e.g., few mutations, no chromosomal rearrangements or change in number) is also associated with genome stability. A loss of genome stability is associated with cancer, neurological disorders and premature aging. Signs of genome instability include elevated mutation rates, gross chromosomal rearrangements, alterations in chromosome number, and shortening of telomeres.

Heterologous: A heterologous polypeptide or polynucleotide refers to a polypeptide or polynucleotide derived from a different source or species. For example, a mouse Zscan4 peptide expressed in a human ES cell is heterologous to that ES cell.

Host cells: Cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

Induced pluripotent stem (IPS) cells: A type of pluripotent stem cell artificially derived from a non-pluripotent cell, typically an adult somatic cell, by inducing a "forced" expression of certain genes. iPS cells can be derived from any organism, such as a mammal. In one embodiment, iPS cells are produced from mice, rats, rabbits, guinea pigs, goats, pigs, cows, non-human primates or humans. Human and murine derived iPS cells are exemplary.

iPS cells are similar to ES cells in many respects, such as the expression of certain stem cell genes and proteins, chromatin methylation patterns, doubling time, embryoid body formation, teratoma formation, viable chimera formation, and potency and differentiability. Methods for producing iPS cells are known in the art. For example, iPS cells are typically derived by transfection of certain stem cell-associated genes (such as Oct-3/4 (Pouf51) and Sox2) into non-pluripotent cells, such as adult fibroblasts. Transfection can be achieved through viral vectors, such as retroviruses, lentiviruses, or adenoviruses. For example, cells can be transfected with Oct3/4, Sox2, Klf4, and c-Myc using a retroviral system or with OCT4, SOX2, NANOG, and LIN28 using a lentiviral system. After 3-4 weeks, small numbers of transfected cells begin to become morphologically and biochemically similar to pluripotent stem cells, and are typically isolated through morphological selection, doubling time, or through a reporter gene and antibiotic selection. In one example, iPS from adult human cells are generated by the method of Yu et al. (*Science* 318(5854): 1224, 2007) or Takahashi et al. (Cell 131(5):861-72, 2007).

Isolated: An isolated nucleic acid has been substantially separated or purified away from other nucleic acid sequences and from the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. Similarly, "isolated" proteins have been substantially separated or purified from other proteins of the cells of an organism in which the protein naturally occurs, and encompasses proteins prepared by recombination expression in a host cell as well as chemically synthesized proteins. Similarly, "isolated" cells have been substantially separated away from other cell types.

Linker: One or more nucleotides or amino acids that serve as a spacer between two molecules, such as between two nucleic acid molecules or two peptides (such as in a fusion protein). In some examples a linker is 1 to 100 amino acids, such as 1 to 50 or 5 to 10 amino acids.

Nanoparticle: A particle less than about 1000 nanometers (nm) in diameter. Exemplary nanoparticles for use with the methods provided herein are made of biocompatible and biodegradable polymeric materials. In some embodiments, the nanoparticles are PLGA nanoparticles. As used herein, a "polymeric nanoparticle" is a nanoparticle made up of repeating subunits of a particular substance or substances. "Poly(lactic acid) nanoparticles" are nanoparticles having repeated lactic acid subunits. Similarly, "poly(glycolic acid) nanoparticles" are nanoparticles having repeated glycolic acid subunits.

Non-human animal: Includes all animals other than humans. A non-human animal includes, but is not limited to, a non-human primate, a farm animal such as swine, cattle, and poultry, a sport animal or pet such as dogs, cats, horses, hamsters, rodents, such as mice, or a zoo animal such as lions, tigers or bears. In one example, the non-human animal is a transgenic animal, such as a transgenic mouse, cow, sheep, or goat. In one specific, non-limiting example, the transgenic non-human animal is a mouse.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and where necessary to join two protein coding regions, in the same reading frame.

Pharmaceutically acceptable carriers: The pharmaceutically acceptable carriers of use are conventional. *Reming-*

*ton's Pharmaceutical Sciences*, by E. W. Martin, Mack Publishing Co., Easton, Pa., 15th Edition (1975), describes compositions and formulations suitable for pharmaceutical delivery of the Zscan4 proteins (including fusion proteins), Zscan4 nucleic acid molecules, or cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Pluripotent/pluripotency: A "pluripotent" cell is a cell that can form all of an organism's cell lineages (endoderm, mesoderm and ectoderm), including germ cells, but cannot form an entire organisms autonomously. As used herein, enhancing or prolonging pluripotency refers to increasing the pluripotent capacity or duration of pluripotency of a stem cell.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide, such as a Zscan4. Biologically functional fragments, for example, can vary in size from a polypeptide fragment as small as an epitope capable of binding an antibody molecule to a large polypeptide capable of participating in the characteristic induction or programming of phenotypic changes within a cell, including affecting cell proliferation or differentiation. An "epitope" is a region of a polypeptide capable of binding an immunoglobulin generated in response to contact with an antigen. Thus, smaller peptides containing the biological activity of Zscan4, or conservative variants of Zscan4, are thus included as being of use.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, should be minimized in order to preserve the functional and immunologic identity of the encoded protein. Thus, in several non-limiting examples, a Zscan4 polypeptide (or Zscan4 fusion protein, such as Zscan4-ERT2), or other polypeptides disclosed herein, includes at most two, at most five, at most ten, at most twenty, or at most fifty conservative substitutions. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may be, for example, at least 80%, 90% or even 95% or 98% identical to the native amino acid sequence (such as a native Zscan4 sequence or a Zscan4-ERT2 sequence, such as SEQ ID NO: 22 or 23).

Promoter: Nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Recombinant: A recombinant nucleic acid or polypeptide is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988: Higgins & Sharp, *Gene.* 73:237-44, 1988: Higgins & Sharp, *CABIOS* 5:151-3, 1989; Corpet et al., *Nuc. Acids Res.* 16:1088190, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, ES cells, EG cells, GS cells, MAPCs, maGSCs, USSCs, adult stem cells and induced pluripotent stem cells. In one embodiment, stem cells can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation.

Subject: Living multi-cellular vertebrate organisms, a category that includes human and non-human mammals.

Subpopulation: An identifiable portion of a population. As used herein, a "subpopulation" of ES cells expressing Zscan4 is the portion of ES cells in a given population that has been identified as expressing Zscan4.

Telomere: Refers to the end of a eukaryotic chromosome, a specialized structure involved in the replication and stability of the chromosome. Telomeres consist of many repeats of a short DNA sequence in a specific orientation. Telomere functions include protecting the ends of the chromosome so that chromosomes do not end up joined together, and allowing replication of the extreme ends of the chromosomes (by telomerase). The number of repeats of telomeric DNA at the end of a chromosome decreases with age.

Transfecting or transfection: Refers to the process of introducing nucleic acid into a cell or tissue. Transfection can be achieved by any one of a number of methods, such as, but not limited to, liposomal-mediated transfection, electroporation and injection.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). For example, an expression vector contains the necessary regulatory sequences to allow transcription and translation of inserted gene or genes. A vector may also include one or more selectable marker genes and other genetic elements known in the art. Vectors include, for example, virus vectors and plasmid vectors.

Zscan4: A group of genes that have previously identified as exhibiting 2-cellspecific expression and ES cell-specific expression (PCT Publication No. WO 2008/118957) and have been shown to promote telomere elongation and genome stability (Zalzman et al., *Nature* 464(7290):858-863, 2010). In the context of the present disclosure, "Zscan4" includes both human ZSCAN4 and mouse Zscan4. In the mouse, the term "Zscan4" refers to a collection of genes including three pseudogenes (Zscan4-ps1, Zscan4-ps2 and Zscan4-ps3) and six expressed genes (Zscan4a, Zscan4b, Zscan4c, Zscan4d, Zscan4e and Zscan4f). Among the six paralogs, the open reading frames of Zscan4c, Zscan4d, and Zscan4f encode a SCAN domain as well as all four zinc finger domains, suggesting their potential role as transcription factors. Zscan4 refers to Zscan4 polypeptides and Zscan4 polynucleotides encoding the Zscan4 polypeptides. Exemplary sequences are provided herein (see SEQ ID NOs: 1-14).

Zscan4-▤C: In the context of the present disclosure, "Zscan4-ΔC" includes any mouse or human Zscan4 protein having a C-terminal deletion of at least one zinc finger domain. In some embodiments, the Zscan4-ΔC protein includes a deletion of at least two, such as three or all four zinc finger domains. SEQ ID NO: 2 and SEQ ID NO: 8 provide the amino acid sequences of human ZSCAN4 and mouse Zscan4c, respectively, and delineate the N-terminal SCAN domain and C-terminal zinc finger (C2H2-type) domains. In addition, the nucleotide and amino acid regions of each domain of human ZSCAN4 and mouse Zscan4c are listed below.

| Human ZSCAN4 | | |
|---|---|---|
| Domain | Nucleotides (SEQ ID NO: 1) | Amino Acids (SEQ ID NO: 2) |
| SCAN | 826-1074 | 44-126 |
| C2H2-type 1 | 1630-1698 | 312-334 |
| C2H2-type 2 | 1714-1782 | 340-362 |
| C2H2-type 3 | 1798-1866 | 368-390 |
| C2H2-type 4 | 1882-1950 | 396-418 |

| Mouse Zscan4c | | |
|---|---|---|
| Domain | Nucleotides (SEQ ID NO: 7) | Amino Acids (SEQ ID NO: 8) |
| SCAN | 309-557 | 37-119 |
| C2H2-type 1 | 1383-1451 | 395-417 |
| C2H2-type 2 | 1470-1538 | 424-446 |
| C2H2-type 3 | 1554-1622 | 452-474 |
| C2H2-type 4 | 1638-1709 | 480-503 |

Zscan4-ERT2: A fusion protein made up of a Zscan4 amino acid sequence and an ERT2 amino acid sequence. "Zscan4-ERT2" can also refer to a nucleic acid sequence encoding a Zscan4-ERT2 fusion protein. Exemplary amino acid sequences for Zscan4 (including SEQ ID NO: 2, 8, 10 and 14) and ERT2 (SEQ ID NO: 21) are set forth herein. In some embodiments, the Zscan4 sequence is a functional fragment or variant of a known Zscan4 sequence (such as SEQ ID NO: 2, 8, 10 or 14) and/or the ERT2 sequence is a functional fragment or variant of a known ERT2 sequence (such as SEQ ID NO: 21). Any fragment or variant of Zscan4 or ERT2 is contemplated as long as the fragment or variant retains activity. In some examples, the Zscan4-ERT2 fusion protein comprises a linker (or spacer) between Zscan4 and ERT2. Linkers are well known in the art and an appropriate linker can be selected by one of ordinary skill in the art. In particular examples, the linker is encoded by the nucleotide sequence GCTAGC.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

The gold standard for examining the pluripotency of stem cells is to see whether cells can contribute to the entire body of an animal. It is disclosed herein that increasing the frequency of Zscan4 activation in mouse ES cells not only enhances, but also maintains their developmental potency in long-term cell culture. As the potency increases, even a whole animal can be produced from a single ES cell injected into a 4N blastocyst at an unexpectedly high success rate. Although Zscan4-activated cells express genes that are also expressed in 2-cell stage mouse embryos, the transiently Zscan4-activated state of ES cells is not associated with the high potency of ES cells. While not wishing to be bound by theory, these findings indicate that ES cells acquire higher potency by going through the transient Zscan4 activation state more frequently than the regular state. Taken together, these results demonstrate that the frequent activation of Zscan4 can rejuvenate pluripotent stem cells.

Particularly disclosed herein is the finding that the constitutive presence of Zscan4-ERT2, even in the absence of its usual activator tamoxifen, can increase the frequency of endogenous Zscan4 activation in ES cells, resulting in the increase of developmental potency of the ES cells. ES cells cultured in the accelerated Zscan4 activation cycle exhibited improved chimerism and potency, which are evidenced by a high contribution to chimeric mice and efficient production of a whole mouse from a single ES cell. Further disclosed herein is the finding that expression of C-terminally truncated Zscan4 (lacking the zinc finger domains) increases the number of Zscan4$^+$ cells, thus having an effect similar to Zscan4-ERT2.

Accordingly, provided herein are isolated nucleic acid molecules encoding a Zscan4-ERT2 fusion protein. In particular examples, the Zscan4 is mouse Zscan4c or human ZSCAN4. Further provided are vectors comprising a Zscan4-ERT2 coding sequence, cells comprising such vectors (such as ES cells, iPS cells or other stem cells), and compositions that include the Zscan4-ERT2 encoding nucleic acid molecules or vectors. Further provided are recombinant Zscan4-ERT2 fusion proteins, cells comprising Zscan4-ERT2 fusion proteins and compositions that include the Zscan4-ERT2 fusion proteins.

Further provided herein are isolated nucleic acid molecules encoding a Zscan4ΔC protein (a Zscan4 protein having a deletion of at least one zinc finger domain). In particular examples, the Zscan4 is mouse Zscan4c or human ZSCAN4. Further provided are vectors comprising a Zscan4-ΔC coding sequence, cells comprising such vectors (such as ES cells, iPS cells or other stem cells), and compositions that include the Zscan4-ΔC encoding nucleic acid molecules or vectors. Further provided are recombinant Zscan4-ΔC proteins, cells comprising Zscan4-ΔC proteins and compositions that include the Zscan4-ΔC proteins.

Also provided herein are methods of using the Zscan4-ERT2 or Zscan4-ΔC nucleic acid molecules and proteins. For example, methods of enhancing or prolonging the pluripotency of a stem cell or a stem cell population by contacting the stem cell or stem cell population with a Zscan4-ERT2 nucleic acid molecule or fusion protein are disclosed herein. In other examples, methods of enhancing or prolonging the pluripotency of a stem cell or a stem cell population by contacting the stem cell or stem cell population with a Zscan4-ΔC nucleic acid molecule or protein are provided. Similarly, methods of increasing the frequency of Zscan4-positive cells in a stem cell population, as well as methods of promoting genome stability and/or increasing telomere length in a stem cell or a stem cell population, are provided.

A. Compositions, Vectors and Cells Comprising Zscan4-ERT2

Provided herein are isolated nucleic acid molecules encoding a fusion protein, wherein the fusion protein includes a Zscan4 protein fused to an ERT2 protein. ERT2 is a mutated version of the ligand binding domain of human estrogen receptor. ERT2 does not bind its natural ligand (17β-estradiol) at physiological concentrations, but is highly sensitive to nanomolar concentrations of tamoxifen or its metabolite 4-hydroxytamoxifen (4OHT).

In some embodiments, the nucleic acid molecule encoding the Zscan4-ERT2 fusion protein includes human ZSCAN4, mouse Zscan4c, mouse Zscan4d or mouse Zscan4f, or a functional fragment or variant thereof. Functional fragments and variants of Zscan4 include, for example, any Zscan4 fragment or variant that retains one or more biological activities of Zscan4, such as the capacity to increase pluripotency of a stem cell, promote genomic stability or increase telomere length.

Exemplary nucleic acid sequences for a variety of Zscan4 polynucleotides are known in the art (see, for example, PCT Publication No. WO 2008/118957) and are set forth herein, such as SEQ ID NO: 1 (human ZSCAN4), SEQ ID NO: 7 (mouse Zscan4c), SEQ ID NO: 9 (mouse Zscan4d) and SEQ ID NO: 13 (mouse Zscan4f). One skilled in the art will appreciate that sequences having at least 80%, at least 85%, at least 90%, at least 95%, at least 96%, at least 97%, at least 98% or at least 99% sequence identity to these sequences and retain Zscan4 activity are contemplated and can be used in the compositions and methods provided herein.

Zscan4 nucleic acid sequences from other species are also publically available, including dog ZSCAN4 (GenBank Accession Nos. XM_541370 and XM_848557); cow ZSCAN4 (GenBank Accession No. XM_001789250); and horse ZSCAN4 (GenBank Accession No. XM_001493944). Each of the above-listed GenBank Accession numbers is herein incorporated by references as it appears in the GenBank database on Feb. 22, 2011.

Fragments and variants of Zscan4 polynucleotides can readily be prepared by one of skill in the art using molecular techniques. In one embodiment, a fragment of a Zscan4 nucleic acid sequences includes at least 250, at least 500, at least 750, at least 1000, at least 1500, or at least 2000 consecutive nucleic acids of the Zscan4 polynucleotide. In a further embodiment, a fragment of Zscan4 is a fragment that confers a function of Zscan4 when expressed in a cell of interest, such as, but not limited to, promoting pluripotency, enhancing genome stability and/or increasing telomere length. The Zscan4 nucleic acid sequences contemplated herein include sequences that are degenerate as a result of the genetic code. There are 20 natural amino acids, most of which are specified by more than one codon. Therefore, all degenerate nucleotide sequences are included as long as the amino acid sequence of the Zscan4 polypeptide encoded by the nucleotide sequence is functionally unchanged.

In some embodiments, the Zscan4 nucleic acid sequence portion of the nucleic acid molecule encoding the Zscan4-ERT2 fusion protein is at least 80%, at least 85%, at least 90%, at least 95%, at least 96%, at least 97%, at least 98% or at least 99% identical to SEQ ID NO: 1, 7, 9 or 13. In some embodiments, the Zscan4 nucleic acid sequence comprises the nucleic acid sequence set forth in SEQ ID NO: 1, 7, 9 or 13. In some embodiments, the Zscan4 nucleic acid sequence consists of the nucleic acid sequence set forth in SEQ ID NO: 1, 7, 9 or 13.

In some examples, the Zscan4 portion of the Zscan4-ERT2 fusion protein comprises mouse Zscan4c. Thus, in particular examples, the Zscan4 nucleic acid sequence is at least 80%, at least 85%, at least 90%, at least 95%, at least 96%, at least 97%, at least 98% or at least 99% identical to SEQ ID NO: 7. In other examples, the Zscan4 comprises human ZSCAN4. In particular examples, the Zscan4 nucleic acid sequence is at least 80%, at least 85%, at least 90%, at least 95%, at least 96%, at least 97%, at least 98% or at least 99% identical to SEQ ID NO: 1.

In some embodiments, the nucleic acid sequence encoding the ERT2 portion of the Zscan4-ERT2 fusion protein is at least 80%, at least 85%, at least 90%, at least 95%, at least 96%, at least 97%, at least 98% or at least 99% identical to nucleotides 3989-4936 of SEQ ID NO: 19. In some examples, the nucleic acid sequence encoding ERT2 comprises or consists of nucleotides 3989-4936 of SEQ ID NO: 19.

In some embodiments, the nucleic acid molecule encoding the Zscan4-ERT2 fusion protein includes a linker sequence between the Zscan4 and ERT2 coding sequences. Linkers are well known in the art and selection of an appropriate linker is well within the capabilities of one of ordinary skill in the art. In some examples, the linker is at least 2 amino acids (aa), at least 3, at least 5, at least 10, at least 20, at least 50 or at least 100 aa, such as 2 to 50 or 2 to 10 aa. In particular examples disclosed herein, the linker includes the nucleic acid sequence GCTAGC (nucleotides 3983-3988 of SEQ ID NO: 19).

In some embodiments in which the Zscan4-ERT2 nucleic acid molecule encodes mouse Zscan4c, the nucleic acid molecule comprises a sequence at least 80%, at least 85%, at least 90%, at least 95%, at least 96%, at least 97%, at least 98% or at least 99% identical to nucleotides 2465-4936 of SEQ ID NO: 19. In particular examples, the nucleic acid molecule comprises, or consists of, the sequence of nucleotides 2465-4936 of SEQ ID NO: 19.

In other embodiments in which the Zscan4-ERT2 nucleic acid molecule encodes human ZSCAN4, the nucleic acid molecule comprises a sequence at least 80%, at least 85%, at least 90%, at least 95%, at least 96%, at least 97%, at least 98% or at least 99% identical to nucleotides 2479-4731 of SEQ ID NO: 20. In particular examples, the nucleic acid molecule comprises, or consists of, the sequence of nucleotides 2479-4731 of SEQ ID NO: 20. Also provided are vectors that include a Zscan4-ERT2 encoding nucleic acid molecule disclosed herein. Any suitable expression vector, such as an expression (plasmid) vector (e.g., pPyCAG-BstXI-IP), or viral vector (e.g., an adenovirus, adenoassociated virus, lentivirus or retrovirus vector), is contemplated. Numerous expression vectors and viral vectors are known in the art and the selection of an appropriate vector is well within the capabilities of one of ordinary skill in the art.

In some embodiments, the vector comprises a nucleotide sequence that is at least 80%, at least 85%, at least 90%, at least 95%, at least 96%, at least 97%, at least 98% or at least 99% identical to SEQ ID NO: 19 or SEQ ID NO: 20. In some examples, the vector comprises a nucleic acid sequence that is at least 95% identical to SEQ ID NO: 19 or SEQ ID NO: 20. In specific non-limiting embodiments, the nucleic acid sequence of the vector comprises, or consists of, SEQ ID NO: 19 or SEQ ID NO: 20.

Further provided herein are isolated cells containing a Zscan4-ERT2 nucleic acid molecule or vector as described herein. In some embodiments, the cell is a stem cell. In particular examples, the stem cell is an ES cell or an iPS cell. The origin of the stem cell can be from any suitable species. In some examples, the stem cell is a mouse, rat, human or non-human primate stem cell.

Compositions comprising a nucleic acid molecule or vector encoding a Zscan4ERT2 fusion protein are also provided herein. The compositions may further include a carrier or diluent, such as a pharmaceutically acceptable carrier or diluent. Zscan4-ERT2 fusion proteins encoded by the nucleic acid molecules and vectors described herein are further provided.

Also provided herein are recombinant Zscan4-ERT2 fusion proteins. In some embodiments, the recombinant Zscan4-ERT2 fusion protein includes human ZSCAN4, mouse Zscan4c, mouse Zscan4d or mouse Zscan4f, or a functional fragment or variant thereof. Functional fragments and variants of Zscan4 include, for example, any Zscan4 fragment or variant that retains one or more biological activities of Zscan4, such as the capacity to increase pluripotency of a stem cell, promote genomic stability or increase telomere length.

Exemplary amino acid sequences for a variety of Zscan4 proteins are known in the art (see, for example, PCT Publication No. WO 2008/118957) and are set forth herein, such as SEQ ID NO: 2 (human ZSCAN4), SEQ ID NO: 8 (mouse Zscan4c), SEQ ID NO: 10 (mouse Zscan4d) and SEQ ID NO: 14 (mouse Zscan4f). One skilled in the art will appreciate that sequences having at least 80%, at least 85%, at least 90%, at least 95%, at least 96%, at least 97%, at least 98% or at least 99% sequence identity to these sequences and retain Zscan4 activity are contemplated and can be used in the methods provided herein.

Zscan4 amino acid sequences from other species are publically available, including dog ZSCAN4 (GenBank Accession Nos. XP_541370 and XP_853650); cow ZSCAN4 (GenBank Accession No. XP_001789302); and horse ZSCAN4 (GenBank Accession No. XP_001493994). Each of the above-listed GenBank Accession numbers is herein incorporated by references as it appears in the GenBank database on Feb. 22, 2011.

Fragments and variants of a Zscan4 protein can readily be prepared by one of skill in the art using molecular techniques. In one embodiment, a fragment of a Zscan4 protein includes at least 50, at least 100, at least 150, at least 200, at least 250, at least 300, at least 350, at least 400, at least 450 or at least 500 consecutive amino acids of the Zscan4 polypeptide. In a further embodiment, a fragment of Zscan4 is a fragment that confers a function of Zscan4, such as, but not limited to, increasing pluripotency, enhancing genome stability or increasing telomere length.

In some embodiments, the Zscan4 protein portion of the Zscan4-ERT2 fusion protein includes an amino acid sequence at least 80%, at least 85%, at least 90%, at least 95%, at least 96%, at least 97%, at least 98% or at least 99% identical to the amino acid sequence set forth in SEQ ID NO: 2, 8, 10 or 14. In a further embodiment, the Zscan4 protein is a conservative variant of SEQ ID NO: 2, 8, 10 or 14, such that it includes no more than fifty conservative amino acid substitutions, such as no more than two, no more than five, no more than ten, no more than twenty, or no more than fifty conservative amino acid substitutions in SEQ ID NO: 2, 8, 10 or 14. In another embodiment, the Zscan4 peptide portion of the Zscan4-ERT2 fusion protein has an amino acid sequence comprising or consisting of the amino acid sequence set forth in SEQ ID NO: 2, 8, 10 or 14.

In some embodiments of the Zscan4-ERT2 fusion proteins, the Zscan4 comprises mouse Zscan4c. In some examples, the Zscan4c amino acid sequence is at least 80%, at least 85%, at least 90%, at least 95%, at least 96%, at least 97%, at least 98% or at least 99% identical to the amino acid sequence of SEQ ID NO: 8.

In other embodiments of the Zscan4-ERT2 fusion proteins, the Zscan4 portion comprises human ZSCAN4. In some examples, the ZSCAN4 amino acid sequence is at least 80%, at least 85%, at least 90%, at least 95%, at least 96%, at least 97%, at least 98% or at least 99% identical to the amino acid sequence of SEQ ID NO: 2.

In some embodiments, the amino acid sequence of the ERT2 portion of the Zscan4-ERT2 fusion protein is at least 80%, at least 85%, at least 90%, at least 95%, at least 96%, at least 97%, at least 98% or at least 99% identical to SEQ ID NO: 21. In some examples, the amino acid sequence of ERT2 comprises or consists of SEQ ID NO: 21.

In some embodiments, the Zscan4-ERT2 fusion protein includes a linker between the Zscan4 and ERT2 sequences. Linkers are well known in the art and selection of an appropriate linker is well within the capabilities of one of ordinary skill in the art. In particular examples disclosed herein, the linker includes the amino acid sequence Ala-Ser.

In some embodiments in which the Zscan4-ERT2 fusion protein includes mouse Zscan4c, the amino acid sequence of the fusion protein is at least 80%, at least 85%, at least 90%, at least 95%, at least 96%, at least 97%, at least 98% or at least 99% identical to SEQ ID NO: 22. In particular examples, the amino acid sequence of the Zscan4ERT2 fusion protein comprises, or consists of, the amino acid sequence of SEQ ID NO: 22.

In other embodiments in which the Zscan4-ERT2 fusion protein includes human ZSCAN4, the amino acid sequence of the fusion protein is at least 80%, at least 85%, at least 90%, at least 95%, at least 96%, at least 97%, at least 98% or at least 99% identical to SEQ ID NO: 23. In particular examples, the amino acid sequence of the Zscan4-ERT2 fusion protein comprises, or consists of, the amino acid sequence of SEQ ID NO: 23.

Further provided herein are isolated cells comprising a Zscan4-ERT2 fusion protein disclosed herein. In some embodiments, the cells are stem cells. In particular examples, the stem cells are ES cells or iPS cells. The origin of the stem cell can be from any suitable species. In some examples, the stem cell is a mouse, rat, human or non-human primate stem cell.

Compositions comprising a Zscan4-ERT2 fusion protein are also provided herein. The compositions may further include a carrier or diluent, such as a pharmaceutically acceptable carrier or diluent, for example saline.

B. Compositions, Vectors and Cells Comprising Zscan4-ΔC

Also provided herein are isolated nucleic acid molecules encoding a Zscan4 protein with a C-terminal truncation (referred to herein as Zscan4-ΔC). The C-terminally truncated Zscan4 comprises a deletion of at least one zinc finger domain. Thus, in some embodiments, the Zscan4-ΔC protein has a deletion of one, two, three or four zinc finger domains.

In some embodiments, the nucleic acid molecule encoding the Zscan4-ΔC protein includes C-terminally truncated human ZSCAN4, mouse Zscan4c, mouse Zscan4d or mouse Zscan4f. In particular embodiments, the Zscan4-ΔC protein is either human ZSCAN4 or mouse Zscan4c with a deletion of all four zinc finger domains. In one non-limiting example, the Zscan4-ΔC protein comprises the amino acid sequence of SEQ ID NO: 25 and/or is encoded by nucleotides 2465-3649 of SEQ ID NO: 24.

The Zscan4-ΔC nucleic acid sequences contemplated herein include sequences that are degenerate as a result of the genetic code. There are 20 natural amino acids, most of which are specified by more than one codon. Therefore, all degenerate nucleotide sequences are included as long as the amino acid sequence of the Zscan4-ΔC polypeptide encoded by the nucleotide sequence is functionally unchanged.

In some embodiments, the Zscan4-ΔC nucleic acid sequence is at least 80%, at least 85%, at least 90%, at least 95%, at least 96%, at least 97%, at least 98% or at least 99% identical to nucleotides 2465-3649 of SEQ ID NO: 24. In some embodiments, the Zscan4-ΔC nucleic acid sequence comprises the nucleic acid sequence set forth as nucleotides 2465-3649 of SEQ ID NO: 24. In some embodiments, the Zscan4-ΔC nucleic acid sequence consists of the nucleic acid sequence set forth as nucleotides 2465-3649 of SEQ ID NO: 24.

In some embodiments, the Zscan4-ΔC nucleic acid molecule is a human Zscan4-ΔC nucleic acid molecule. In particular examples, the human Zscan4-ΔC nucleic acid molecule comprises a deletion of at least nucleotides 1630-1950, nucleotides 1714-1950, nucleotides 1798-1950 or nucleotides 1882-1950 of SEQ ID NO: 1. In some embodiments, the human Zscan4-ΔC nucleic acid molecule is at least 80%, at least 85%, at least 90%, at least 95%, at least 96%, at least 97%, at least 98% or at least 99% identical to nucleotides 1-1629, nucleotides 1-1713, nucleotides 1-1797 or nucleotides 1-1881 of SEQ ID NO: 1. In some examples, the human Zscan4-ΔC nucleic acid molecule comprises or consists of nucleotides 1-1629, nucleotides 1-1713, nucleotides 1-1797 or nucleotides 1-1881 of SEQ ID NO: 1.

In some embodiments, the Zscan4-ΔC nucleic acid molecule is a mouse Zscan4ΔC nucleic acid molecule. In particular examples, the mouse Zscan4-ΔC nucleic acid molecule comprises a deletion of at least nucleotides 1383-1709, nucleotides 1470-1709, nucleotides 1554-1709 or nucleotides 1638-1709 of SEQ ID NO: 7. In some embodiments, the mouse Zscan4-ΔC nucleic acid molecule is at least 80%, at least 85%, at least 90%, at least 95%, at least 96%, at least 97%, at least 98% or at least 99% identical to nucleotides 1-1382, nucleotides 1-1469, nucleotides 1-1553 or nucleotides 1-1637 of SEQ ID NO: 7. In some examples, the mouse Zscan4-ΔC protein comprises or consists of nucleotides 1-1382, nucleotides 1-1469, nucleotides 1-1553 or nucleotides 1-1637 of SEQ ID NO: 7.

Also provided are vectors that include a Zscan4-ΔC encoding nucleic acid molecule disclosed herein. Any suitable expression vector, such as an expression (plasmid) vector (e.g., pPyCAG-BstXI-IP), or viral vector (e.g., an adenovirus, adeno-associated virus, lentivirus or retrovirus vector), is contemplated. Numerous expression vectors and viral vectors are known in the art and the selection of an appropriate vector is well within the capabilities of one of ordinary skill in the art.

In some embodiments, the vector comprises a nucleotide sequence that is at least 80%, at least 85%, at least 90%, at least 95%, at least 96%, at least 97%, at least 98% or at least 99% identical to SEQ ID NO: 24. In some examples, the vector comprises a nucleic acid sequence that is at least 95% identical to SEQ ID NO: 24. In specific non-limiting embodiments, the nucleic acid sequence of the vector comprises, or consists of, SEQ ID NO: 24.

Further provided herein are isolated cells containing a Zscan4-ΔC nucleic acid molecule or vector as described herein. In some embodiments, the cell is a stem cell. In particular examples, the stem cell is an ES cell or an iPS cell. The origin of the stem cell can be from any suitable species. In some examples, the stem cell is a mouse, rat, human or non-human primate stem cell.

Compositions comprising a nucleic acid molecule or vector encoding a Zscan4ΔC protein are also provided herein. The compositions may further include a carrier or diluent, such as a pharmaceutically acceptable carrier or diluent.

Zscan4-ΔC proteins encoded by the nucleic acid molecules and vectors described herein are further provided.

Also provided herein are recombinant Zscan4-ΔC proteins. In some embodiments, the recombinant Zscan4-ΔC protein includes C-terminally truncated human ZSCAN4, mouse Zscan4c, mouse Zscan4d or mouse Zscan4f.

In some embodiments, the Zscan4-ΔC protein includes an amino acid sequence at least 80%, at least 85%, at least 90%, at least 95%, at least 96%, at least 97%, at least 98% or at least 99% identical to the amino acid sequence set forth in SEQ ID NO: 25. In a further embodiment, the Zscan4-ΔC protein is a conservative variant of SEQ ID NO: 25, such that it includes no more than fifty conservative amino acid substitutions, such as no more than two, no more than five, no more than ten, no more than twenty, or no more than fifty conservative amino acid substitutions in SEQ ID NO: 25. In another embodiment, the Zscan4-ΔC protein has an amino acid sequence comprising or consisting of the amino acid sequence set forth in SEQ ID NO: 25.

In some embodiments, the Zscan4-ΔC protein is a human Zscan4-ΔC protein. In particular examples, the human Zscan4-ΔC protein comprises a deletion of at least amino acids 312-418, amino acids 340-418, amino acids 368-390 or amino acids 396418 of SEQ ID NO: 2. In some embodiments, the human Zscan4-ΔC protein is at least 80%, at least 85%, at least 90%, at least 95%, at least 96%, at least 97%, at least 98% or at least 99% identical to amino acids 1-311, amino acids 1-339, amino acids 1-367 or amino acids 1-395 of SEQ ID NO: 2. In some examples, the human Zscan4-ΔC protein comprises or consists of amino acids 1-311, amino acids 1-339, amino acids 1-367 or amino acids 1-395 of SEQ ID NO: 2.

In some embodiments, the Zscan4-ΔC protein is a mouse Zscan4-ΔC protein. In particular examples, the mouse Zscan4-ΔC protein comprises a deletion of at least amino acids 395-503, amino acids 424-503, amino acids 452-503 or amino acids 480-503 of SEQ ID NO: 8.

In some embodiments, the mouse Zscan4-ΔC protein is at least 80%, at least 85%, at least 90%, at least 95%, at least 96%, at least 97%, at least 98% or at least 99% identical to amino acids 1-394, amino acids 1-423, amino acids 1-451 or amino acids 1-479 of SEQ ID NO: 8. In some examples, the mouse Zscan4-ΔC protein comprises or consists of amino acids 1-394, amino acids 1-423, amino acids 1-451 or amino acids 1-479 of SEQ ID NO: 8.

Further provided herein are isolated cells comprising a Zscan4-ΔC protein disclosed herein. In some embodiments, the cells are stem cells. In particular examples, the stem cells are ES cells or iPS cells. The origin of the stem cell can be from any suitable species. In some examples, the stem cell is a mouse, rat, human or non-human primate stem cell.

Compositions comprising a Zscan4-ΔC protein are also provided herein. The compositions may further include a carrier or diluent, such as a pharmaceutically acceptable carrier or diluent, for example saline.

C. Recurrent Activation of Zscan4 in Stem Cells and Methods of Use

Disclosed herein is the finding that recurrent activation of Zscan4 enhances the pluripotency of stem cells. In particular, it is disclosed herein that increasing the frequency of Zscan4 activation in ES cells enhances and maintains developmental potency in long-term culture. The results described in the Examples below indicate that ES cells acquire higher potency by going through the transient Zscan4 activation state more frequently than the regular state.

Thus, provided herein are methods of enhancing or prolonging the pluripotency of a stem cell or a stem cell population by inducing frequent activation of Zscan4 in the stem cell or stem cell population. Methods of increasing the frequency of Zscan4-positive cells in a stem cell population by inducing frequent activation of Zscan4 are also provided. Further provided are methods of promoting genome stability or increasing telomere length, or both, in a stem cell or a stem cell population by promoting recurrent activation of Zscan4 in the stem cell or stem cell population.

In some embodiments of the methods disclosed herein, the methods include contacting the stem cell or stem cell population with (i) a nucleic acid molecule encoding a Zscan4-ERT2 fusion protein or a composition thereof, (ii) a vector encoding a Zscan4-ERT2 fusion protein or a composition thereof, or (iii) a Zscan4-ERT2 fusion protein or a composition thereof.

In other embodiments of the methods disclosed herein, the methods include contacting the stem cell or stem cell population with (i) a nucleic acid molecule encoding a Zscan4-ΔC protein or a composition thereof, (ii) a vector encoding a Zscan4-ΔC protein or a composition thereof, or (iii) a Zscan4-ΔC protein or a composition thereof.

In other embodiments, a stem cell or stem cell population is contacted with an agent that promotes frequent activation of Zscan4. The agent can be, for example, any nucleic acid molecule, polypeptide, small molecule or other compound that results in recurrent activation of Zscan4 in a cell.

In some examples, the stem cell is an ES cell or an iPS. The methods can be applied to stem cells of any species, for example, mouse, rat, human or non-human primate stem cells.

1. Enhancing or Prolonging Pluripotency of Stem Cells

Provided herein is a method of enhancing or prolonging the pluripotency of a stem cell or a stem cell population. In some embodiments, the method includes contacting the stem cell or stem cell population with a nucleic acid molecule or vector encoding a Zscan4-ERT2 fusion protein as disclosed herein. In other embodiments, the method includes contacting the stem cell or stem cell population with a Zscan4-ERT fusion protein disclosed herein.

In yet other embodiments, the method includes contacting the stem cell or stem cell population with a nucleic acid molecule or vector encoding a Zscan4-ΔC protein as disclosed herein. In other embodiments, the method includes contacting the stem cell or stem cell population with a Zscan4-ΔC protein disclosed herein.

Methods of delivering a nucleic acid molecule into a cell are well known in the art. In some examples, "contacting" the stem cell with a nucleic acid molecule or vector includes transfection (such as liposomal-mediated transfection), electroporation, injection or any other suitable technique for introducing a nucleic acid molecule into a cell.

Methods for delivery of proteins to cells are also well known in the art. In some examples, the Zscan4-ERT2 fusion protein or Zscan4-ΔC protein is encapsulated by a nanoparticle to aid in delivery to the cells. Suitable nanoparticles for use with the disclosed methods are known in the art and are described briefly below.

The nanoparticles for use with the methods described herein can be any type of biocompatible nanoparticle, such as biodegradable nanoparticles, such as polymeric nanoparticles, including, but not limited to polyamide, polycarbonate, polyalkene, polyvinyl ethers, and cellulose ether nanoparticles. In some embodiments, the nanoparticles are made of biocompatible and biodegradable materials. In some embodiments, the nanoparticles include, but are not limited to nanoparticles comprising poly(lactic acid) or poly(glycolic acid), or both poly(lactic acid) and poly(glycolic acid). In particular embodiments, the nanoparticles are poly(D,L-lactic-co-glycolic acid) (PLGA) nanoparticles.

Other biodegradable polymeric materials are contemplated for use with the methods described herein, such as poly(lactic acid) (PLA) and polyglycolide (PGA). Additional useful nanoparticles include biodegradable poly(alkylcyanoacrylate) nanoparticles (Vauthier et al., *Adv. Drug Del. Rev.* 55: 519-48, 2003).

Various types of biodegradable and biocompatible nanoparticles, methods of making such nanoparticles, including PLGA nanoparticles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139, U.S. Pat. Nos. 5,753,234; 7,081,489; and PCT Publication No. WO/2006/052285).

Methods of assessing the pluripotency of a cell am known in the art. Example 2 below describes exemplary methods that can be used to evaluate the potency of an ES cell. In one example, ES cells are injected into mouse blastocysts, transferred to uteri and the extent of ES cell potency is determined by the percent chimerism of the pups based on coat color. In another example, a 4N complementation assay is performed. In this assay, ES cells are injected into a tetraploid (4N) blastocyst. Potency of the ES cells is determined by the ability of the ES cells to produce live embryos.

In some examples, the pluripotency of a stem cell or a stem cell population is increased by at least 10%, at least 20%, at least 30%, at least 40%, at least 50%, at least 60%, at least 70%, at least 80%, at least 90% or at least 100%, as compared to the pluripotency of a stem cell or a stem cell population in the absence of increased Zscan4 activation frequency (such as in the absence of expression of an Zscan4-ERT2 fusion protein).

Also provided herein is a method for increasing the developmental potency of a stem cell or a stem cell population by transiently overexpressing Zscan4. In one embodiment, the overexpressed Zscan4 is mouse Zscan4c.

Further provided herein is a method of enhancing or prolonging the pluripotency of a stem cell or a stem cell population, by contacting the stem cell or stem cell population with an isolated nucleic acid molecule encoding a Zscan4 protein or a vector that includes a nucleic acid molecule encoding a Zscan 4 protein. In an embodiment employing a vector, the vector includes an inducible promoter.

2. Increasing the Frequency of $Zscan4^+$ Cells in a Population

Also provided herein is a method of increasing the frequency of Zscan4-positive cells in a stem cell population. In some embodiments, the method includes contacting the stem cell population with a nucleic acid molecule or vector encoding a Zscan4-ERT2 fusion protein disclosed herein.

In other embodiments, the method includes contacting the stem cell population with a Zscan4-ERT fusion protein disclosed herein. In yet other embodiments, the method includes contacting the stem cell population with a nucleic acid molecule or vector encoding a Zscan4-ΔC protein disclosed herein. In other embodiments, the method includes contacting the stem cell population with a Zscan4-ΔC protein disclosed herein.

Methods of delivering nucleic acid molecules encoding Zscan4-ERT2 or Zscan4-ΔC, and Zscan4-ERT2 or Zscan4-ΔC proteins to stem cells are known in the art and are described above.

Methods of detecting $Zscan4^+$ cells in a cell population are routine and have been previously described (see for example, PCT Publication No. WO 2008/118957, herein incorporated by reference). For example, antibodies specific for Zscan4 (which are commercially available or can be produced according to standard procedures) can be used in immunological based assays to detect $Zscan4^+$ cells. For instance, fluorescence-activated cell sorting can be used to detect and quantify $Zscan4^+$ cells in a population. As another example, a Zscan4 reporter construct can be used to detect expression of Zscan4 (such as the pZscan4-Emerald vector as described in PCT Publication No. WO 2008/118957).

In particular examples, the increase in frequency of $Zscan4^+$ cells in the population is an increase of at least 5%, at least 10%, at least 15%, at least 20%, at least 25%, at least 30%, at least 40%, at least 50%, at least 50%, at least 75%, at least 90% or at least 100%. The increase is relative to, for example, a population of cells that has not been contacted with a Zscan4-ERT2 nucleic acid or fusion protein, or a Zscan4-ΔC nucleic acid or protein (and thus has not undergone frequent activation of Zscan4).

3. Promoting Genome Stability and Increasing Telomere Length

Methods of promoting genome stability or increasing telomere length, or both, in a stem cell or a stem cell population are further provided. In some embodiments, the method includes contacting the stem cell or stem cell population with a nucleic acid molecule or vector encoding a Zscan4-ERT2 fusion protein disclosed herein. In other embodiments, the method includes contacting the stem cell or stem cell population with a Zscan4-ERT fusion protein disclosed herein.

In yet other embodiments, the method includes contacting the stem cell or stem cell population with a nucleic acid molecule or vector encoding a Zscan4-ΔC protein disclosed herein. In other embodiments, the method includes contacting the stem cell or stem cell population with a Zscan4-ΔC protein disclosed herein.

Methods of delivering nucleic acid molecules encoding Zscan4-ERT2 or Zscan4-ΔC, and Zscan4-ERT2 or Zscan4-ΔC proteins to stem cells are known in the art and are described above.

In particular examples, genome stability is increased in a stem cell by at least 20%, at least 40%, at least 50%, at least 60%, at least 75%, at least 80%, at least 90%, at least 95%, or at least 98%, for example relative to stem cell that has not been contacted with a Zscan4-ERT2 or Zscan4-ΔC protein or a nucleic acid encoding a Zscan4-ERT2 or Zscan4-ΔC protein (or compared to a value or range of values expected in a stem cell that has not undergone frequent activation of Zscan4). Methods of measuring genome stability and telomere length are routine in the art, and the disclosure is not limited to particular methods. The particular examples provided herein are exemplary.

In some examples, genome stability in a stem cell is measured by detecting cell proliferation. Genome stability is increased if cell proliferation is increased, for example relative to a control cell (for example, a stem cell that has not been contacted with a Zscan4-ERT or Zscan4-ΔC protein or nucleic acid). For example, ES cell proliferation can be detected by growing ES cells in culture and measuring the doubling time of the cells after each passage. In one example, genome stability is increased if crisis (e.g., cell death) does not occur at passage 8 or earlier.

In some examples, genome stability in a stem cell, such as an ES cell or iPS cells, is measured by performing karyotype analysis. Genome stability is increased if the presence of karyotype abnormalities (such as chromosome fusions and fragmentations) is decreased or even absent, for example relative to a cell that has not undergone frequent activation of Zscan4. For example, karyotype analysis can be performed in stem cells by inducing metaphase arrests, then preparing metaphase chromosome spreads.

In some examples, genome stability in stem cell is measured by measuring telomere sister chromatid exchange (T-SCE). Genome stability is increased if the presence of T-SCE is increased relative to a control (such as a stem cell that has not undergone frequent activation of Zscan4). For example, T-SCE can be measured in an stem cell by using telomere chromosome-orientation FISH (CO-FISH).

In some examples, genome stability in stem cell is measured by measuring sister chromatid exchange (SCE). Genome stability is increased if the presence of SCE is decreased relative to a control, such as a stem cell that has not undergone frequent activation of Zscan4. For example, SCE can be measured in a stem cell by detecting SCE in a metaphase spread.

In some examples, telomere length is measured in stem cell. Telomere length is increased in a stem cell if the length of the telomeres is greater, for example relative to telomere length in a control cell that has not undergone frequent activation of Zscan4 (such as a cell that has not been contacted with a Zscan4-ERT2 or Zscan4-ΔC protein or nucleic acid). For example, telomere length can be detected in a stem cell by fluorescence in situ hybridization (FISH), quantitative FISH (Q-FISH), or telomere qPCR.

The following examples are provided to illustrate certain particular features and/or embodiments. These examples should not be construed to limit the disclosure to the particular features or embodiments described.

EXAMPLES

Example 1: Materials and Methods

This example describes the experimental procedures used for the studies described in Example 2.

ES Cell Culture

MC1 ES cells derived from 129S6/SvEvTac and MC2 ES cells derived from C57BL/6J (Olson et al., *Cancer Res* 63:6602-6606, 2003) were purchased from the Transgenic Core Laboratory of the Johns Hopkins University School of Medicine (Baltimore, Md.). V6.5 ES cells (Eggan et al., *Proc Nat Acad Sci USA* 98:6209-6214, 2001) derived from an F1 hybrid strain (C57BL/6×129/Sv) were purchased from Thermo Scientific Open Biosystem. All ES cell lines, except for TA1 ES cell line (see below), were cultured at 37° C. in 5% $CO^2$ in the complete ES medium as previously described (Zalzman et al., *Nature* 464:858-863, 2010): DMEM (Gibco), 15% FBS (Atlanta Biologicals), 1000 U/ml leukemia inhibitory factor (LIF) (ESGRO, Chemicon), 1 mM sodium pyruvate, 0.1 mM non-essential amino acids (NEAA), 2 mM GlutaMAX™, 0.1 mM beta-mercaptoethanol, and penicillin/streptomycin (50 U/50 μg/ml). TA1 ES cell lines were cultured as described above. For all cell lines, media was changed daily and cells were passaged every 2 to 3 days routinely.

Derivation of TA1 ES Cell Line

C57BL/6J females (The Jackson Laboratory, Bar Harbor, Me.) and 129S6/SvEvTac males (Taconic) were naturally mated to collect 2-cell embryos, which were then cultured in KSOM medium for 3 days at 37° C. in 5% $CO^2$. Resulting blastocysts were transferred onto mouse embryo fibroblast (MEF) feeder cells treated with mitomycin C (Sigma) and cultured for 7 days in the complete ES medium (described above) after replacing 15% FBS with 15% KSR (Invitrogen) and adding 50 nM PD98059 (MEK1 inhibitor). After picking inner cell mass (ICM) clumps and dissociating them by ACCUTASE™ (Millipore), they were seeded onto fresh feeder cells and cultured in the same condition for an additional 7 days. Newly derived ES cell lines were directly tested for their developmental potency by 4N-complementation (see below).

pCAG-Zscan4-ERT2 Vector Construction

Genes collectively called Zscan4 consist of 6 paralogous genes and 3 pseudogenes clustered on a ~850 kb region of chromosome 7 (Falco et al., *Dev Biol* 307:539-550, 2007). Among six paralogs named Zscan4a to Zscan4f, the open reading frames (ORFs) of Zscan4c, Zscan4d, and Zscan4f are very similar to each other and encode a SCAN domain and four zinc finger domains (Falco et al., *Dev Biol* 307:539550, 2007). To construct a pCAG-Zscan4-ERT2 plasmid, an entire ORF (506 a.a.) of mouse Zscan4c gene (Falco et al., *Dev Biol* 307:539-550, 2007) was fused with ERT2

(Feil et al., *Proc Natl Acad Sci USA* 93:10887-10890, 1996) (314 a.a.) and cloned into XhoI/NotI sites of pPyCAG-BstXI-IP (Niwa et al., *Gene* 108:193-199, 1991). The resultant plasmid vector expresses Zscan4c-ERT2 fusion protein-IRES-puromycin-resistant protein under a strong CAG promoter.

Generation of ZE and ZERT2 ES Cell Clones ES cells were grown in 6-well plates. For ZE ES cell clones, $5\times10^5$ ES cells in suspension were transfected with 1 μg of a linearized pZscan4-Emerald vector (Zalzman et al., *Nature* 464:858-863, 2010) using EFFECTENE™ (QIAGEN) according to manufacturer's protocol, and plated in 100 mm dishes. After selecting with 5 μg/ml blasticidin for 8 days, resulting ES cell colonies were picked, expanded, and frozen for further analysis. For ZERT2 ES cell clones, $5\times10^5$ ES cells in suspension were cotransfected with 0.5 μg of a linearized pCAG-Zscan4-ERT2 vector and 0.5 μg of PL452 (PGK promoter-Neo) (Liu et al., *Genome Res* 13:476-484, 2003) using EFFECTENE™ (QIAGEN) according to manufacturer's protocol, and plated in 100 mm dishes. After selecting with G418 for 8 days, resulting ES cell colonies were picked, expanded, and frozen for further analysis.

Quantitative Reverse Transcription Polymerase Chain Reaction (qRT-PCR)

RNA was isolated from cells by TRIZOL™ (Invitrogen) in biological triplicate. One μg of total RNA was reverse transcribed by SuperScript™ III (Invitrogen) following the manufacturer's protocol. 100 ng of oligo dT primers (Promega) was used per reaction. For qPCR, SYBR™ green master mix (Applied Biosystems) was used following the manufacturer's protocol. 96-well optical plates with a 25 μl total reaction volume were used, 10 ng of cDNA was used per well. Plates were run on 7300 or 7500 system (Applied Biosystems). Fold induction was calculated by the ΔΔCt method (Livak et al., *Methods* 25:402-408, 2001) using H2A as normalizer.

RNA Isolation, cDNA Preparation and qPCR Analysis in Mouse Preimplantation Embryos Four to six week-old B6D2F1 female mice were superovulated with 5 I.U. of PMSG (Sigma) and 5 I.U. of human chorionic gonadotropin (hCG) (Sigma). Eggs or embryos for qRT-PCR experiments were collected after 20, 23, 30, 43, 55, 66, 80 and 102 hours post hCG injection for MII (unfertilized oocytes), 1-cell, early and late-2 cell, 4-cell. 8-cell, morula and blastocyst embryos, respectively. Three sets of 10 synchronized eggs or embryos were stored in liquid nitrogen and mechanically ruptured by a freeze/thaw step for the cDNA preparation template. Oligo-dT primers and SuperScript™ III reverse transcriptase (Invitrogen) were used according to the manufacturer's instruction. Analysis was performed on the ABI 7300 Fast Real Time PCR system (Applied Biosystems). Data was normalized by Chuk (Falco et al., *Reprod Biomed Online* 13:394-403, 2006) with the ΔΔCt method (Livak et al., *Methods* 25:402-408, 2001).

RNA In Situ Hybridization

Whole mount in situ hybridization was performed as previously described (Carter et al., *Gene Expr Patterns* 8:181-198, 2008). Briefly, ES cells in triplicates, grown for 3 days, were fixed in 4% paraformaldehyde (PFA) at 4° C. overnight. After digestion with proteinase K, cells were hybridized with 1 μg/ml digoxigenin-labeled riboprobe at 62° C. overnight. Cells were then washed, blocked, incubated with alkaline phosphatase-conjugated anti-digoxigenin antibody, and incubated with NBT/BCIP detection buffer for 30 minutes or overnight.

Double-Fluorescence RNA In Situ Hybridization

Digoxigenin (DIG)- and biotin (BIO)-labeled RNA probes were transcribed from the PCR product templates using RNA Labeling Mix (Roche). Ethanol-precipitated probes were resuspended in water and quantified by RNA 6000 Nano Assay on a 2100 Bioanalyzer (Agilent Technologies). $10^5$ cells/well were seeded in glass chamber slides, cultured for three days, fixed with PFA, and permeabilized with 0.5% TritonX-100. Cells were washed and incubated with 1 μg/ml DIG and BIO probes for 12 hours at 60° C. in hybridization solution. Probes were detected by mouse anti-DIG antibody and by sheep anti-BIO, and visualized by fluorophore-conjugated secondary antibodies. Nuclei were stained with DAPI (blue).

Microarray Analysis

DNA microarray analyses were carried out as described (Aiba et al., *DNA Res* 16:73-80, 2009). Briefly, universal Mouse Reference RNA (Stratagene) were labeled with Cy5-dye, mixed with Cy3-labeled samples, and used for hybridization on the NIA Mouse 44K Microarray v2.2 (Carter et al., *Genome Biol* 6:R61, 2005) (manufactured by Agilent Technologies #014117). The intensity of each gene feature was extracted from scanned microarray images using Feature Extraction 9.5.1.1 software (Agilent Technologies). Microarray data analyses were carried out by using an application developed in-house to perform ANOVA and other analyses (NIA Array Analysis software; online at lgsun.grc.nia.nih.gov/ANOVA/) (Sharov et al., *Bioinformatics* 21:2548-2549, 2005). All the DNA microarray data have been deposited to the NCBI Gene Expression Omnibus (GEO, online at www.ncbi.nlm.nih.gov/geo/) and are accessible through GEO Series accession number (GSE26278) and the NIA Array Analysis software website (online at lgsun.grc.nia.nih.gov/ANOVA/) (Sharov et al., *Bioinformatics* 21:2548-2549, 2005). For GEO reviewer link: www.ncbi.nlm.nih.gov/geo/query/acc.cgi?token=fhaxtmiueykigvm&acc=GSE26278.

ES Cell Injection into 2N or Tetraploid (4N) Blastocysts

CD1 females (Charles River, 8-12 week old) were used for superovulation by PMSG (Sigma) followed 48 hours later by hCG (Sigma) administration. After hCG administration, females were mated with males of the same strain and 2-cell embryos were collected by flushing oviducts. Recovered embryos were cultured in KSOM (Millipore) medium for 3 days at 37° C. in 5% $CO^2$. Collected 2-cell embryos were directly transferred into 0.3 M mannitol solution and aligned automatically by alternate current (AC) pulse in an electrofusion chamber. Then two direct current (DC) pulses with 140V/mm were applied for 40 μs using LF101 Electro Cell Fusion Generator. Fused embryos (4N) that had one blastomere were collected at 60 minutes cultivation and then culture continued in KSOM medium until they reached the blastocyst stage. A single ES cell or 10-15 ES cells were injected into 2N or 4N blastocysts to assess their developmental potency and then transferred to E2.5 recipient females. To study the effects of Tmx on ES cells. ES cells were cultured in the presence of 200 nM Tmx for 2-3 days before injection.

Example 2: Rejuvenation of Pluripotent Stem Cells by Frequent Activation of Zscan4

This example describes the finding that increasing the frequency of Zscan4 activation in mouse ES cells not only enhances, but also maintains their developmental potency in long-term cell culture.

Commonality Between Transient Zscan4$^{+}$ State and 2-Cell Stage Embryos

As a first step to characterize the Zscan4$^{+}$ state of ES cells, global gene expression profiles were compared between Zscan4$^{+}$ and Zscan4$^{+}$ state of ES cells. In an earlier study, a reporter cell line, pZscan4-Emerald cells (hereafter called "MC1ZE"), was established in which a Zscan4c-promoter-driven reporter green fluorescence protein GFP-Emerald (Em) recapitulates the expression of endogenous Zscan4 (Zalzman et al., *Nature* 464:858-863, 2010). DNA microarray analysis of FACS-sorted Em$^{+}$ and Em$^{-}$ cells was carried out. Em$^{+}$ cells showed a very similar gene expression profile to the Em$^{-}$ cells with only 161 differentially expressed genes (FIG. 5; see also PCT Publication No. WO 2008/118957 and Falco et al., *Dev Biol* 307:539-550, 2007). Pluripotency-related markers remained unchanged in Em$^{+}$ cells compared to Em$^{-}$ cells, but Tcstv1 and Tcstv3 (two cell-specific transcript variant 1 and 3) genes (Struwe and Solter, GenBank accession AF067057.1; Zhang et al., *Nucleic Acids Res* 34:4780-4790, 2006) were among the most highly upregulated genes (FIG. 5). RNA whole-mount in situ hybridization revealed "Zscan4-like" expression for 7 other genes in the list (Tcstv1/3, Eif1a, Pif1, AF067063, EG668777, RP23-149D11.5, BC061212, and EG627488; see PCT Publication No. WO 2008/118957, herein incorporated by reference).

Furthermore, double-label fluorescence RNA in situ hybridization confirmed co-expression of these genes with Zscan4. As Zscan4 is a 2-cell embryo marker (Falco et al., *Dev Biol* 307:539-550, 2007), 6 genes were selected from the list based on additional gene expression information in preimplantation embryos (Ko et al., *Development* 127:1737-1749, 2000; Sharov et al., *PLoS Biol* 1:E74, 2003) and were examined for their expression profiles by qRT-PCR. All six genes tested showed a high expression peak in 2-cell embryos: 2 genes showed the highest peak at the late 2-cell stage as Zscan4, whereas 4 others showed their highest peak at the early 2-cell stage (see PCT Publication No. WO 2008/118957, herein incorporated by reference). Considering the fact that a large-scale screening of ~250 transcription factor genes by whole-mount in situ hybridization identified only two other genes (Rhox9 and Whsc2) with a "Zscan4-like" expression pattern (Carter et al., *Gene Expr Patterns* 8:181-198, 2008), the high incidence of finding 2-cell genes with a Zscan4-like expression pattern in ES cells suggests that some of the gene expression program in early-stage embryos are reactivated in the Zscan4$^{+}$ state of ES cells.

Transient Zscan4$^{+}$ State is not Associated with Higher Developmental Potential ES cells are thought to be equivalent to cells in the inner cell mass (ICM) of blastocysts (Nichols and Smith, *Development* 138:3-8, 2011; Yoshikawa et al., *Gene Expr Patterns* 6:213-224, 2006). Commonality between Zscan4$^{+}$ state and 2-cell embryos suggest that in standard cell culture conditions, ES cells are a mixed population of ~5% of 2-cell like cells and ~95% of ICM-like cells. As it has been shown that by nuclear transplantation (cloning) the 2-cell nucleus has a higher developmental potential than the ICM nucleus (Tsunoda et al., *Development* 107:407-411, 1989; Kono et al., *J Reprod Fertil* 93:165-172, 1991), the Zscan4$^{+}$ state may represent high-potential true stem cells among the regular ES cell population.

To test this notion, V6.5 ZE cells (clone #17) were generated and their developmental potency was assessed by transfecting a pZscan4-Emerald vector into V6.5 ES cells derived from an F1 hybrid strain (C57BL/6×129/Sv), which has been extensively used for testing developmental potency (Eggan et al., *Proc Natl Acad Sci USA* 98:6209-6214, 2001; Wang and Jaenisch, *Dev Biol* 275:192-201, 2004). To avoid cell damage caused by cell sorting or long UV exposure, Em$^{+}$ or Em$^{-}$ cells were separated manually by pipetting, single ES cells were injected into 2N blastocysts, and the subsequent embryo development was observed. Based on the coat colors, it was found that Em$^{-}$ ES cells were able to contribute to the tissues of chimeric mice at a relatively high rate (31%), whereas Em$^{+}$ ES cells were not (0%). The results indicate that, contrary to expectations, Zscan4$^{+}$ cells are not associated with high developmental potency compared to Zscan4$^{-}$ cells.

Zscan4-ERT2 Increases the Frequency of Endogenous Zscan4$^{+}$ Cells in the Absence of Tmx Intermittent and transient activation of Zscan4 is required for the long-term maintenance of ES cell cultures (Zalzman et al., *Nature* 464:858-863, 2010). It was therefore hypothesized that more frequent activation of Zscan4 further improves the quality of ES cells, including their developmental potency. A system to mimic the transient expression of Zscan4 was sought. To this end, ERT2, the tamoxifen (Tmx) inducible system was selected (Feil et al., *Proc Natl Acad Sci USA* 93:10887-10890, 1996). This system allows one to keep a transgene off in the absence of Tmx and turn it on in the presence of Tmx at will (Feil et al., *Proc Natl Acad Sci USA* 93:10887-10890, 1996). First, the plasmid construct pCAG-Zscan4-ERT2 was made in which Zscan4c open reading frame (ORF) fused with ERT2 domain can be driven by a strong ubiquitous promoter CAG (Niwa et al., *Gene* 108:193-199, 1991) (FIG. 1A).

When the pCAG-Zscan4-ERT2 plasmid was transfected into MC1-ZE3 cells, it was found that the constitutive expression of Zscan4-ERT2 in ES cells increased the fraction of Em$^{+}$ cells even in the Tmx$^{-}$ condition (FIG. 1B). Adding Tmx to the culture media further increased the fraction of Em$^{+}$ cells, but also made ES cells (both Em$^{+}$ and Em$^{-}$ cells) flatter, resulting in the flattening of ES cell colonies—a deviation from the typical pluripotent ES colony morphologies (FIG. 1B). The results were further confirmed by quantitative assays for five independent clones: the constitutive expression of Zscan4-ERTs even in the absence of Tmx caused a 3-fold increase of Em$^{+}$ cells by the flow cytometry analysis (FIG. 1C) and 5-fold increase by the qRT-PCR analysis (FIG. 1D); and addition of Tmx to the medium caused further 2-fold and 1.2 fold increase, respectively (FIGS. 1C-1D).

Figure 6A:
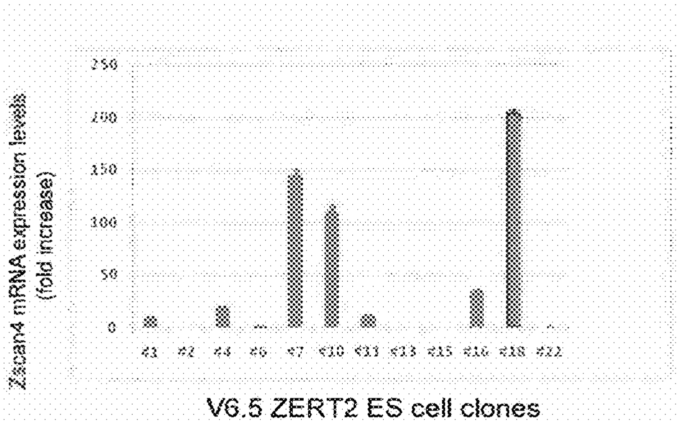
FIGS. 6A-6C: Generation and characterization of V6.5 ZERT2 ES cell clones.
Figure 6B:
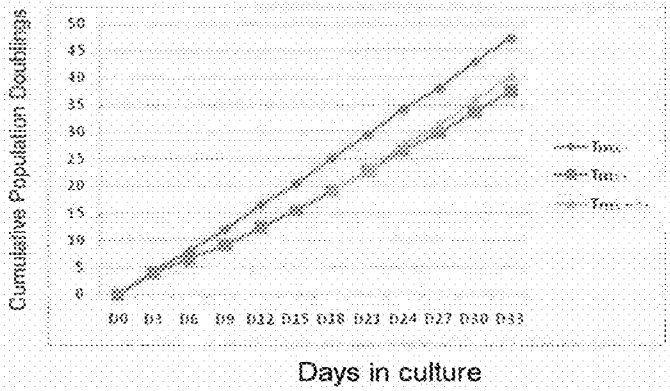
Figure 6C:
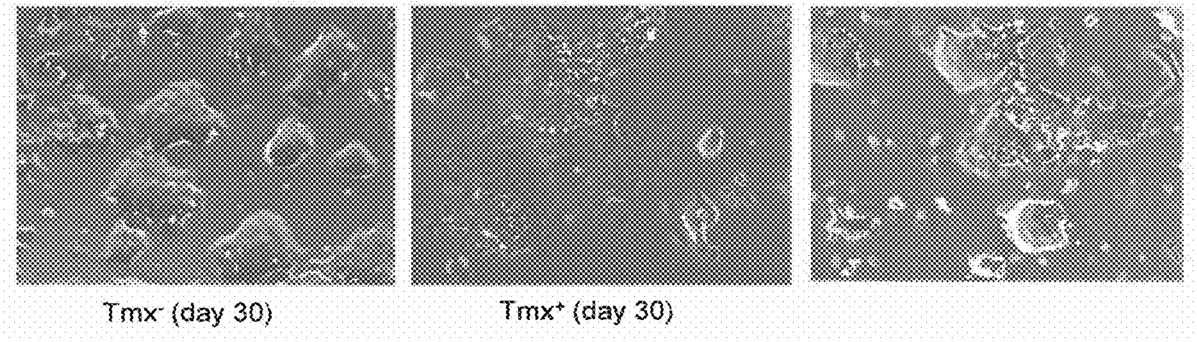

To further investigate this unexpected result, the pCAG-Zscan4-ERT2 plasmid was transfected into V6.5 ES cells (Eggan et al., *Proc Natl Acad Sci USA* 98:6209-6214, 2001) and multiple cell clones named V6.5 ZERT2 were isolated. Based on the qRT-PCR analysis of Zscan4 ORF, clone #18 was selected for the highest Zscan4 expression levels, clones #7 and #10 were selected for the second and third highest Zscan4 levels, and clone #2 was selected with the background Zscan4 level (FIG. 6A). Based on genotyping by PCR, clone #2 did not have any copies of the pCAG-Zscan4ERT2 plasmid, and was thus used as a control (V6.5 #2). As expected, Tmx$^{+}$ conditions slowed down the proliferation of ES cells (FIG. 6B) and made ES cells flatter (FIG. 6C). When the Tmx was removed from the medium after 10 passages in the Tmx$^{+}$ conditions, the cell proliferation and morphology returned to normal (FIGS. 6B-6C), suggesting that effects of Tmx on the V6.5 ZERT2 cells were reversible.

Figure 7A:
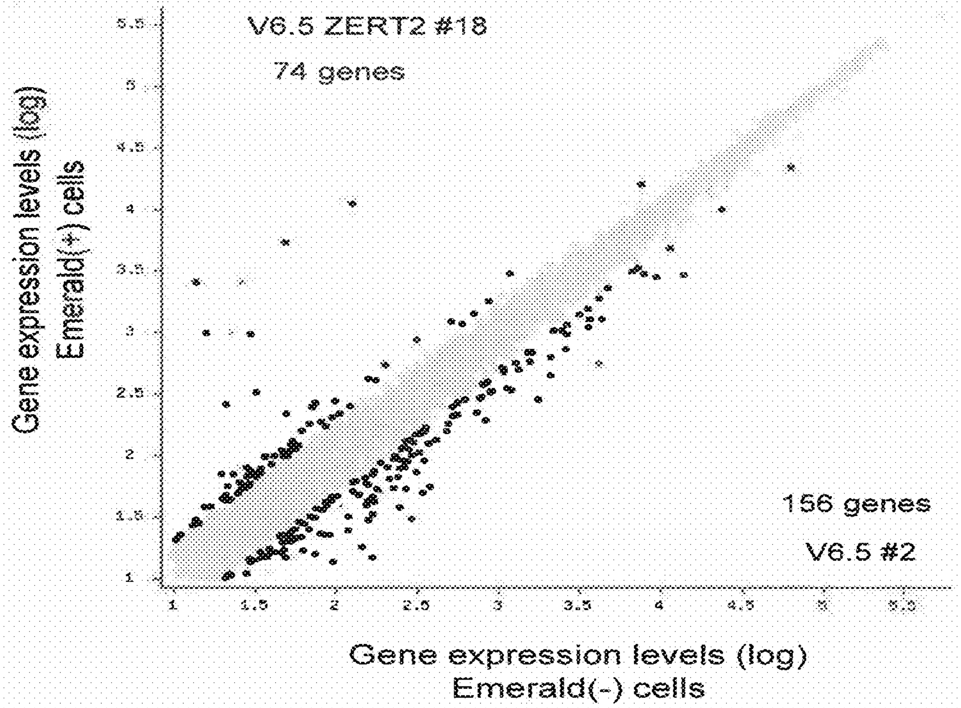
FIG. 7A is a scatter plot showing genes expressed differentially between V 6.5 ZERT2 #18 ES cells and control V6.5 #2 ES cells.
Figure 7B:
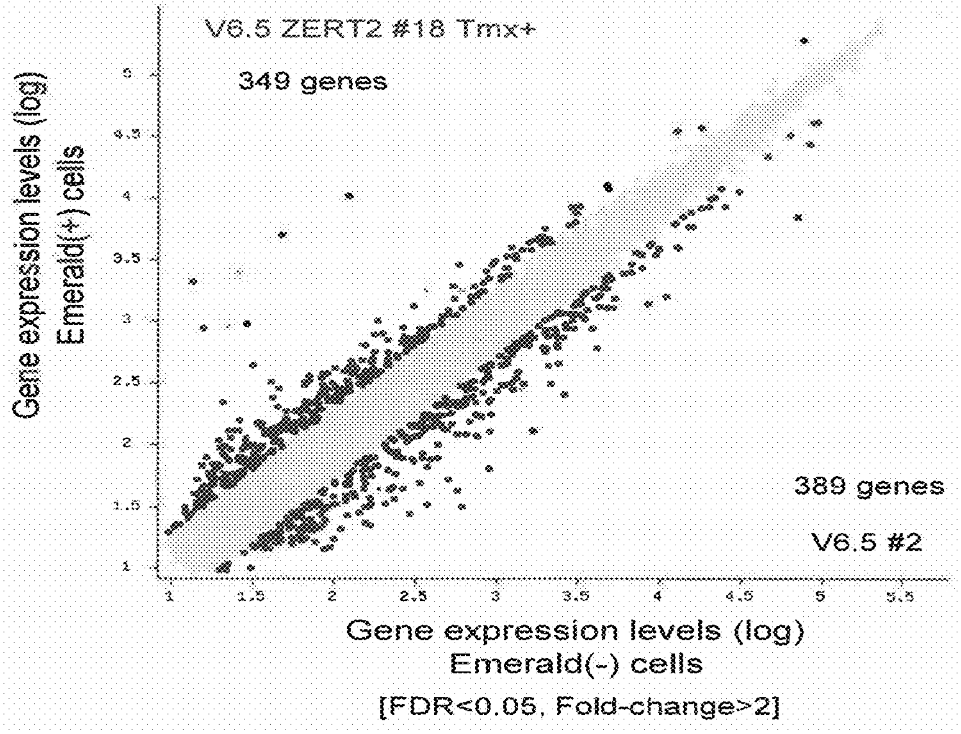
FIG. 7B is a scatter plot showing genes expressed differentially between V6.5 ZERT2 #18 ES cells cultured for 2 days in the presence of Tmx and control V6.5 #2 ES cells.

To check if the frequency of Zscan4$^{+}$ cells is increased even in the Tmx condition, whole mount in situ hybridization was carried out using a full-length Zscan4c probe to detect both endogenous and exogenous copies of Zscan4 as well as a 3'-UTR Zscan4c probe to detect only endogenous Zscan4. The results showed ~3-fold increase of the number of Zscan4$^+$ cells in V6.5 ZERT2 ES cell clones (#7, #10, and #18) in the absence of Tmx compared to the usual level of Zscan4$^+$ cells in the control cells (V6.5 and V6.5 #2) (FIG. 1E). Further comparison of global gene expression profiles by DNA microarrays confirmed that the expression of Zscan4 was upregulated by 3.6-fold in V6.5 ZERT2 #18 ES cells even in the Tmx$^-$ condition (FIGS. 7 and 8). Similarly, other key Zscan4-related genes identified in Falco et al. (*Dev Biol* 307:539-550, 2007), such as Tcstv1, Tcstv3, Tmem92, RP23-149D11.5, and BC061212, were also upregulated in V6.5 ZERT2 #18 ES cells in the Tmx$^-$ condition (FIG. 1F, FIG. 7, FIG. 8). Adding Tmx increased the expression of Zscan4 and other Zscan4-related genes only slightly, but increased that of Zscan4-unrelated genes significantly (FIG. 1G, FIG. 7 and FIG. 9). Taken together, use of constitutively expressing Zscan4-ERT2 without Tmx became an unexpected, but attractive strategy to enhance the naturally occurring Zscan4 effects by increasing the number of endogenous Zscan4$^+$ cells.

Zscan4 Protein Lacking the C-Terminus (Zscan4c-ΔC) Increases the Number of Zscan4$^+$ Cells Based on the results described above, it was hypothesized that the effect of ERT2 was due to blocking the function of the Zscan4 zinc finger domains at the C-terminus of the protein. Thus, to evaluate whether C-terminally truncated Zscan4 has the same effect as Zscan4-ERT2 of inducing recurrent activation of Zscan4, vectors encoding either C-terminal truncated (lacking all four zinc finger domains) or N-terminal truncated (lacking the SCAN domain) Zscan4 were constructed. FIG. 2A provides a schematic of the structure of Zscan4c, Zscan4c-ERT2, Zscan4c-ΔC and Zscan4c-ΔN proteins. The amino acid sequence of Zscan4c-ΔC is set forth herein as SEQ ID NO: 25.

The mutated Zscan4c genes were placed under the strong and constitutive CAG promoter. The sequence of the pCAG-Zscan4-ΔC vector is set forth herein as SEQ ID NO: 24. Each vector was transfected into MC1-ZE16 ES cells (sister clones of MC1-ZE3). Multiple independent clones were isolated: ZDC-MC1-ZE16 #3, #4, #20 for Zscan4c-ΔC; ZDN-MC1-ZE16 #5, #8, #15 for Zscan4c-ΔN. Fluorescence microscopy was performed on each cell clone. The images of ZDC-MC1-ZE16 #3, #4, #20 and ZDN-MC1-ZE16 #5, #8, #15 are shown in FIGS. 2B-2G. The results clearly show that the expression of Zscan4c-ΔC increases the number of Zscan4$^+$ cells, whereas the expression of Zscan4c-ΔN does not change the number of Zscan4$^+$ cells. The results indicate that Zscan4c-ΔC functions in a manner similar to Zscan4-ERT2 (Tmx− condition).

Figure 3A:
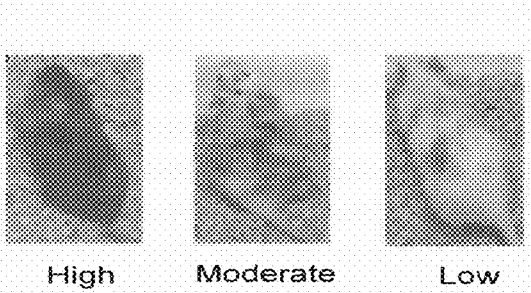
FIGS. 3A-3B: Constitutive expression of a Zscan4c-ERT2 fusion protein increases and prolongs developmental potency of ES cells.

Zscan4-ERT2 Enhanced and Prolonged Developmental Potency of ES Cells in the Absence of Tmx To assess the effects of Zscan4-ERT2 on the developmental potency of ES cells, various ES cells were injected into mouse blastocysts, transferred to uteri, and their development was followed. The extent of ES cell potency was assessed by the percent chimerism in the pups based on coat colors: high (>70% chimerism), moderate (40%70%), low (<40%), and albino (0%) (FIG. 3A).

Figure 3B:
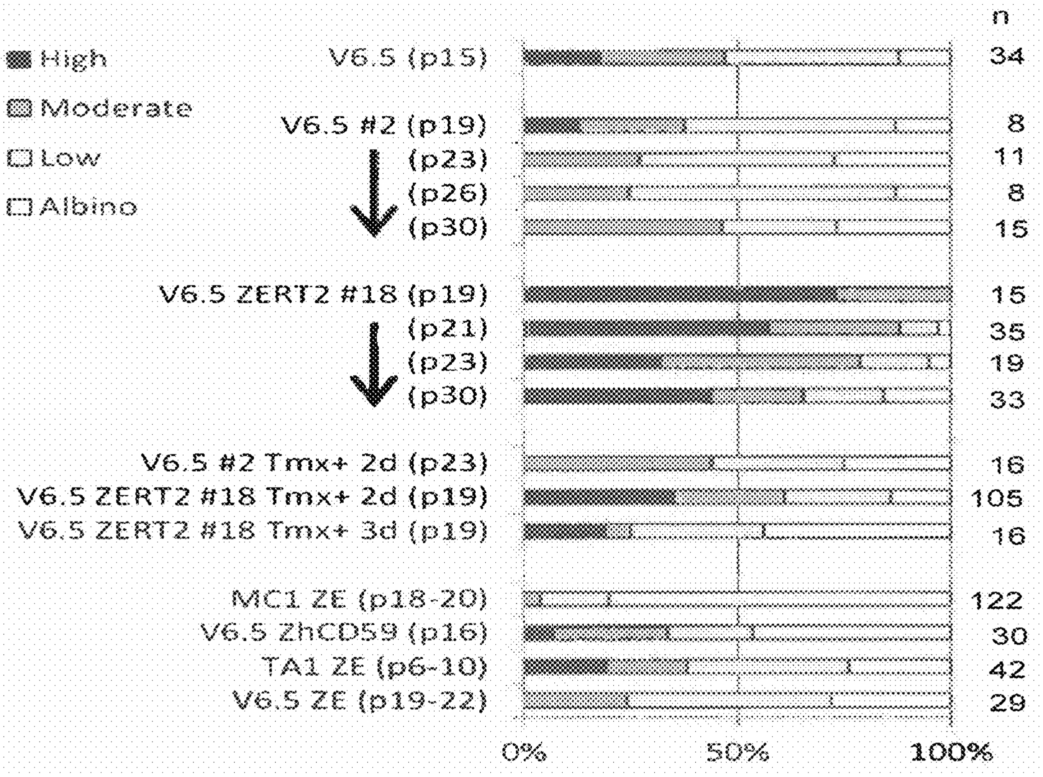

A V6.5 parental ES cell line at its early passage (p15) showed 18% high, 29% moderate, and 41% low chimerism, which are within the standard range for F1 hybrid ES cell lines. It is known that the developmental potency of ES cells generally becomes lower after multiple passages and/or plasmid transfection/drug selection. As expected, compared to a V6.5 parental ES cell line, a control V6.5 #2 ES cell line, which did not carry Zscan4-ERT2 but was generated after transfection and drug selection, showed a slightly lower overall potency, which was further reduced over multiple passages (p21, p23, and p30) (FIG. 3B). By contrast, V6.5 ZERT2 #18 ES cells showed much higher developmental potency than parental V6.5 and control V6.5 #2 ES cells: 73% high and 27% moderate chimerism at passage 19 (FIG. 3B). Even more surprising was that such a high level of potency was maintained for an extended period of time and passages: for example, even at passage 30, more than 40% of pups derived from V6.5 ZERT2 #18 ES cells showed "high" chimerism, whereas none of the pups derived from control V6.5 #2 ES cells showed "high" chimerism (FIG. 3B). Five other ES cell lines of different genetic backgrounds and transgenes were tested, including a very early passage line from freshly isolated ES cells (TA1). Potency-wise none of these ES cell lines could even come close to V6.5 ZERT2 #18 cell lines (FIG. 3B).

Interestingly, the exposure to Tmx for 2 to 3 days lowered the potency of both V6.5 #2 and V6.5 ZERT2 #18 ES cells relative to that in the Tmx$^-$ condition, although the V6.5 ZERT2 #18 ES cells still showed higher potency than V6.5 #2 ES cells (FIG. 3B). These results seem to be consistent with the observation made by the global expression profiling (FIG. 1F): Tmx$^+$ conditions increased the expression of genes unrelated to naturally occurring Zscan4$^+$ (i.e., Em$^+$) state in V6.5 ZERT2 #18 ES cells.

Testing Developmental Potency of ES Cells by the 4N Complementation Assay

It is widely recognized that the ultimate test for developmental potency is to see if ES cells alone injected into tetraploid (4N) blastocysts become an entire mouse (Nagy et al., *Development* 110:815-821, 1990). Compared to early passage V6.5 ES cells reported previously, which has achieved 15-25% pups alive at term (Eggan et al., *Proc Natl Acad Sci USA* 98:6209-6214, 2001), V6.5 ES cells at passage 18 only produced 2% live embryos (FIG. 4A). By contrast. V6.5 ZERT2 #18 ES cells even at passage 19 showed a much higher success rate—43% live embryos (FIGS. 4A and 4C). Similarly, two other independent clones (V6.5 ZERT2 #7; V6.5 ZERT2 #10) also showed a high success rate of producing live embryos when 10-15 ES cells were injected into 4N blastocysts (FIG. 4A).

Figures 11A, 11B:
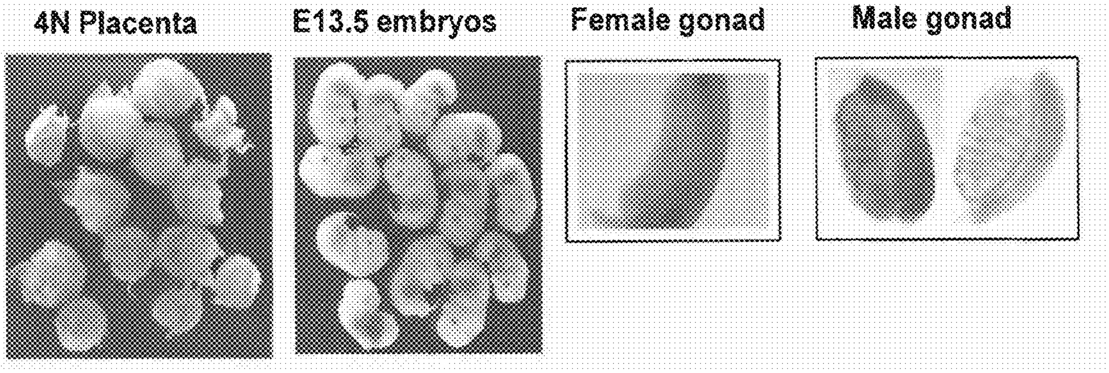
FIGS. 11A-11B: Testing developmental potency of newly derived F1 hybrid ES cell lines by tetraploid complementation assays.

To compare the high success rate of V6.5 ZERT2 #18 cells with those of the best ES cells possible, freshly isolated ES cells were established from blastocysts with the same genetic background—F1 hybrid of C57BL/6J×129S6/SvEvTac and were cultured in the best conditions currently available (Wong et al., *Methods Enzymol* 476:265-283, 2010) (FIG. 10 and FIG. 11). Of 20 blastocysts, 19 formed outgrowths in vitro, 13 of which continued to be cultured for an additional 7 days to form ES cell colonies, resulting in newly established ES cell lines (FIG. 10). Six clones out of 13 ES cell lines at the earliest passages (p3) were tested for their potency by injecting 10-15 ES cells into 4N blastocysts: one ES line, named "TA1", showed the highest efficiency (60%) of producing live embryo at E13.5 (FIG. 4A and FIG. 11). Overall, these results obtained by the 4N complementation assays indicate that the developmental potency of V6.5 ZERT2 #18 ES cells even at the higher passage number is comparable to that of freshly isolated early passage ES cells.

To exclude the possibility that Zscan4-ERT2 affects only F1 hybrid ES cell lines, MC2 ZERT2 #6 ES cells were generated by transfecting a Zscan4-ERT2 plasmid to an MC2 ES cell line (C57BL/6J) (Olson et al., *Cancer Res* 63:6602-6606, 2003). Consistent with the reported low potency of C57BL/6J-derived ES cells (Brook et al., *Proc Natl Acad Sci USA* 94:5709-5712, 1997; Eggan et al, *Proc*

*Nat Acad Sci USA* 98:6209-6214, 2001), both MC2 ES cells at passage 17 and genetically modified MC2 ES cells at passage 12-13 did not produce any live embryos (FIG. 4A). By contrast, MC2 ZERT2 #6 ES cells, which were cultured for more than 10 passages with the constitutive expression of Zscan4-ERT2, successfully achieved the production of 6% live embryos (FIG. 4A). The results thus suggest that the Zscan4-ERT2 construct can be used as a universal tool to enhance the developmental potency of pluripotent stem cells.

The unusually high developmental potency of V6.5 ZERT2 #18 cells prompted the further examination of the potency of single ES cells. It has been shown once that even a single ES cell can form a live pup, although the success rate is extremely low (1 mouse/192 injected blastocyst: 0.5%) (Wang and Jaenisch, *Dev Biol* 275:192-201, 2004). As expected from the fact that the same cell line was used as for the earlier study (Wang and Jaenisch, *Dev Biol* 275:192-201, 2004), the injection of a single parental V6.5 ES cell at passage 18 into 4N blastocysts produced one live embryo (1%) (FIG. 4B). Furthermore, single control V6.5 #2 ES cells did not produce any live embryos after injecting them into 77 tetraploid blastocysts (FIG. 4B). By contrast, of 44 tetraploid blastocysts that received a single V6.5 ZERT2 #18 cell, 3 (7%) became complete embryos, 2 (5%) of which were alive at the time of dissection (FIGS. 4B and 4D). This unusually high level of potency for V6.5 ZERT2 #18 ES cells was indeed comparable to that of early passage TA1 ES cells with 4% live embryos (FIG. 4B).

Discussion

It is disclosed herein that the constitutive presence of Zscan4-ERT2, without its usual activator Tmx, can increase the frequency of endogenous Zscan4 activation, resulting in the increase of developmental potency of ES cells. ES cells cultured in the accelerated Zscan4 activation cycle show improved chimerism and potency, which are demonstrated by high contribution to chimeric mice and efficient production of a whole mouse from a single ES cell.

How does the frequent activation of Zscan4 enhance and prolong the developmental potency of ES cells? Previously, it was demonstrated that the immortality of ES cells is maintained by an intermittent activation of Zscan4 (Zalzman et al., *Nature* 464:858-863, 2010). The shRNA-mediated continuous repression of Zscan4 makes ES cells undergo culture crisis after multiple cell passages (Zalzman et al., *Nature* 464:858-863, 2010). It is thus conceivable that even in their regular proliferating condition ES cells gradually lose their potency, which is rapidly restored by the transient activation of Zscan4 (Zalzman et al., *Nature* 464:858-863, 2010). Consistent with the notion that drastic changes, including rapid telomere extension by telomere sister chromatid exchange (Zalzman et al., *Nature* 464:858-863, 2010), are occurring in ES cells in $Zscan4^+$ state, $Zscan4^+$ cells ($Em^+$ cells in the experiments described herein) did not produce chimeric animals when injected into blastocysts. In standard ES cells, the interval of transient Zscan4 activation may be longer than ideal; thus, ES cells steadily lose their average potency, irrespective of the occasional activation of Zscan4 (FIG. 4E, upper panel). More frequent activation of Zscan4 by the presence of Zscan4-ERT2 may maintain or even increase ES cell potency (FIG. 4E, lower panel).

Activation of endogenous Zscan4 by Zscan4-ERT2 without Tmx was unexpected, because ERT2-fusion proteins usually require Tmx for their activation. It is speculated that this may be related to a partial blocking of Zscan4 function, because the ERT2 domain is fused to the C-terminus of Zscan4, near four zinc-finger (C2H2) domains, whereas a SCAN domain is located at the N-terminus (Falco et al., *Dev Biol* 307:539-550, 2007). Considering the fact that Zscan4 should not be constitutively active in ES cells, the unexpected finding of Zscan4-ERT2 function provides an ideal means to increase the intermittent activation of endogenous Zscan4 expression. Irrespective of the mechanism, the presence of Zscan4-ERT2 in ES cells has beneficial effects on the potency of ES cells in long-term culture.

In view of the many possible embodiments to which the principles of the disclosure may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

Example 3: Overexpression of Zscan4c Alone can Rejuvenate ES Cells

Figure 12:
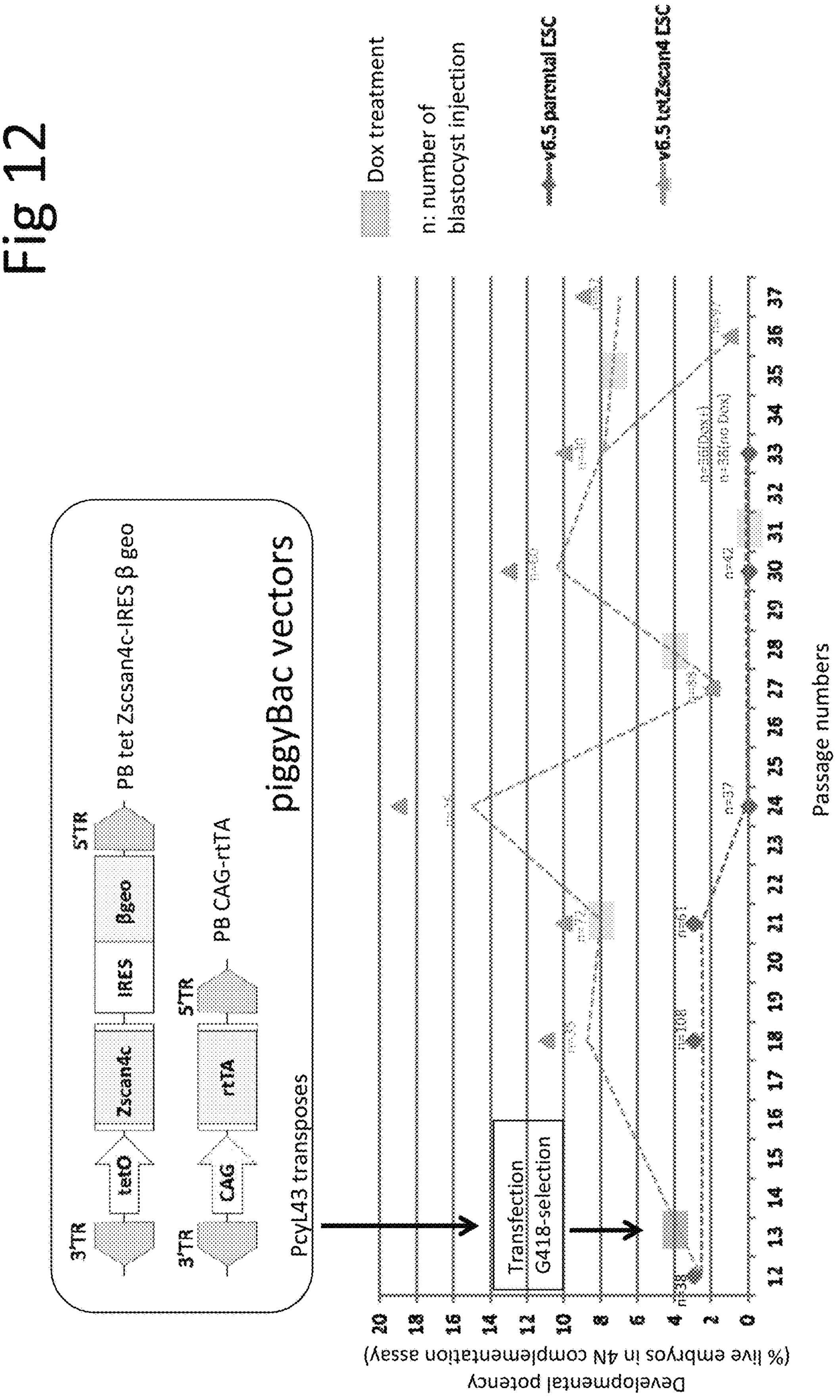
FIG. 12: Testing transient overexpression of Zscan4 (i.e., unmodified Zscan4.

To test whether transient overexpression of Zscan4 itself (i.e., unmodified Zscan4 protein) can increase the developmental potency of ES cells, we made a PB-tetZsan4c-IRES-beta-geo vector, in which the expression of the Zscan4c ORF is driven by the Dox-inducible tetO promoter (FIG. 12). The vector also contains beta-geo, G418-resistant gene, so that only the ES cells that contain Dox-inducible Zscan4c vector can be selected in the presence of G418. This piggyBAC vector was cotransfected with PB-CAG-rtTA vector (Dox-transactivator, which is necessary for the Dox-indelibility of teO promoter) and PcyL43 transposase vector (an enzyme that facilitates the integration of piggyBAC vectors into the genome). After the transfection, cells were cultured in the presence of G418 and Dox+ for 6 days, and then cultured in the absence of Dox subsequently. These cells were named V6.5 tetZscan4 ESC. As a control, parental V6.5 ES cells were used. The expression of Zscan4 can be transiently increased by adding Dox in the culture media (shown in blue box, FIG. 12).

These cells were cultured and passaged every 3 days. At certain passages, these cells were injected into tetraploid (4N) blastocysts to see whether these cells can form live mouse embryos at E13.5. The percent fraction of live embryos out of the number of injected blastocysts represents the developmental potency of ES cells (y-axis of FIG. 12).

As expected, control V6.5 ES cells showed the highest developmental potency (3%) at the early passage (passage 12), which declined gradually over multiple passages (FIG. 12). At the passage 24, control V6.5 ES cells completely lost their potency. By contrast, V6.5 tetZscan4c ES cells showed the increase of developmental potency after the transient Zscan4 overexpression from 3% (passage 12) to 9% (passage 18). When cells began to lose their developmental potency, we added Dox to the culture medium and transiently overexpressed Zscan4. As shown in FIG. 12, the transient overexpression of Zscan4 was able to increase the developmental potency of ES cells. Subsequently, we were able to show that by occasionally overexpressing Zscan4. ES cells can main their developmental potency even after long term cell culture (tested up to 37 passages).

These data clearly demonstrated that the transient overexpression of Zscan4 alone can increase the developmental potency (i.e., rejuvenate) ES cells.

The invention claimed is:

1. An in vitro method of prolonging pluripotency, increasing frequency of Zscan4-positive cells and/or increasing telomere length of a mouse embryonic stem (ES) cell, the method comprising:

a) transfecting an expression vector comprising a nucleic acid encoding a Zscan4-ΔC protein consisting of the amino acid sequence as set forth in SEQ ID NO:25 into the mouse ES cell; and b) culturing the transfected mouse ES cell in culture medium such that the Zscan4-ΔC protein is expressed in the mouse ES cell.

2. An in vitro method of prolonging pluripotency, increasing frequency of Zscan4-positive cells and/or increasing telomere length of a mouse embryonic stem (ES) cell, the method comprising:

a) transfecting an expression vector comprising a nucleic acid encoding a Zscan4-ERT2 fusion protein consisting of the amino acid sequence as set forth in SEQ ID NO:22 or SEQ ID NO:23 into the mouse ES cell; and b) culturing the transfected mouse ES cell in culture medium lacking tamoxifen such that the Zscan4-ERT fusion protein is expressed in the mouse ES cell.

3. The method of claim 2, wherein the Zscan4-ERT2 fusion protein consists of the amino acid sequence of SEQ ID NO:23.

4. The method of claim 2, wherein the Zscan4-ERT2 fusion protein consists of the amino acid sequence of SEQ ID NO:22.

* * * * *